US006855314B1

(12) United States Patent
Chiorini et al.

(10) Patent No.: US 6,855,314 B1
(45) Date of Patent: Feb. 15, 2005

(54) AAV5 VECTOR FOR TRANSDUCING BRAIN CELLS AND LUNG CELLS

(75) Inventors: John A. Chiorini, Kensington, MD (US); Robert M. Kotin, Bethesda, MD (US); Beverly Davidson, North Liberty, IA (US); Joseph Zabner, Iowa City, IA (US)

(73) Assignees: The United States of America as represented by the Department of Health and Human Services, Washington, DC (US); University of Iowa Research Foundation, Iowa City, IA (US)

(*) Notice: Subject to any disclaimer, the term of this patent is extended or adjusted under 35 U.S.C. 154(b) by 0 days.

(21) Appl. No.: 09/533,427

(22) Filed: Mar. 22, 2000

(51) Int. Cl.[7] .................. A01N 63/00; A01N 65/00; A01N 43/04; C12N 15/63; C12N 15/85
(52) U.S. Cl. .................. 424/93.2; 424/93.1; 424/93.6; 435/320.1; 435/455; 514/44
(58) Field of Search .................. 514/44; 424/93.1, 424/93.2, 93.6; 435/320.1, 455

(56) References Cited

U.S. PATENT DOCUMENTS

| | | | |
|---|---|---|---|
| 6,180,613 B1 * | 1/2001 | Kaplitt et al. | |
| 6,221,349 B1 * | 4/2001 | Couto et al. | |
| 6,309,634 B1 * | 10/2001 | Bankiewicz et al. | |
| 6,391,858 B2 * | 5/2002 | Podsakoff et al. | |

FOREIGN PATENT DOCUMENTS

| | | |
|---|---|---|
| DE | 44 36 664 A1 | 7/1996 |
| WO | WO 93/24641 | 12/1993 |
| WO | WO 96/00587 | 1/1996 |
| WO | WO 96/15777 | 5/1996 |
| WO | WO 98/11244 | 3/1998 |
| WO | WO 98/41240 | 9/1998 |
| WO | WO 98/45462 | 10/1998 |

OTHER PUBLICATIONS

RG Crystal, Science, "Transfer of Genes to Humans: Early Lessons and Obstacles to Success,"Oct. 1995, vol. 270, pp. 404–410.*

MP Deonarain, Molecular Conjugate Vectors, "Ligand–targeted receptor–mediated vectors for gene delivery,"1998, 8(1):53–69.*

Virologie et al. Analysis of proteins helper dependence, and seroepidemiology of a new human parvovirus pp. 64–71 1984.*

Zabner et al. "Adeno–associated virus type 5 (AAV5) but not AAV2 binds to the apical surfaces of airway epithelia and facilitates gene transfer" *J of Virology* 74(8): 3852–8, Apr. 2000.

Davidson et al. "Recombinant Adeno–associated Virus Type 2, 4, and 5 Vectors: Transduction of Variant Cell Types and Regions in the Mammalian Central Nervous System" *Proc. Natl Acad Sci.* 97(7):3428–32, Mar. 2000.

Chiorini et al. "Cloning and Characterization of Adeno–Associated Virus Type 5" *J of Virology* 73(2):1309–1319, Feb. 1999.

Prasad et al. "Characterization of the Rep 78/Adeno–Associated Virus Complex" *Virology* 229:183–192, 1997.

(List continued on next page.)

*Primary Examiner*—Anne-Marie Falk
(74) *Attorney, Agent, or Firm*—Needle & Rosenberg

(57) ABSTRACT

The present invention provides methods of delivering nucleic acids to specific regions, tissues and cell types of the CNS. More particularly the invention provides methods of delivering nucleic acids to cells of the CNS such as cerebellar cells and ependymal cells. The invention also provides methods of delivering nucleic acids to cells of the lung such as alveolar cells using AAV5 vectors and particles.

9 Claims, 35 Drawing Sheets

OTHER PUBLICATIONS

Maeda et al. "Gene transfer into vascular cells using adeno–associated virus (AAV) vectors" *Cardiovascular Research* 35:514–521, 1997.

During, MJ and Leone P. "Adeno–Associated Virus Vectors for Gene Therapy of Neurodegenerative Disorders" *Clinical Neuroscience* 3:292–300, 1996.

Kyostio et al. "Analysis of Adeno–Associated Virus (AAV) Wild–Type and Mutant Rep Proteins for Their Abilities to Negatively Regulate AAV $p_5$ and $p_{19}$ mRNA Levels" *J of Virology* 68(5):2947–2957, May 1994.

Im, D–S and Muzyczka N. "Partial Purification of Adeno–Associated Virus Rep78, Rep52, and Rep40 and Their Biochemical Characterization" *J of Virology* 66(2):1119–1128, Feb. 1992.

Mitrani et al. "Activin can induce the formation of axial structures and is expressed in the hypoblast of the chick" *Cell* 63:495–501, 1990.

Samulski et al. "Helper–Free Stocks of Recombinant Adeno–Associated Viruses: Normal Integration Does Not Require Viral Gene Expression" *J of Virology* 63(9):3822–3828, Sep. 1989.

Georg–Fries et al. "Analysis of Proteins, Helper Dependence, and Seroepidemiology of a New Human Parvovirus" *Virology* 134:64–71, 1984.

* cited by examiner

ALIGNMENT OF TWO NUCLEOTIDE SEQUENCES.

THE TWO SEQUENCES TO BE ALIGNED ARE:

AAV2CG.
TOTAL NUMBER OF BASES: 4679.

AAV5CG.TOTAL NUMBER OF BASES: 4652.

OPEN GAP COST: 10
UNIT GAP COST: 12

THE CHARACTER TO SHOW THAT TWO ALIGNED RESIDUES ARE IDENTICIAL IS ":"

```
AAV2CG - TTGGCCACTCCCTCTCTGCGCGCTCGCTCGCTCACTGA-------GGCCCGGGCGA -48
         : :  : :::::  :     ::::  ::::::::::: :::       ::  ::: :
AAV5CG - TGGCACTCTCCCCCCTGTCGCGTTCGCTCGCTCGCTGGCTCGTTTGGGGGGGTGG -55

AAV2CG - C----CAAAGGTC-GCCCGACGCCCGGGCTTTGCCCGG-GCGGCCTCA------- -90
         :     ::::: : :::  :::: : : ::  ::  :::  ::  :: ::
AAV5CG - CAGCTCAAAGAGCTGCCAGACGACGGCCCTCTGGCCGTCGCCCCCCCAAACGAGC -110

AAV2CG - --GTGAGCGAGCGAGCGCG-CAGAGAGG-GAGTGGCCAACTCCATCACTAGGGGT -141
           : :::::::::: ::::  :::  ::  ::  :::::  :  ::    : :::::
AAV5CG - CAGCGAGCGAGCGAACGCGACAGGGGGGAGAGTGCCACACTCTCAAGCAAGGGGG -165

AAV2CG - TCCTGGAGGG-GTGGAGTCGTGACG-TGAATTACGTCATAGGGTTAGGGAGGTCC -194
         :  :: : :  :::   :::  : : ::  : : :: : ::::  :   : :::  :
AAV5CG - TTTTGTAAGCAGTGATGTCATAATGATGTAATGCTTATTGTCACGCGATAGTTAA -220

AAV2CG - TGTATTAGAGGTCACGTGA-GTGTTTTGCGACATTTTGCGACACC------ATGT -242
         ::  ::::  ::::  ::::   ::::::::    ::   ::  :         :::
AAV5CG - TG-ATTAACAGTCATGTGATGTGTTTTATCCAATAGGAAGAAAGCGCGCGTATGA -274

AAV2CG - GGTCACGCT---------GGGTATTTAAGCCCGAGTGAGCACGCAGGGTCTCCAT -288
         : :: :::         ::::::  ::: :::::::::: :  ::  :  ::::
AAV5CG - GTTCTCGCGAGACTTCCGGGGTATAAAAGACCGAGTGAACGAGCCCGC-CGCCAT -328

AAV2CG - T-TTGAAGCGGGAG-GTTTGAACGCGCA-GCCGCCATGCCGGGGTTTTACGAGAT -340
         : ::    :  :::   : : ::  : :  :: :::::::  :   ::  :: :: :
AAV5CG - TCTTTGCTCTGGACTGCTAGAGGACCCTCGCTGCCATGGCTACCTTCTATGAAGT -383
```

FIG. 4A

```
AAV2CG  -  TGTGATTAAGGTCCCCAGCGACCTTGACGGGCATCTGCCCGGCATTTCTGACAGC  -395
             :  ::   :::::       :::  :  ::  :   :::::::::  ::  ::::::::::::
AAV5CG  -  CATTGTTCGCGTCCCATTTGACGTGGAGGAACATCTGCCTGGAATTTCTGACAGC  -438

AAV2CG  -  TTTGTGAACTGGGTGGCCGAGAAGGAATGGGAGTTGCCGCCAGATTCTGACATGG  -450
           ::::::  ::::::::    :  :      :      ::::::   ::::  :::::  ::  ::    :
AAV5CG  -  TTTGTGGACTGGGTAACTGGTCAAATTTGGGAGCTGCCTCCAGAGTCAGATTTAA  -493

AAV2CG  -  ATCTGAATCTGATTGAGCAGGCACCCCTGACCGTGGCCGAGAAGCTGCAGCGCGA  -505
           ::  :::  ::::  ::::  :::  :  :      ::::  :::::  ::   :    :  :    ::::
AAV5CG  -  ATTTGACTCTGGTTGAACAGCCTCAGTTGACGGTGGCTGATAGAATTCGCCGCGT  -548

AAV2CG  -  CTTTCTGACGGAATGGCGCCGTGTGAGTAAGGCCCCGGAGGCCCTTTTCTTTGTG  -560
           ::  :::    ::  :::    :      :      :::    :  ::::  ::    ::::::::::
AAV5CG  -  GTTCCTGTACGAGTGGAACAAATTTTCCAAG---CAGGAGTCCAAATTCTTTGTG  -600

AAV2CG  -  CAATTTGAGAAGGGAGAGAGCTACTTCCACATGCACGTGCTCGTGGAAACCACCG  -615
           ::  ::::::  ::::::           ::  ::  ::   :::::   :::   :::::   :::  :::
AAV5CG  -  CAGTTTGAAAAGGGATCTGAATATTTTCATCTGCACACGCTTGTGGAGACCTCCG  -655

AAV2CG  -  GGGTGAAATCCATGGTTTTGGGACGTTTCCTGAGTCAGATTCGCGAAAAACTGAT  -670
           :   :    :::::::::   :  ::  ::  :  :::::::::::::::     :   :::   :
AAV5CG  -  GCATCTCTTCCATGGTCCTCGGCCGCTACGTGAGTCAGATTCGCGCCCAGCTGGT  -710

AAV2CG  -  TCAGAGAATTTACCGCGGGATCGAGCCGACTTTGCCAAACTGGTTCGCGGTCACA  -725
             :           :   :  ::    ::  ::  ::  ::       :            :::::  ::::    ::::
AAV5CG  -  GAAAGTGGTCTTCCAGGGAATTGAACCCCAGATCAACGACTGGGTCGCCATCACC  -765

AAV2CG  -  AAGACCAGAAATGGCGCCGGAGGCGGGAACAAGGTGGTGGATGAGTGCTACATCC  -780
           :::     :  ::  :::     ::::  :     ::  ::::::::::::     :  ::  ::  :
AAV5CG  -  AAGGTAAAGAAGGGC---GGAGCC---AATAAGGTGGTGGATTCTGGGTATATTC  -814

AAV2CG  -  CCAATTACTTGCTCCCCAAAACCCAGCCTGAGCTCCAGTGGGCCGTGGACTAATAT  -835
           ::         :::  ::::  ::  ::      :::  ::  :::::  ::::::::::::::  ::   :
AAV5CG  -  CCGCCTACCTGCTGCCGAAGGTCCAACCGGAGCTTCAGTGGGCGTGGACAAACCT  -869

AAV2CG  -  GGAACAGTATTTAAGCGCCTGTTTGAATCTCACGGAGCCGTAAACGGTTGGTGGCG  -890
           :::  :::::   :      :::   :::::::   ::::::   ::::::  ::::::   :  ::  :::
AAV5CG  -  GGACGAGTATAAATTGGCCGCCCTGAATCTGGAGGAGCGCAAACGGCTCGTCGCG  -924
```

FIG.4B

```
AAV2CG - CAGCATCTGACGCACGTGTCGCAGACGCAGGAGCAGAACAAAGAGAATCAGAATC -945
         :::  ::::  :  :        ::::::: :::   :  :::  :         :::    :
AAV5CG - CAGTTTCTGGCAGAATCCTCGCAG-CGCTCG--CAGGAGGCGGCTTCGCAGCGTG -976

AAV2CG - CCAATTCTGATGCGCCGGTGATCAGATCAAAAACTTCAGCCAGGTACATGGAGCT -1000
         ::  :  ::  :::::  ::::  ::::   :     ::  ::::::        :   ::::::::  :::
AAV5CG - AGTTCTCGGCTGACCCGGTCATCAAAAGCAAGACTTCCCAGAAATACATGGCGCT -1031

AAV2CG - GGTCGGGTGGCTCGTGGACAAGGGGATTACCTCGGAGAAGCAGTGGATCCAGGAG -1055
         :::        :::::::::::   :  ::  ::  ::  :::::::::::::::::::::
AAV5CG - CGTCAACTGGCTCGTGGAGCACGGCATCACTTCCGAGAAGCAGTGGATCCAGGAA -1086

AAV2CG - GACCAGGCCTCATACATCTCCTTCAATGCGGCCTCCAACTCGCGGTCCCAAATCA -1110
         :  :::::       :::   :::::::::::     :   ::   ::::::  :::    :::  ::::
AAV5CG - AATCAGGAGAGCTACCTCTCCTTCAACTCCACCGGCAACTCTCGGAGCCAGATCA -1141

AAV2CG - AGGCTGCCTTGGACAATGCGGGAAAGATTATGAGCCTGACTAAAACCGCCCCCGA -1165
         ::::  ::   :  ::::: :::        ::  :::::::::  ::::   ::::  :::      ::
AAV5CG - AGGCCGCGCTCGACAACGCGACCAAAATTATGAGTCTGACAAAAAGCGCGGTGGA -1196

AAV2CG - CTACCTGGTGGGCCAGCAGCCCGTG-GAGGACATTTCCAGCAATCGGATTTATAA -1219
         ::::::  :::::   :::    :         ::::::::::::  :  ::   :  :::    :    :
AAV5CG - CTACCTCGTGGGG-AGCTCCGTTCCCGAGGACATTTCAAAAAACAGAATCTGGCA -1250

AAV2CG - AATTTTGGAACTAAACGGGTACGATCCCCAATATGCGGCTTCCGTCTTTCTGGGA -1274
         ::::::: ::   : ::: ::  :::::: ::    :: ::::   :::  :: :           ::
AAV5CG - AATTTTTGAGATGAATGGCTACGACCCGGCCTACGCGGGATCCATCCTCTACGGC -1305

AAV2CG - TGGGCCACGAAAAAGTTCGGCAAGAGGAACACCATCTGGCTGTTTGGGCCTGCAA -1329
         :::    :    :::  ::::::::::::: :::::::  :   ::  ::  ::  :
AAV5CG - TGGTGTCAGCGGCTCCTTCAACAAGAGGAACACCGTCTGGCTCTACGGACCCGCCA -1360

AAV2CG - CTACCGGGAAGACCAACATCGCGGAGGCCATAGCCCACACTGTGCCCTTCTACGG -1384
         :  :::::  :::::::::::::::::::::::   ::::::::::::::::::::     :::::
AAV5CG - CGACCGGCAAGACCAACATCGCGGAGGCCATCGCCCACACTGTGCCCTTTTACGG -1415

AAV2CG - GTGCGTAAACTGGACCAATGAGAACTTTCCCTTCAACGACTGTGTCGACAAGATG -1439
         :::::   ::::::::::::::   ::::::::::  :::::::::  :::::::::   :::::  :::
AAV5CG - CTGCCTGAACTGGACCAATGAAAAACTTTCCCTTTAATGACTGTGTGGACAAAATG -1470
```

FIG.4C

```
AAV2CG - GTGATCTGGTGGGAGGAGGGGAAGATGACCGCCAAGGTCGTGGAGTCGGCCAAAG -1494
         : ::  :::::::::::::::  ::::::::::  ::::::  :: ::  ::  ::::: :
AAV5CG - CTCATTTCGTGGGAGGAGGGAAAGATGACCAACAAGGTGGTTGAATCCGCCAAGG -1525

AAV2CG - CCATTCTCGGAGGAAGCAAGGTGCGCGTGGACCAGAAATGCAAGTCCTCGGCCCA -1549
         ::::  ::  :: ::           ::::::::: ::  ::  ::::::::::: ::    ::::: :  ::
AAV5CG - CCATCCTGGGGGGCTCAAAGGTGCGGGTCGATCAGAAATGTAAATCCTCTGTTCA -1580

AAV2CG - GATAGACCCGACTCCCGTGATCGTCACCTCCAACACCAACATGTGCGCCGTGATT -1604
         ::  ::   : ::  :: ::  :: :: ::::: ::  ::::::::::  :  ::: :
AAV5CG - AATTGATTCTACCCCTGTCATTGTAACTTCCAATACAAACATGTGTGTGGTGGTG -1635

AAV2CG - GACGGGAACTCAACGACCTTCGAACACCAGCAGCCGTTGCAAGACCGGATGTTCA -1659
         ::  :::::  ::  :::::::::: ::::::::::::::::::  ::  :  :::::  :::::::
AAV5CG - GATGGGAATTCCACGACCTTTGAACACCAGCAGCCGCTGGAGGACCGCATGTTCA -1690

AAV2CG - AATTTGAACTCACCCGCCGTCTGGATCATGACTTTGGGAAGGTCACCAAGCAGGA -1714
         :::::::::: ::     :: ::      :  :: ::::: :::  :  ::  :::::::::
AAV5CG - AATTTGAACTGACTAAGCGGCTCCCGCCAGATTTTGGCAAGATTACTAAGCAGGA -1745

AAV2CG - AGTCAAAGACTTTTTCCGGTGGGCAAAGGATCACGTGGTTGAGGTGGAGCATGAA -1769
         :::::: ::::::::: :      :::::::::::     :   :::      ::::    ::  ::
AAV5CG - AGTCAAGGACTTTTTTGCTTGGGCAAAGGTCAATCAGGTGCCGGTGACTCACGAG -1800

AAV2CG - TTCTACGTCAAAAAGGG--TGGAGCCAAGAAAAGACCCGCCCCCAGTGACGCAGA -1822
         ::  : ::    :  ::     :::   : ::   ::::  :: :           : ::
AAV5CG - TTTAAAGTTCCCAGGGAATTGGCGGGAACTAAAGGGGCG------GAGAAATCTC -1849

AAV2CG - TATAAGTGAGCCCAAACGGGTGCGCGAGTCAGTTGCGCAGCCATCGACGTCAGAC -1877
         ::  ::    :::::   :::::   ::  :     : :   ::: ::    : :::    :         ﹨
AAV5CG - TAAAAC---GCCCACT-GGGTGA-CGTCACCAATACT-AGCTATAAAAGTCTGGA -1898

AAV2CG - GCGGAAGCTTCGATCAACTACGCAGACAGGTACCAAAACAAAT-GTTCTCGTCAC -1931
         :    ::::  :   ::    : :::    : :::: ::    ::  :   :     ::
AAV5CG - G---AAGC--GGGCCAGGCTCTCATTT-GTTCCCGAGACGCCTCGCAGTTCAGAC -1947

AAV2CG - GTGGGCATGAATCT-GATGCTGTTTCCCTGCAGACAATGCGAGAGAATGAATCAG -1985
         :::   :   :::  : ::::: :   : :: :  :  ::::   ::  ::  ::   :
AAV5CG - GTGACTGTTGATCCCGCTCCTCTGCGACCGCTCA-ATTGGAATTCAAGGTAT--G -1999
```

FIG.4D

```
AAV2CG - AATTCAAATATCTGCTTCACTCACGGACAGAAAGACTGTTTAGAGTGCTTTCCCG  -2040
          : : :::::  ::  : : :::  ::   :::     : : : ::   :
AAV5CG - ATTGCAAATG--TGACT-A-TCATGCTCAATTTGACA----ACATTTCTAACAAA  -2046

AAV2CG - TGTCA-GAATCTCAACCCGTTTCTGTCGTCAAAAAGGC--GTATCAGAAACTGTG  -2092
          ::: :  ::::  :: :   :   :  ::::::  :  ::::: :  ::   ::
AAV5CG - TGTGATGAATGTGAATATTTGAATCGGGGCAAAAATGGATGTATCTGTCACAATG  -2101

AAV2CG - CTACATTCA-TCATAT----CATGGAAAGGTGCCAGACGCTTGCACTGCCTGCG  -2142
          ::       : :::  ::   :::::::     :: :     : :    : :::
AAV5CG - TAACTCACTGTCAAATTTGTCATGGGATTCCCCCCTGGGAAAAGGAAAACTTG-- -2154

AAV2CG - ATCTGGTCAATGTGGATTTGGATGACTGCATCTTTGAACAATAAATGATTTAAAT  -2197
          ::  :       :: ::::::: :: ::   ::       ::::: ::::: :       : :
AAV5CG - -TCAGATTT-TGGGGATTTTGACGATGCCAATAAAGAACAGTAAATAAAGCGAGT  -2207

AAV2CG - CAGGTATGGCTGCCGATGGTTATCTTCCAGATTGGCTCGAGGACACTCTCTCTGA  -2252
          ::  ::: ::    : ::: :  :::::::::::: : ::: ::   :      :::
AAV5CG - -AGTCATGTCTTTTGTTGATCACCCTCCAGATTGGTTGGAAGAAGTTGG---TGA  -2258

AAV2CG - AGGAATAAGACAGTGGTGGAAGCTCAAACCTGGCCCACCACCACCAAAGCCCGCA  -2307
          :::   :   :   :::  : :   :: :: : :::::::::     ::::::: :::
AAV5CG - AGGTCTTCGCGAGTTTTTGGGCCTTGAAGCGGGCCCACCGAAACCAAAACCCAAT  -2313

AAV2CG - GAGCGGCATAAGGACGACAGCAGGGGTCTTGTGCTTCCTGGGTACAAGTACCTCG  -2362
          ::: :::: : ::   :  : : ::::::::::: ::::: :: :: :: ::::
AAV5CG - CAGCAGCATCAAGATCAAGCCCGTGGTCTTGTGCTGCCTGGTTATAACTATCTCG  -2368

AAV2CG - GACCCTTCAACGGACTCGACAAGGGAGAGCCGGTCAACGAGGCAGACGCCGCGGC  -2417
          :::::   :::::  :::::  ::::::::: :::::: ::::::::::  :   ::
AAV5CG - GACCCGGAAACGGTCTCGATCGAGGAGAGCCTGTCAACAGGGCAGACGAGGTCGC  -2423

AAV2CG - CCTCGAGCACGACAAAGCCTACGACCGGCAGCTCGACAGCGGAGACAACCCGTAC  -2472
          :  ::::::::::  :  ::: ::  ::::::: ::          :::::::::::  :::
AAV5CG - GCGAGAGCACGACATCTCGTACAACGAGCAGCTTGAGGCGGGAGACAACCCCTAC  -2478

AAV2CG - CTCAAGTACAACCACGCCGACGCGGAGTTTCAGGAGCGCCTTAAAGAAGATACGT  -2527
          :::::::::::::::::::: :::::::::::::::::::  ::   :: :: :: :
AAV5CG - CTCAAGTACAACCACGCGGACGCCGAGTTTCAGGAGAAGCTCGCCGACGACACAT  -2533
```

FIG.4E

```
AAV2CG  -  CTTTTGCGGGCAACCTCGGACGAGCAGTCTTCCAGGCGAAAAAGAGGGTTCTTGA  -2582
           : ::  ::::: ::::::::::   :::::::::  :::::  ::  ::  :::::::::  ::
AAV5CG  -  CCTTCGGGGGAAACCTCGGAAAGGCAGTCTTTCAGGCCAAGAAAAGGGTTCTCGA  -2588

AAV2CG  -  ACCTCTGGGCCTGGTTGAGGAACCTGTTAAGACGGCTCCGGGAAAAAAGAGGCCG  -2637
           ::::  :  :::::::::::::  ::  ::::::::::  ::        ::::  ::
AAV5CG  -  ACCTTTTGGCCTGGTTGAAGAGGGTGCTAAGACGGCCCCTACCGGAAAGCGGATA  -2643

AAV2CG  -  GTAGAGCACTCTCCTGTGGAGCCAGACTCCTCCTCGGGAACCGGAAAGGCGGGCC  -2692
           :  ::  ::::  :::   ::   :::   :::          :::  :::  :  :::    ::
AAV5CG  -  GACGACCACTTTCCAAAA-AGAAAGAAGGCTC----GGA-CCGAAGAGGACT-CC  -2691

AAV2CG  -  AGCAGCCTGCAAGAAAAAGATTGAATTTTGGTCAGACTGGAGACGCAG-ACTCAG  -2746
           :  ::::::  : :                    : ::::::::: : ::   ::  : ::  :::
AAV5CG  -  A--AGCCTTCCACC--------------TCGTCAGAC-GCCGAAGCTGGACCCAG  -2729

AAV2CG  -  TACCTGACCCCCAGCCTCTCGGACAGCCACCAGCAGCCCCCTCTGGTCTGGGAAC  -2801
           :  ::  :::  :::  ::         :  :::  :      : :    ::::  ::  :::::  :
AAV5CG  -  ---CGGATCCC-AGCAGCTGCAAATCCCAGCCCAACCAGCCTCAAGTTTGGGAGC  -2780

AAV2CG  -  TAATACGATGGCTACAGGCAGTGGCGCACCAATGGCAGACAATAACGAGGGCGCC  -2856
           :  ::::  :::  ::  : ::   ::::::   :::  :::     ::::::::::  : ::  :::
AAV5CG  -  TGATACAATGTCTGCGGGAGGTGGCGGCCCATTGGGCGACAATAACCAAGGTGCC  -2835

AAV2CG  -  GACGGAGTGGGTAATTCCTCGGGAAATTGGCATTGCGATTCCACATGGATGGGCG  -2911
           ::  :::::::::  :::  ::::::::  :::::::::::::::::::  :::::::::  :
AAV5CG  -  GATGGAGTGGGCAATGCCTCGGGAGATTGGCATTGCGATTCCACGTGGATGGGG  -2890

AAV2CG  -  ACAGAGTCATCACCACCAGCACCCGAACCTGGGCCCTGCCCACCTACAACAACCA  -2966
           :::::::::  :::::::           ::::::::::::::::        :::::::  :::::::::::::
AAV5CG  -  ACAGAGTCGTCACCAAGTCCACCCGAACCTGGGTGCTGCCCAGCTACAACAACCA  -2945

AAV2CG  -  CCTCTACAAACAAATTTCCAGCCAATCAGGAGCCTCGA---ACGACAATCACTAC  -3018
           ::  :::  : :  ::   :::   ::  : :   :   :    ::: :::      ::::
AAV5CG  -  CCAGTACCGAGAGATCAAAAGCGGCTCCGTCGACGGAAGCAACGCCAACGCCTAC  -3000

AAV2CG  -  TTTGGCTACAGCACCCCTTGGGGGTATTTTGACTTCAACAGATTCCACTGCCACT  -3073
           :::::  ::::::::::::  :::::::::  :::::::::::  :  :::::::  :::::::
AAV5CG  -  TTTGGATACAGCACCCCCTGGGGGTACTTTGACTTTAACCGCTTCCACAGCCACT  -3055
```

FIG. 4F

```
AAV2CG - TTTCACCACGTGACTGGCAAAGACTCATCAACAACAACTGGGGATTCCGACCCAA -3128
         ::  ::  :::::::::::::::::::::::::: ::::::: ::: :::::
AAV5CG - GGAGCCCCCGAGACTGGCAAAGACTCATCAACAACTACTGGGGCTTCAGACCCCG -3110

AAV2CG - GAGACTCAACTTCAAGCTCTTTAACATTCAAGTCAAAGAGGTCACGCAGAATGAC -3183
         :   ::::    ::::    ::::  :::::::::::::::::::: : : :::
AAV5CG - GTCCCTCAGAGTCAAAATCTTCAACATTCAAGTCAAAGAGGTCACGGTGCAGGAC -3165

AAV2CG - GGTACGACGACGATTGCCAATAACCTTACCAGCACGGTTCAGGTGTTTACTGACT -3238
         ::  ::  ::  :: :::::  :::::  :::  :: ::  :::::::::: :::
AAV5CG - TCCACCACCACCATCGCCAACAACCTCACCTCCACCGTCCAAGTGTTTACGGACG -3220

AAV2CG - CGGAGTACCAGCTCCCGTACGTCCTCGGCTCGGCGCATCAAGGATGCCTCCCGCC -3293
         : ::::::::: :: :::::: :::::  : :       : ::::::::: ::: :
AAV5CG - ACGACTACCAGCTGCCCTACGTCGTCGGCAACGGGACCGAGGGATGCCTGCCGGC -3275

AAV2CG - GTTCCCAGCAGACGTCTTCATGGTGCCACAGTATGGATACCTCACCCTGAACAAC -3348
         :::::  :   : : ::::::  : :: ::::: ::: ::   ::: ::::::  :
AAV5CG - CTTCCCTCCGCAGGTCTTTACGCTGCCGCAGTACGGTTACGCGACGCTGAACCGC -3330

AAV2CG - GGGAGT-CAGGCAGTAGGAC---GCTCTTCA--TTTTACTGCCTGGAGTACTTTC -3397
         :  :   :::  : :   ::    :: :: :  ::::::::::::::::::::::
AAV5CG - GACAACACAGAAAATCCCACCGAGAGGAGCAGCTTCTTCTGCCTAGAGTACTTTC -3385

AAV2CG - CTTCTCAGATGCTGCGTACCGGAAACAACTTTACCTTCAGCTACACTTTTGAGGA -3452
         :        ::::::::  : :: ::  :::::::::: ::  : :::::: ::::::
AAV5CG - CCAGCAAGATGCTGAGAACGGGCAACAACTTTGAGTTTACCTACAACTTTGAGGA -3440

AAV2CG - CGTTCCTTTCCACAGCAGCTACGCTCACAGCCAGAGTCTGGACCGTCTCATGAAT -3507
         :: :: :::::::  ::::: :::::::::: :::  ::::::  :   ::   ::
AAV5CG - GGTGCCCTTCCACTCCAGCTTCGCTCCCAGTCAGAACCTGTTCAAGCTGGCCAAC -3495

AAV2CG - CCTCTCATCGACCAGTACCTGTATTACTT---GAGCAGAACAAACACTC------ -3553
         ::  ::  : :::::::::: ::::  :::   :::::::: ::  ::::::
AAV5CG - CCGCTGGTGGACCAGTACTTGTACCGCTTCGTGAGCACAAATAACACTGGCGGAG -3550

AAV2CG - -CAAGTGGAACCACCAC---GCAGTCA-AGGCTTCAGTT--TTCTCAGGCCGGAG -3601
         : :::  :::  :  ::    ::::: :  : :    :    :  :  :   ::
AAV5CG - TCCAGTTCAACAAGAACCTGGCCGGGAGATACGCCAACACCTACAAAAACTGGTT -3605
```

FIG.4G

```
AAV2CG - CGAGTGACATTCGGGACCAGTCTAGGAACTGGCTTCCTGGACCCTGTTACCGCCA -3656
          :  :  :      ::: :  :  :::  ::::   :::::  : : :        : :
AAV5CG - CCCGGGGCCCATGGGCCGAACCCAGGG-CTGGAA-CCTGGGCTCCGGGGTCAACC -3658

AAV2CG - GCAGCGAGTATCAAAGACATCTGCGGATAACAACAACAGTGAATACTCGTGGACT -3711
         ::  :: :::  :::   : : :: ::      :  ::: :  :  ::  ::::  :: :
AAV5CG - GC-GCCAGTGTCAGCGCCTTC-GCCACGACCAATAGGA-TGGAG-CTCGAGGGCG -3709

AAV2CG - GGAGCTACCAAGTACCACCTCAATGGCAGAGACTCTCTGGTGAATCCGGGCCCGG -3766
          :;: ::::: :: :: :: ::     :: :: ::    ::   ::      :: ::
AAV5CG - CGAGTTACCAGGTGCCCCCGCA---GCCGA-ACGGCATGACCAACAACCTCCAGG -3760

AAV2CG - CCATGGCAAGCCACAAGGACGATGAAGAAAAGTTTTTTCCTCAGAGCGGGGTTCT -3821
          ::   ::::    :::        :    :  :: ::::   :  :: :::    :    :
AAV5CG - GCA--GCAA--CACCTATGCCCTGGAGAACACTATGATCTTCAA--CAG----C- -3804

AAV2CG - CATCTTTGGGAAGCAAGGCTCAGAGAAAACAAATGTGGACATTGAAAAGGTCATG -3876
         ::  :       :  ::::   :      :::  :         ::     :  :    :  :  : ::::
AAV5CG - CAGCCG-GCGAACCCGGGCACCACCGCCACGTACCTCGAGGGCAACATGCTCATC -3858

AAV2CG - ATTACAGACGAAGAGGAAATCAGGACAACCAATCCCGTGGC-TACGGAGCAGTAT -3930
          :   ::: :::     :: :         : :          ::  :::::: :::    :  :
AAV5CG - AC--CAG-CGAGAGCGAGACGCAGCCGGTGAACCGCGTGGCGTACAACGTCGGCG -3910

AAV2CG - GGTTCTGTATCTACCAACCTCCAGAGAGGCAACAGACAAGCAGCTACCGCAGATG -3985
         ::         :   : :::::::  :::::::   :: ::         : :::   ::::
AAV5CG - GGCAGA-TGGCCACCAACAACCAGAGCTCCACCACTGCCCCCGCGACCGGCACGT -3964

AAV2CG - TCAACACACAAGGCGTTCTTCCAGGCATGGTCTGGCAGGACAGAGATGTGTACCT -4040
         ::::   :: :    :   : :: ::::  ::  :::   ::: ::  ::  :: :::::::::
AAV5CG - ACAACCTCCAGGAAATCGTGCCCGGCAGCGTGTGGATGGAGAGGGACGTGTACCT -4019

AAV2CG - TCAGGGGCCCATCTGGGCAAAGATTCCACACACGGACGGACATTTTCACCCCTCT -4095
         ::  ::  :::::::::::: ::::::   :::  :  ::::  :  :: :::::::::::::
AAV5CG - CCAAGGACCCATCTGGGCCAAGATCCCAGAGACGGGGGCGCACTTTCACCCCTCT -4074

AAV2CG - CCCCTCATGGGTGGATTCGGACTTAAACACCCTCCTCCACAGATTCTCATCAAGA -4150
         ::   ::::::  :::::::::::: :::::::::  :: ::      :::  ::::::::::
AAV5CG - CCGGCCATGGGCGGATTCGGACTCAAACACCCACCGCCCATGATGCTCATCAAGA -4129
```

FIG.4H

```
AAV2CG - ACACCCCGGTACCTGCGAATCCTTCGACCACCTTCAGTG-CGGCAAAGTTTGCTT  -4204
         ::::  ::  ::  ::  :    :::     ::  ::::  ::::    :  ::      ::  ::
AAV5CG - ACACGCCTGTGCCCGGAAATA--TC-ACCAGCTTCTCGGACGTGCCCGTCAGCAG  -4181

AAV2CG - CCTTCATCACACAGTACTCCACGGGACAGGTCAGCGTGGAGATCGAGTGGGAGCT  -4259
         :  :::::::::  ::::::    :::  ::  ::::::::  ::::::::::  ::::::::::::
AAV5CG - C-TTCATCACCCAGTACAGCACCGGGCAGGTCACCGTGGAGATGGAGTGGGAGCT  -4235

AAV2CG - GCAGAAGGAAAACAGCAAACGCTGGAATCCCGAAATTCAGTACACTTCCAACTAC  -4314
         ::::::::::::   :::  :  :::::: :: ::  ::  ::::::::::       :::::::
AAV5CG - CAAGAAGGAAAACTCCAAGAGGTGGAACCCAGAGATCCAGTACACAAACAACTAC  -4290

AAV2CG - AACAAGTCTGTTAATGTGGACTTTACTGTGGACACTAATGGCCGTGTATTCAGAGC  -4369
         :::  :  :            :::::::::::  :      ::::::  :  ::  :     ::  ::::  :
AAV5CG - AACGACCCCCAGTTTGTGGACTTTGCCCCGGACAGCACCGGGGA--ATACAGAAC  -4343

AAV2CG - CTC--GCCCCATTGGCACCAGATACCTGACTCGTAATCTGTAAT---TGCTTGT-  -4418
         :  :   :  ::  ::  ::  :::  :::::::  ::  ::     ::  :::      :  :  :::
AAV5CG - CACCAGACCTATCGGAACCCGATACCTTACCCGACCCCTTTAACCCATTCATGTC  -4398

AAV2CG - ---TAA--TCAATAAACCGTTTAATTCGTTTCAGTTGAACTTTGG-TCTCTGCGT  -4467
            ::     ::::::::::::  ::  :::::  :::::  ::     ::      :::         ::
AAV5CG - GCATACCCTCAATAAACCGTGTA-TTCGTGTCAGTAAAATACTGCCTCTTGTGGT  -4452

AAV2CG - ATTTCTTTCT-TATCTAGTTTCCATGGCTACGTAGATAAGTAGCATGGCGGGTTA  -4521
         :::  :     ::  :       ::  :  :     ::::  :           :  ::  ::    :  ::
AAV5CG - CATTCAATGAATAACAGCTTACAACATCTACAAAACCTCCTTGCTTGA-GAGTGT  -4506

AAV2CG - ATCATTAACTACAAGGAACCCCTAGTGATGGAGTTGGCCACTCCCTC-TCTGCGC  -4575
         ::  :   :::  :             ::   :::::  :  :  ::     :::  :  ::  :
AAV5CG - GGCACT--CTCCCC----CCTGTCGCGTTCGC-TCGCTCGCTGGCTCGTTTGGGG  -4554

AAV2CG - GCTCGCTCGCTCACTGAG--GCCGGGCGACCAAAGGTCGCCCGACGCCCGGGCTT  -4628
         :    :    :::::  :::     :::  :  ::::            :  :::   :::::
AAV5CG - GGGTGGCAGCTCAAAGAGCTGCCAGACGACGGCCCTCTGGCCGTCGCCCC-----  -4604

AAV2CG - TGCCCGGGCGGCCTCAGTGAGCGAGCGAGCGCGCAGAGAGGGAGTGGCCAA      -4679
         :::     ::  ::   :  :::  ::::::::::  ::::       :  :::::::  :    :  :
AAV5CG - --CCCAAACGAGC-CAGCGAGCGAGCGAACGCGACAGGGGGGAGAGTGCCA-    -4652
```

FIG. 41

Identity    : 3013 (64.77%)
Number of gaps inserted in AAV2CG: 43
Number of gaps inserted in AAV5CG: 63

FIG.4J

ALIGNMENT OF TWO PROTEIN SEQUENCES.

The two sequences to be aligned are:

AAV2VPI.
DE VPI
OS AAV2
Total number of residues: 735.

AAV5VP1.
DE AAV5VP1
OS AAV5VP1
Total number of residues: 724. 2101-4272

Comparison matrix : Structure-genetic matrix.
Open gap cost: 8
Unit gap cost: 5

The character to show that two aligned residues are identical is ':'
The character to show that two aligned residues are similar is '.'
Amino acids said to be 'similar' are: A,S,T; D,E; N,Q; R,K; I,L,M,V; F,Y,W

```
AAV2VP1 - MAADGYLPDWLEDTLSEGIRQWWKLKPGPPPPKPAERHKDDSRGLVLPGYKYLGP -55
           :.      :::::. . ::.: . .  :  ::: :::    : : .:::::::: ::::
AAV5VP1 - MSFVDHPPDWLEE-VGEGLREFLGLEAGPPKPKPNQQHQDQARGLVLPGYNYLGP -54

AAV2VP1 - FNGLDKGEPVNEADAAALEHDKAYDRQLDSGDNPYLKYNHADAEFQERLKEDTSF -110
           ::::..:::::  ::  : :::  .:  ::...:::::::::::::::.: .::::
AAV5VP1 - GNGLDRGEPVNRADEVAREHDISYNEQLEAGDNPYLKYNHADAEFQEKLADDTSF -109

AAV2VP1 - GGNLGRAVFQAKKRVLEPLGLVEEPVKTAPGKKRPVEHSPVEPDSSSGTGKAGQQ -165
           :::::.::::::::::::: :::::   ::::   ::  .: :          . :
AAV5VP1 - GGNLGKAVFQAKKRVLEPFGLVEEGAKTAPTGKRIDDHFPKR--KKARTEEDSKP -162

AAV2VP1 - PARKRLNFGQTGDADSVPDPQPLGQPPAAPSGLGTNTMATGSGAPMADNNEGADG -220
            .           .      : : :     : ::. ::...: : :. ::: ::::
AAV5VP1 - STS-------SDAEAGPSGSQQLQIPAQPASSLGADTMSAGGGGPLGDNNQGADG -210
```

FIG.5A

```
AAV2VP1 - VGNSSGNWHCDSTWMGDRVITTSTRTWALPTYNNHLYKQISSQSG-ASNDNHYFG -274
          :::.::  ::::::::::::.: :::::  ::.:::: :. : : :   :: : :::
AAV5VP1 - VGNASGDWHCDSTWMGDRVVTKSTRTWVLPSYNNHQYREIKSGSVDGSNANAYFG -265

AAV2VP1 - YSTPWGYFDFNRFHCHFSPRDWQRLINNNWGFRPKRLNFKLFNIQVKEVTQNDGT -329
          :::::::::::::::: :.::::::::::::: ::::::. : : ::::::::::::..: :
AAV5VP1 - YSTPWGYFDFNRFHSHWSPRDWQRLINNYWGFRPRSLRVKIFNIQVKEVTVQDST -320

AAV2VP1 - TTIANNLTSTVQVFTDSEYQLPYVLGSAHQGCLPPFPADVFMVPQYGYLTLNNGS -384
          ::::::::::::::::::  .:::::::.:    ::::  ::  ::  .::::: :::
AAV5VP1 - TTIANNLTSTVQVFTDDDYQLPYVVGNGTEGCLPAFPPQVFTLPQYGYATLNRDN -375

AAV2VP1 - Q--AVGRSSFYCLEYFPSQMLRTGNNFTFSYTFEDVPFHSSYAHSQSLDRLMNPL -437
          :::::.:::::::: :::::::::: :.: ::.::::::::.: :: : .: :::
AAV5VP1 - TENPTERSSFFCLEYFPSKMLRTGNNFEFTYNFEEVPFHSSFAPSQNLFKLANPL -430

AAV2VP1 - IDQYLYYLSRTNTPSGTTTQSRLQFSQAGASDIRDQSRNWLPGPCYRQQRVSKTS -492
          .:::::  ::    :  .::   :   .:: :::  ::  : :
AAV5VP1 - VDQYLYRFVSTNNTGG------VQFNKNLAGRYANTYKNWFPGPMGRTQGWNLGS -479

AAV2VP1 - ADNNNSEYSWTGATKYHLNGRDSLVNPGPAMASHKDDEEKFFPQSGVLIFGKQCS -547
           :  :  ... . : :   :::  .    .     .:: : .
AAV5VP1 - GVNRASVSAFATTNRMELEGASYQVPPQPNGMTNNLQGSNTYALENTMIFNSQPA -534

AAV2VP1 - EKTNVDI---EKVMITDEEEIRTTNPVATEQYGSVSTNLQRGNRQAATADVNTQG -599
           ..:: : :    : ::   : ..:: :       :: : :
AAV5VP1 - NPGTTATYLEGNMLITSESETQPVNRVAYNVGGQMATNNQSSTTAPATGTYNLQE -589

AAV2VP1 - VLPGMVWQDRDVYLQGPIWAKIPHTDGHFHPSPLMGGFGLKHPPPQILIKNTPVP -654
          ..::  ::  .::::::::::: :  :::::: ::::::::::::  .::::::::
AAV5VP1 - IVPGSVWMERDVYLQGPIWAKIPETGAHFHPSPAMGGFGLKHPPPMMLIKNTPVP -644

AAV2VP1 - ANPSTTFSAAKFASFITQYSTGQVSVEIEWELQKENSKRWNPEIQYTSNYNKSVN -709
          :  :..::   .:::::::::::::::.::.:::: :::::::::::::::::: :::
AAV5VP1 - GNI-TSFSDVPVSSFITQYSTGQVTVEMEWELKKENSKRWNPEIQYTNNYNDPQF -698

AAV2VP1 - VDFTVDTNGVYSEPRPIGTRYLTRNL -735
          ::::. :. : :   :::::::::: :
AAV5VP1 - VDFAPDSTGEYRTTRPIGTRYLTRPL -724
```

FIG.5B

Identity:    421 (58.15%)
Similarity: 63 (8.70%)
Number of gaps inserted in AAV2VP1: 3
Number of gaps inserted in AAV5VP1: 5

FIG.5C

ALIGNMENT OF TWO PROTEIN SEQUENCES.

The two sequences to be aligned are:

REP78.
DE REP78
OS AAV
Total number of residues: 621.

AAV5REP.
DE REP
OS AAV5
Total number of residues: 610.

Comparison matrix: Structure-genetic matrix.
Open gap cost: 8
Unit gap cost: 5

The character to show that two aligned residues are identical is ':'
The character to show that two aligned residues are similar is '.'
Amino acids said to be similar are: A,S,T; D,E; N,Q; R,K; I,L,M,V; F,Y,W

```
REP78    - MPGFYEIVIKVPSDLDGHLPGISDSFVNWVAEKEWELPPDSDMDLNLIEQAPLTV  -55
           :  :::....:: :.. ::::::::::  ::.    ::::::.::. : :.:: :::
AAV5REP  - MATFYEVIVRVPFDVEEHLPGISDSFVDWVTGQIWELPPESDLNLTLVEQPQLTV  -55

REP78    - AEKLQRDFLTEWRRVSKAPEALFFVQFEKGESYFHMHVLVETTGVKSMVLGRFLS  -110
           :....  :  ::  ::  .  ::   :. :::::::::   :::..:  :::::..:
AAV5REP  - ADRIRRVFLEWNKFSKRQ-ESKFFVQFEKGSEYFHLHTLVETSGISSMVLGRYVS  -109

REP78    - QIREKLIQRIYRGIEPTLPNWFAVTKTRNGAGGCNKVVDECYIPNYLLPKTQPEL  -165
           :::   :.    .. ::::  . :  : :.::  . :  : :::::   :::  ::::: ::::
AAV5REP  - QIRAQLVKVVFQGIEPQINDWVAITKVKKG--GANKVVDSGYIPAYLLPKVQPEL  -162

REP78    - QWAWTNMEQYLSACLNLTERKRLVAQHLTHVSQTQEQNKENQNPNSDAPVIRSKT  -220
           :::::::..  :    :  ::: ::::::::: :.   :      :       :      :      :  :::::.:::
AAV5REP  - QWAWTNLDEYKLAALNLEERKRLVAQFLA-ESSQRSQEAASQREFSADPVIKSKT  -216

REP78    - SARYMELVGWLVDKGITSEKQWIQEDQASYISFNAASNSRSQIKAALDNAGKIMS  -275
           :  ..::  ::  ::::.  ::::::::::::::  :  ::.:::..  :::::::::::::::   ::::
AAV5REP  - SQKYMALVNWLVEHGITSEKQWIQENQESYLSFNSTGNSRSQIKAALDNATKIMS  -271
```

FIG.6A

```
REP78    - LTKTAPDYLVGQQPVEDISSNRIYKILELNGYDPQYAASVFLGWATKKFGKRNTI -330
           ::::. :::::   ::::  :::. : :..:::::  :: :.   ::   . .:::.
AAV5REP  - LTKSAVDYLVGSSVPEDISKNRIWQIFEMNGYDPAYAGSILYGWCQRSFNKRNTV -326

REP78    - WLFGPATTGKTNIAEAIAHTVPFYGCVNWTNENFPFNDCVDKMVIWWEEGKMTAK -385
           ::.:::::::::::::::::::::::::::::::::::::::.:::::::::::
AAV5REP  - WLYGPATTGKTNIAEAIAHTVPFYGCVNWTNENFPFNDCVDKMLIWWEEGKMTNK -381

REP78    - VVESAKAILGGSKVRVDQKCKSSAQIDPTPVIVTSNTNMCAVIDGNSTTFEHQQP -440
           ::::::::::::::::::::::::: ::: ::::::::::::: :::::::::::
AAV5REP  - VVESAKAILGGSKVRVDQKCKSSVQIDSTPVIVTSNTNMCVVVDGNSTTFEHQQP -436

REP78    - LQDRMFKFELTRRLDHDFGKVTKQEVKDFFRWAKDHVVEVEHEFYVKKGGAKKRP -495
           : :::::::::: .::   :::.:::::::::::::. :::   : : :::.  : .
AAV5REP  - LEDRMFKFELTKRLPPDFGKITKQEVKDFFAWAKVNQVPVTHEFKVPRELAGTK- -490

REP78    - APSDADISEPKRVRESVAQPSTSDAEASINYADRYQNKCSRHVGMNLMLFPVRQC -550
                .        :   .     :  :           .             :
AAV5REP  - GAEKSLKRPLGDVTNTXYKSLEKRARLSFVPETPRSSDVTVDPAPLRPLNWNSRY -545

REP78    - ERMNQNSNICFTHGQKDCLECFPVSESQPVSVVKKAYQKLCYIHHIMGKVPDACT -605
             .     :   : ::   .          :  :       . .
AAV5REP  - DC-KCDYHAQFDNISNKCDECEYLNRGKNGCICHNVTH-CQICHGIPPWEKENLS -598

REP78    - ACDLVNVDLDDCIFEQ -621
           : :::   ::
AAV5REP  - DF----GDFDDANKEQ -610
```

Identity : 355 (58.2%)
Similarity: 56 (9.2%)

Number of gaps inserted in REP78: 0
Number of gaps inserted in AAV5REP : 7

FIG.6B

SEQUENCE LISTING

<160> NUMBER OF SEQ ID NOS: 26

<210> SEQ ID NO 1
<211> LENGTH: 4652
<212> TYPE: DNA
<213> ORGANISM: Artificial Sequence

```
<220> FEATURE:
<223> OTHER INFORMATION: Description of Artificial Sequence:/Note =
      synthetic construct

<400> SEQUENCE: 1
tggcactctc cccctgtcg cgttcgctcg ctcgctggct cgtttggggg ggtggcagct      60
caaagagctg ccagacgacg gccctctggc cgtcgccccc ccaaacgagc cagcgagcga    120
gcgaacgcga caggggggag agtgccacac tctcaagcaa gggggttttg taagcagtga    180
tgtcataatg atgtaatgct tattgtcacg cgatagttaa tgattaacag tcatgtgatg    240
tgttttatcc aataggaaga aagcgcgcgt atgagttctc gcgagacttc cggggtataa    300
aagaccgagt gaacgagccc gccgccattc tttgctctgg actgctagag gaccctcgct    360
gccatggcta ccttctatga agtcattgtt cgcgtcccat ttgacgtgga ggaacatctg    420
cctggaattt ctgacagctt tgtggactgg gtaactggtc aaatttggga gctgcctcca    480
gagtcagatt taaatttgac tctggttgaa cagcctcagt tgacggtggc tgatagaatt    540
cgccgcgtgt tcctgtacga gtggaacaaa ttttccaagc aggagtccaa attctttgtg    600
cagtttgaaa agggatctga atattttcat ctgcacacgc ttgtggagac ctccggcatc    660
tcttccatgg tcctcggccg ctacgtgagt cagattcgcg cccagctggt gaaagtggtc    720
ttccagggaa ttgaacccca gatcaacgac tgggtcgcca tcaccaaggt aaagaagggc    780
ggagccaata aggtggtgga ttctgggtat attcccgcct acctgctgcc gaaggtccaa    840
ccggagcttc agtgggcgtg gacaaacctg acgagtata aattggccgc cctgaatctg    900
gaggagcgca acggctcgt cgcgcagttt ctggcagaat cctcgcagcg ctcgcaggag    960
gcggcttcgc agcgtgagtt ctcggctgac ccggtcatca aaagcaagac ttcccagaaa   1020
tacatggcgc tcgtcaactg gctcgtggag cacggcatca cttccgagaa gcagtggatc   1080
caggaaaatc aggagagcta cctctccttc aactccaccg gcaactctcg gagccagatc   1140
aaggccgcgc tcgacaacgc gaccaaaatt atgagtctga caaaaagcgc ggtggactac   1200
ctcgtgggga gctccgttcc cgaggacatt tcaaaaaaca gaatctggca aattttttgag   1260 atgaatggct acgacccggc ctacgcggga tccatcctct acggctggtg tcagcgctcc   1320
ttcaacaaga ggaacaccgt ctggctctac ggacccgcca cgaccggcaa gaccaacatc   1380
gcggaggcca tcgcccacac tgtgcccttt tacggctgcg tgaactggac caatgaaaac   1440 tttccctta tgactgtgt ggacaaaatg ctcatttggt gggaggaggg aaagatgacc   1500
aacaaggtgg ttgaatccgc caaggccatc ctgggggggct caaaggtgcg ggtcgatcag   1560
aaatgtaaat cctctgttca aattgattct accctgtca ttgtaacttc caatacaaac   1620
atgtgtgtgt tggtggatgg gaattccacg acctttgaac accagcagcc gctggaggac   1680
cgcatgttca aatttgaact gactaagcgg ctcccgccag attttggcaa gattactaag   1740
caggaagtca aggactttt tgcttgggca aggtcaatc aggtgccggt gactcacgag   1800
tttaaagttc ccagggaatt ggcgggaact aaaggggcgg agaaatctct aaaacgccca   1860
ctgggtgacg tcaccaatac tagctataaa agtctggaga gcgggccag gctctcattt   1920 gttcccgaga cgcctcgcag ttcagacgtg actgttgatc ccgctcctct gcgaccgctc   1980
aattggaatt caaggtatga ttgcaaatgt gactatcatg ctcaatttga caacatttct   2040
aacaaatgtg atgaatgtga atatttgaat cggggcaaaa atggatgtat ctgtcacaat   2100
gtaactcact gtcaaatttg tcatgggatt cccccctggg aaaaggaaaa cttgtcagat   2160
tttggggatt ttgacgatgc caataaagaa cagtaaataa agcgagtagt catgtctttt   2220
```

-continued

```
gttgatcacc ctccagattg gttggaagaa gttggtgaag gtcttcgcga gtttttgggc      2280
cttgaagcgg gcccaccgaa accaaaaccc aatcagcagc atcaagatca agcccgtggt      2340
cttgtgctgc ctggttataa ctatctcgga cccggaaacg gtctcgatcg aggagagcct      2400
gtcaacaggg cagacgaggt cgcgcgagag cacgacatct cgtacaacga gcagcttgag      2460
gcgggagaca ccccctacct caagtacaac cacgcggacg ccgagtttca ggagaagctc      2520
gccgacgaca catccttcgg gggaaacctc ggaaaggcag tctttcaggc caagaaaagg      2580
gttctcgaac cttttggcct ggttgaagag ggtgctaaga cggcccctac cggaaagcgg      2640
atagacgacc actttccaaa aagaaagaag gctcggaccg aagaggactc caagccttcc      2700
acctcgtcag acgccgaagc tggacccagc ggatcccagc agctgcaaat cccagcccaa      2760
ccagcctcaa gtttgggagc tgatacaatg tctgcgggag gtggcggccc attgggcgac      2820
aataaccaag gtgccgatgg agtgggcaat gcctcgggag attggcattg cgattccacg      2880
tggatggggg acagagtcgt caccaagtcc acccgaacct gggtgctgcc cagctacaac      2940
aaccaccagt accgagagat caaaagcggc tccgtcgacg gaagcaacgc caacgcctac      3000
tttggataca gcacccccctg ggggtacttt gactttaacc gcttccacag ccactggagc      3060
ccccgagact ggcaaagact catcaacaac tactggggct tcagacccccg gtccctcaga      3120 gtcaaaatct tcaacattca agtcaaagag gtcacggtgc aggactccac caccaccatc      3180
gccaacaacc tcacctccac cgtccaagtg tttacgacg acgactacca gctgccctac      3240
gtcgtcggca acgggaccga gggatgcctg ccggccttcc ctccgcaggt ctttacgctg      3300
ccgcagtacg gttacgcgac gctgaaccgc gacaacacag aaaatcccac cgagaggagc      3360
agcttcttct gcctagagta ctttcccagc aagatgctga aacgggcaa caactttgag      3420 tttacctaca actttgagga ggtgcccttc cactccagct cgctcccag tcagaacctg      3480 ttcaagctgg ccaacccgct ggtggaccag tacttgtacc gcttcgtgag cacaaataac      3540
actggcggag tccagttcaa caagaacctg gccgggagat acgccaacac ctacaaaaac      3600
tggttcccgg ggcccatggg ccgaacccag ggctggaacc tgggctccgg ggtcaaccgc      3660
gccagtgtca gcgccttcgc cacgaccaat aggatggagc tcgagggcgc gagttaccag      3720
gtgcccccgc agccgaacgg catgaccaac aacctccagg cagcaacac ctatgccctg      3780 gagaacacta tgatcttcaa cagccagccg gcgaacccgg gcaccaccgc cacgtacctc      3840
gagggcaaca tgctcatcac cagcgagagc gagacgcagc cggtgaaccg cgtggcgtac      3900
aacgtcggcg ggcagatggc caccaacaac cagagctcca ccactgcccc cgcgaccggc      3960
acgtacaacc tccaggaaat cgtgcccggc agcgtgtgga tggagaggga cgtgtacctc      4020
caaggaccca tctgggccaa gatcccagag acgggggcgc actttcaccc ctctccggcc      4080
atgggcggat tcggactcaa acacccaccg cccatgatgc tcatcaagaa cacgcctgtg      4140
cccggaaata tcaccagctt ctcggacgtg cccgtcagca gcttcatcac ccagtacagc      4200
accgggcagg tcaccgtgga gatggagtgg gagctcaaga aggaaaactc caagaggtgg      4260
aacccagaga tccagtacac aaacaactac aacgaccccc agtttgtgga ctttgccccg      4320
gacagcaccg gggaatacag aaccaccaga cctatcggaa cccgatacct acccgaccc      4380 cttttaaccca ttcatgtcgc ataccctcaa taaaccgtgt attcgtgtca gtaaaatact      4440
gcctcttgtg gtcattcaat gaataacagc ttacaacatc tacaaaacct ccttgcttga      4500
gagtgtggca ctctcccccc tgtcgcgttc gctcgctcgc tggctcgttt ggggggggtgg      4560
```

-continued

```
cagctcaaag agctgccaga cgacggccct ctggccgtcg ccccccaaa cgagccagcg    4620 agcgagcgaa cgcgacaggg gggagagtgc ca                                 4652
```

<210> SEQ ID NO 2
<211> LENGTH: 390
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 2

```
Met Ala Leu Val Asn Trp Leu Val Glu His Gly Ile Thr Ser Glu Lys
 1               5                  10                  15

Gln Trp Ile Gln Glu Asn Gln Glu Ser Tyr Leu Ser Phe Asn Ser Thr
            20                  25                  30

Gly Asn Ser Arg Ser Gln Ile Lys Ala Ala Leu Asp Asn Ala Thr Lys
        35                  40                  45

Ile Met Ser Leu Thr Lys Ser Ala Val Asp Tyr Leu Val Gly Ser Ser
    50                  55                  60

Val Pro Glu Asp Ile Ser Lys Asn Arg Ile Trp Gln Ile Phe Glu Met
65                  70                  75                  80

Asn Gly Tyr Asp Pro Ala Tyr Ala Gly Ser Ile Leu Tyr Gly Trp Cys
                85                  90                  95

Gln Arg Ser Phe Asn Lys Arg Asn Thr Val Trp Leu Tyr Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Leu Ile Trp Trp Glu Glu Gly Lys Met Thr Asn
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Val Gln Ile Asp Ser Thr Pro Val
            180                 185                 190

Ile Val Thr Ser Asn Thr Asn Met Cys Val Val Asp Gly Asn Ser
        195                 200                 205

Thr Thr Phe Glu His Gln Gln Pro Leu Glu Asp Arg Met Phe Lys Phe
    210                 215                 220

Glu Leu Thr Lys Arg Leu Pro Pro Asp Phe Gly Lys Ile Thr Lys Gln
225                 230                 235                 240

Glu Val Lys Asp Phe Phe Ala Trp Ala Lys Val Asn Gln Val Pro Val
                245                 250                 255

Thr His Glu Phe Lys Val Pro Arg Glu Leu Ala Gly Thr Lys Gly Ala
            260                 265                 270

Glu Lys Ser Leu Lys Arg Pro Leu Gly Asp Val Thr Asn Thr Ser Tyr
        275                 280                 285

Lys Ser Leu Glu Lys Arg Ala Arg Leu Ser Phe Val Pro Glu Thr Pro
    290                 295                 300

Arg Ser Ser Asp Val Thr Val Asp Pro Ala Pro Leu Arg Pro Leu Asn
305                 310                 315                 320

Trp Asn Ser Arg Tyr Asp Cys Lys Cys Asp Tyr His Ala Gln Phe Asp
                325                 330                 335

Asn Ile Ser Asn Lys Cys Asp Glu Cys Glu Tyr Leu Asn Arg Gly Lys
```

```
              340                 345                 350
Asn Gly Cys Ile Cys His Asn Val Thr His Cys Gln Ile Cys His Gly
            355                 360                 365

Ile Pro Pro Trp Glu Lys Glu Asn Leu Ser Asp Phe Gly Asp Phe Asp
    370                 375                 380

Asp Ala Asn Lys Glu Gln
385                 390

<210> SEQ ID NO 3
<211> LENGTH: 610
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 3

Met Ala Thr Phe Tyr Glu Val Ile Val Arg Val Pro Phe Asp Val Glu
  1               5                  10                  15

Glu His Leu Pro Gly Ile Ser Asp Ser Phe Val Asp Trp Val Thr Gly
                 20                  25                  30

Gln Ile Trp Glu Leu Pro Pro Glu Ser Asp Leu Asn Leu Thr Leu Val
             35                  40                  45

Glu Gln Pro Gln Leu Thr Val Ala Asp Arg Ile Arg Arg Val Phe Leu
         50                  55                  60

Tyr Glu Trp Asn Lys Phe Ser Lys Gln Glu Ser Lys Phe Phe Val Gln
 65                  70                  75                  80

Phe Glu Lys Gly Ser Glu Tyr Phe His Leu His Thr Leu Val Glu Thr
                 85                  90                  95

Ser Gly Ile Ser Ser Met Val Leu Gly Arg Tyr Val Ser Gln Ile Arg
                100                 105                 110

Ala Gln Leu Val Lys Val Val Phe Gln Gly Ile Glu Pro Gln Ile Asn
            115                 120                 125

Asp Trp Val Ala Ile Thr Lys Val Lys Lys Gly Gly Ala Asn Lys Val
        130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
            180                 185                 190

Ser Ser Gln Arg Ser Gln Glu Ala Ala Ser Gln Arg Glu Phe Ser Ala
        195                 200                 205

Asp Pro Val Ile Lys Ser Lys Thr Ser Gln Lys Tyr Met Ala Leu Val
    210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Thr Lys Ile Met Ser Leu
            260                 265                 270

Thr Lys Ser Ala Val Asp Tyr Leu Val Gly Ser Ser Val Pro Glu Asp
        275                 280                 285

Ile Ser Lys Asn Arg Ile Trp Gln Ile Phe Glu Met Asn Gly Tyr Asp
    290                 295                 300
```

```
Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
            325                 330                 335

Thr Asn Ile Ala Glu Ala Ile Ala His Thr Val Pro Phe Tyr Gly Cys
        340                 345                 350

Val Asn Trp Thr Asn Glu Asn Phe Pro Phe Asn Asp Cys Val Asp Lys
    355                 360                 365

Met Leu Ile Trp Trp Glu Gly Lys Met Thr Asn Lys Val Val Glu
    370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
                405                 410                 415

Asn Thr Asn Met Cys Val Val Val Asp Gly Asn Ser Thr Thr Phe Glu
            420                 425                 430

His Gln Gln Pro Leu Glu Asp Arg Met Phe Lys Phe Glu Leu Thr Lys
        435                 440                 445

Arg Leu Pro Pro Asp Phe Gly Lys Ile Thr Lys Gln Glu Val Lys Asp
    450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
                485                 490                 495

Lys Arg Pro Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
        515                 520                 525

Val Thr Val Asp Pro Ala Pro Leu Arg Pro Leu Asn Trp Asn Ser Arg
    530                 535                 540

Tyr Asp Cys Lys Cys Asp Tyr His Ala Gln Phe Asp Asn Ile Ser Asn
545                 550                 555                 560

Lys Cys Asp Glu Cys Gly Tyr Leu Asn Arg Gly Lys Asn Gly Cys Ile
                565                 570                 575

Cys His Asn Val Thr His Cys Gln Ile Cys His Gly Ile Pro Pro Trp
            580                 585                 590

Glu Lys Glu Asn Leu Ser Asp Phe Gly Asp Phe Asp Asp Ala Asn Lys
        595                 600                 605

Glu Gln
    610

<210> SEQ ID NO 4
<211> LENGTH: 724
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 4

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Lys Pro Lys
            20                  25                  30

Pro Asn Gln Gln His Gln Asp Gln Ala Arg Gly Leu Val Leu Pro Gly
            35                  40                  45
```

-continued

```
Tyr Asn Tyr Leu Gly Pro Gly Asn Gly Leu Asp Arg Gly Glu Pro Val
     50                  55                  60

Asn Arg Ala Asp Glu Val Ala Arg Glu His Asp Ile Ser Tyr Asn Glu
 65                  70                  75                  80

Gln Leu Glu Ala Gly Asp Asn Pro Tyr Leu Lys Tyr Asn His Ala Asp
                 85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
```

```
                465                 470                 475                 480
        Val Asn Arg Ala Ser Val Ser Ala Phe Ala Thr Thr Asn Arg Met Glu
                        485                 490                 495

Leu Glu Gly Ala Ser Tyr Gln Val Pro Pro Gln Pro Asn Gly Met Thr
                        500                 505                 510

Asn Asn Leu Gln Gly Ser Asn Thr Tyr Ala Leu Glu Asn Thr Met Ile
                        515                 520                 525

Phe Asn Ser Gln Pro Ala Asn Pro Gly Thr Thr Ala Thr Tyr Leu Glu
                530                 535                 540

Gly Asn Met Leu Ile Thr Ser Glu Ser Glu Thr Gln Pro Val Asn Arg
        545                 550                 555                 560

Val Ala Tyr Asn Val Gly Gly Gln Met Ala Thr Asn Asn Gln Ser Ser
                        565                 570                 575

Thr Thr Ala Pro Ala Thr Gly Thr Tyr Asn Leu Gln Glu Ile Val Pro
                        580                 585                 590

Gly Ser Val Trp Met Glu Arg Asp Val Tyr Leu Gln Gly Pro Ile Trp
                        595                 600                 605

Ala Lys Ile Pro Glu Thr Gly Ala His Phe His Pro Ser Pro Ala Met
                        610                 615                 620

Gly Gly Phe Gly Leu Lys His Pro Pro Met Met Leu Ile Lys Asn
        625                 630                 635                 640

Thr Pro Val Pro Gly Asn Ile Thr Ser Phe Ser Asp Val Pro Val Ser
                        645                 650                 655

Ser Phe Ile Thr Gln Tyr Ser Thr Gly Gln Val Thr Val Glu Met Glu
                        660                 665                 670

Trp Glu Leu Lys Lys Glu Asn Ser Lys Arg Trp Asn Pro Glu Ile Gln
                        675                 680                 685

Tyr Thr Asn Asn Tyr Asn Asp Pro Gln Phe Val Asp Phe Ala Pro Asp
                690                 695                 700

Ser Thr Gly Glu Tyr Arg Thr Thr Arg Pro Ile Gly Thr Arg Tyr Leu
        705                 710                 715                 720

Thr Arg Pro Leu

<210> SEQ ID NO 5
<211> LENGTH: 588
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 5

Thr Ala Pro Thr Gly Lys Arg Ile Asp Asp His Phe Pro Lys Arg Lys
        1               5                   10                  15

Lys Ala Arg Thr Glu Glu Asp Ser Lys Pro Ser Thr Ser Ser Asp Ala
                        20                  25                  30

Glu Ala Gly Pro Ser Gly Ser Gln Gln Leu Gln Ile Pro Ala Gln Pro
                    35                  40                  45

Ala Ser Ser Leu Gly Ala Asp Thr Met Ser Ala Gly Gly Gly Gly Pro
                50                  55                  60

Leu Gly Asp Asn Asn Gln Gly Ala Asp Gly Val Gly Asn Ala Ser Gly
        65                  70                  75                  80

Asp Trp His Cys Asp Ser Thr Trp Met Gly Asp Arg Val Val Thr Lys
                        85                  90                  95

Ser Thr Arg Thr Trp Val Leu Pro Ser Tyr Asn Asn His Gln Tyr Arg
```

-continued

```
            100                 105                 110
Glu Ile Lys Ser Gly Ser Val Asp Gly Ser Asn Ala Asn Ala Tyr Phe
            115                 120                 125
Gly Tyr Ser Thr Pro Trp Gly Tyr Phe Asp Phe Asn Arg Phe His Ser
            130                 135                 140
His Trp Ser Pro Arg Asp Trp Gln Arg Leu Ile Asn Asn Tyr Trp Gly
145                 150                 155                 160
Phe Arg Pro Arg Ser Leu Arg Val Lys Ile Phe Asn Ile Gln Val Lys
            165                 170                 175
Glu Val Thr Val Gln Asp Ser Thr Thr Thr Ile Ala Asn Asn Leu Thr
            180                 185                 190
Ser Thr Val Gln Val Phe Thr Asp Asp Asp Tyr Gln Leu Pro Tyr Val
            195                 200                 205
Val Gly Asn Gly Thr Glu Gly Cys Leu Pro Ala Phe Pro Pro Gln Val
            210                 215                 220
Phe Thr Leu Pro Gln Tyr Gly Tyr Ala Thr Leu Asn Arg Asp Asn Thr
225                 230                 235                 240
Glu Asn Pro Thr Glu Arg Ser Ser Phe Phe Cys Leu Glu Tyr Phe Pro
            245                 250                 255
Ser Lys Met Leu Arg Thr Gly Asn Asn Phe Glu Phe Thr Tyr Asn Phe
            260                 265                 270
Glu Glu Val Pro Phe His Ser Ser Phe Ala Pro Ser Gln Asn Leu Phe
            275                 280                 285
Lys Leu Ala Asn Pro Leu Val Asp Gln Tyr Leu Tyr Arg Phe Val Ser
            290                 295                 300
Thr Asn Asn Thr Gly Gly Val Gln Phe Asn Lys Asn Leu Ala Gly Arg
305                 310                 315                 320
Tyr Ala Asn Thr Tyr Lys Asn Trp Phe Pro Gly Pro Met Gly Arg Thr
            325                 330                 335
Gln Gly Trp Asn Leu Gly Ser Gly Val Asn Arg Ala Ser Val Ser Ala
            340                 345                 350
Phe Ala Thr Thr Asn Arg Met Glu Leu Glu Gly Ala Ser Tyr Gln Val
            355                 360                 365
Pro Pro Gln Pro Asn Gly Met Thr Asn Asn Leu Gln Gly Ser Asn Thr
            370                 375                 380
Tyr Ala Leu Glu Asn Thr Met Ile Phe Asn Ser Gln Pro Ala Asn Pro
385                 390                 395                 400
Gly Thr Thr Ala Thr Tyr Leu Glu Gly Asn Met Leu Ile Thr Ser Glu
            405                 410                 415
Ser Glu Thr Gln Pro Val Asn Arg Val Ala Tyr Asn Val Gly Gly Gln
            420                 425                 430
Met Ala Thr Asn Asn Gln Ser Ser Thr Thr Ala Pro Ala Thr Gly Thr
            435                 440                 445
Tyr Asn Leu Gln Glu Ile Val Pro Gly Ser Val Trp Met Glu Arg Asp
            450                 455                 460
Val Tyr Leu Gln Gly Pro Ile Trp Ala Lys Ile Pro Glu Thr Gly Ala
465                 470                 475                 480
His Phe His Pro Ser Pro Ala Met Gly Gly Phe Gly Leu Lys His Pro
            485                 490                 495
Pro Pro Met Met Leu Ile Lys Asn Thr Pro Val Pro Gly Asn Ile Thr
            500                 505                 510
Ser Phe Ser Asp Val Pro Val Ser Phe Ile Thr Gln Tyr Ser Thr
            515                 520                 525
```

```
Gly Gln Val Thr Val Glu Met Glu Trp Glu Leu Lys Lys Glu Asn Ser
            530                 535                 540
Lys Arg Trp Asn Pro Glu Ile Gln Tyr Thr Asn Asn Tyr Asn Asp Pro
545                 550                 555                 560
Gln Phe Val Asp Phe Ala Pro Asp Ser Thr Gly Glu Tyr Arg Thr Thr
                565                 570                 575
Arg Pro Ile Gly Thr Arg Tyr Leu Thr Arg Pro Leu
            580                 585

<210> SEQ ID NO 6
<211> LENGTH: 532
<212> TYPE: PRT
<213> ORGANISM: Artificial Sequence
<220> FEATURE:
<223> OTHER INFORMATION: Description of Artificial Sequence:/Note =
      synthetic construct

<400> SEQUENCE: 6

Met Ser Ala Gly Gly Gly Pro Leu Gly Asp Asn Gln Gly Ala
 1               5                  10                  15
Asp Gly Val Gly Asn Ala Ser Gly Asp Trp His Cys Asp Ser Thr Trp
            20                  25                  30
Met Gly Asp Arg Val Val Thr Lys Ser Thr Arg Thr Trp Val Leu Pro
        35                  40                  45
Ser Tyr Asn Asn His Gln Tyr Arg Glu Ile Lys Ser Gly Ser Val Asp
    50                  55                  60
Gly Ser Asn Ala Asn Ala Tyr Phe Gly Tyr Ser Thr Pro Trp Gly Tyr
65                  70                  75                  80
Phe Asp Phe Asn Arg Phe His Ser His Trp Ser Pro Arg Asp Trp Gln
                85                  90                  95
Arg Leu Ile Asn Asn Tyr Trp Gly Phe Arg Pro Arg Ser Leu Arg Val
            100                 105                 110
Lys Ile Phe Asn Ile Gln Val Lys Glu Val Thr Val Gln Asp Ser Thr
        115                 120                 125
Thr Thr Ile Ala Asn Asn Leu Thr Ser Thr Val Gln Val Phe Thr Asp
    130                 135                 140
Asp Asp Tyr Gln Leu Pro Tyr Val Val Gly Asn Gly Thr Glu Gly Cys
145                 150                 155                 160
Leu Pro Ala Phe Pro Pro Gln Val Phe Thr Leu Pro Gln Tyr Gly Tyr
                165                 170                 175
Ala Thr Leu Asn Arg Asp Asn Thr Glu Asn Pro Thr Glu Arg Ser Ser
            180                 185                 190
Phe Phe Cys Leu Glu Tyr Phe Pro Ser Lys Met Leu Arg Thr Gly Asn
        195                 200                 205
Asn Phe Glu Phe Thr Tyr Asn Phe Glu Glu Val Pro Phe His Ser Ser
    210                 215                 220
Phe Ala Pro Ser Gln Asn Leu Phe Lys Leu Ala Asn Pro Leu Val Asp
225                 230                 235                 240
Gln Tyr Leu Tyr Arg Phe Val Ser Thr Asn Asn Thr Gly Gly Val Gln
                245                 250                 255
Phe Asn Lys Asn Leu Ala Gly Arg Tyr Ala Asn Thr Tyr Lys Asn Trp
            260                 265                 270
Phe Pro Gly Pro Met Gly Arg Thr Gln Gly Trp Asn Leu Gly Ser Gly
        275                 280                 285
Val Asn Arg Ala Ser Val Ser Ala Phe Ala Thr Thr Asn Arg Met Glu
```

-continued

```
                   290                 295                 300
Leu Glu Gly Ala Ser Tyr Gln Val Pro Pro Gln Pro Asn Gly Met Thr
305                 310                 315                 320

Asn Asn Leu Gln Gly Ser Asn Thr Tyr Ala Leu Glu Asn Thr Met Ile
                325                 330                 335

Phe Asn Ser Gln Pro Ala Asn Pro Gly Thr Thr Ala Thr Tyr Leu Glu
                340                 345                 350

Gly Asn Met Leu Ile Thr Ser Glu Ser Glu Thr Gln Pro Val Asn Arg
                355                 360                 365

Val Ala Tyr Asn Val Gly Gly Gln Met Ala Thr Asn Asn Gln Ser Ser
                370                 375                 380

Thr Thr Ala Pro Ala Thr Gly Thr Tyr Asn Leu Gln Glu Ile Val Pro
385                 390                 395                 400

Gly Ser Val Trp Met Glu Arg Asp Val Tyr Leu Gln Gly Pro Ile Trp
                    405                 410                 415

Ala Lys Ile Pro Glu Thr Gly Ala His Phe His Pro Ser Pro Ala Met
                420                 425                 430

Gly Gly Phe Gly Leu Lys His Pro Pro Met Met Leu Ile Lys Asn
                435                 440                 445

Thr Pro Val Pro Gly Asn Ile Thr Ser Phe Ser Asp Val Pro Val Ser
                450                 455                 460

Ser Phe Ile Thr Gln Tyr Ser Thr Gly Gln Val Thr Val Glu Met Glu
465                 470                 475                 480

Trp Glu Leu Lys Lys Glu Asn Ser Lys Arg Trp Asn Pro Glu Ile Gln
                485                 490                 495

Tyr Thr Asn Asn Tyr Asn Asp Pro Gln Phe Val Asp Phe Ala Pro Asp
                500                 505                 510

Ser Thr Gly Glu Tyr Arg Thr Thr Arg Pro Ile Gly Thr Arg Tyr Leu
                515                 520                 525

Thr Arg Pro Leu
    530

<210> SEQ ID NO 7
<211> LENGTH: 2307
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 7
aggctctcat tgttcccga  dacgcctcgc  agttcagacg  tgactgttga  tcccgctcct    60
ctgcgaccgc tcaattggaa ttcaagtaaa taaagcgagt agtcatgtct tttgttgatc    120
accctccaga ttggttggaa gaagttggtg aaggtcttcg cgagttttg  ggccttgaag    180 cgggcccacc gaaaccaaaa cccaatcagc agcatcaaga tcaagcccgt ggtcttgtgc    240
tgcctggtta taactatctc ggacccggaa acggtctcga tcgaggagag cctgtcaaca    300
gggcagacga ggtcgcgcga gagcacgaca tctcgtacaa cgagcagctt gaggcgggag    360
acaaccccta cctcaagtac aaccacgcgg acgccgagtt tcaggagaag ctcgccgacg    420
acacatcctt cggggggaaac ctcggaaagg cagtctttca ggccaagaaa agggttctcg    480
aaccttttgg cctggttgaa gagggtgcta agacggcccc taccggaaag cggatagacg    540
accactttcc aaaagaaag  aaggctcgga ccgaagagga  ctccaagcct tccacctcgt    600
cagacgccga agctggaccc agcggatccc agcagctgca aatcccagcc caaccagcct    660
```

| caagtttggg agctgataca atgtctgcgg gaggtggcgg cccattgggc gacaataacc | 720 |
| aaggtgccga tggagtgggc aatgcctcgg agattggca ttgcgattcc acgtggatgg | 780 |
| gggacagagt cgtcaccaag tccacccgaa cctgggtgct gcccagctac aacaaccacc | 840 |
| agtaccgaga gatcaaaagc ggctccgtcg acggaagcaa cgccaacgcc tactttggat | 900 |
| acagcacccc ctgggggtac tttgactta accgcttcca cagccactgg agccccgag | 960 |
| actggcaaag actcatcaac aactactggg gcttcagacc ccggtccctc agagtcaaaa | 1020 |
| tcttcaacat tcaagtcaaa gaggtcacgg tgcaggactc caccaccacc atcgccaaca | 1080 |
| acctcacctc caccgtccaa gtgtttacgg acgacgacta ccagctgccc tacgtcgtcg | 1140 |
| gcaacgggac cgagggatgc ctgccggcct ccctccgca ggtctttacg ctgccgcagt | 1200 |
| acggttacgc gacgctgaac cgcgacaaca cagaaaatcc caccgagagg agcagcttct | 1260 |
| tctgcctaga gtactttccc agcaagatgc tgagaacggg caacaacttt gagtttacct | 1320 |
| acaactttga ggaggtgccc ttccactcca gcttcgctcc cagtcagaac ctgttcaagc | 1380 |
| tggccaaccc gctggtggac cagtacttgt accgcttcgt gagcacaaat aacactggcg | 1440 |
| gagtccagtt caacaagaac ctggccggga gatacgccaa cacctacaaa aactggttcc | 1500 |
| cggggcccat gggccgaacc cagggctgga acctgggctc cggggtcaac cgcgccagtg | 1560 |
| tcagcgcctt cgccacgacc aataggatgg agctcgaggg cgcgagttac caggtgcccc | 1620 |
| cgcagccgaa cggcatgacc aacaacctcc agggcagcaa cacctatgcc ctggagaaca | 1680 |
| ctatgatctt caacagccag ccggcgaacc cgggcaccac cgccacgtac ctcgagggca | 1740 |
| acatgctcat caccagcgag agcgagacgc agccggtgaa ccgcgtggcg tacaacgtcg | 1800 |
| gcgggcagat ggccaccaac aaccagagct ccaccactgc ccccgcgacc ggcacgtaca | 1860 |
| acctccagga aatcgtgccc ggcagcgtgt ggatggagag ggacgtgtac ctccaaggac | 1920 |
| ccatctgggc caagatccca gagacggggg cgcactttca ccctctccg gccatgggcg | 1980 |
| gattcggact caaacacccca ccgcccatga tgctcatcaa gaacacgcct gtgcccggaa | 2040 |
| atatcaccag cttctcggac gtgcccgtca gcagcttcat cacccagtac agcaccgggc | 2100 |
| aggtcaccgt ggagatggag tgggagctca agaaggaaaa ctccaagagg tggaacccag | 2160 |
| agatccagta cacaaacaac tacaacgacc ccagtttgt ggactttgcc ccggacagca | 2220 |
| ccggggaata cagaaccacc agacctatcg gaacccgata ccttacccga ccccttaac | 2280 |
| ccattcatgt cgcatacct caataaa | 2307 |

<210> SEQ ID NO 8
<211> LENGTH: 2264
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 8

| aggctctcat ttgttcccga gacgcctcgc agttcagacg tgactgttga tcccgctcct | 60 |
| ctgcgaccgc tcaattggaa ttcaagattg gttggaagaa gttggtgaag gtcttcgcga | 120 |
| gtttttgggc cttgaagcgg gcccaccgaa accaaaaccc aatcagcagc atcaagatca | 180 |
| agcccgtggt cttgtgctgc ctggttataa ctatctcgga cccggaaacg gtctcgatcg | 240 |
| aggagagcct gtcaacaggg cagacgaggt cgcgcgagag cacgacatct cgtacaacga | 300 |
| gcagcttgag gcgggagaca accctacct caagtacaac cacgcggacg ccgagtttca | 360 |

```
ggagaagctc gccgacgaca catccttcgg gggaaacctc ggaaaggcag tctttcaggc    420
caagaaaagg gttctcgaac cttttggcct ggttgaagag ggtgctaaga cggcccctac    480
cggaaagcgg atagacgacc actttccaaa aagaaagaag gctcggaccg aagaggactc    540
caagccttcc acctcgtcag acgccgaagc tggacccagc ggatcccagc agctgcaaat    600
cccagcccaa ccagcctcaa gtttgggagc tgatacaatg tctgcgggag gtggcggccc    660
attgggcgac aataaccaag gtgccgatgg agtgggcaat gcctcgggag attggcattg    720
cgattccacg tggatggggg acagagtcgt caccaagtcc acccgaacct gggtgctgcc    780
cagctacaac aaccaccagt accgagagat caaaagcggc tccgtcgacg aagcaacgc    840
caacgcctac tttggataca gcacccctg ggggtacttt gactttaacc gcttccacag    900
ccactggagc ccccgagact ggcaaagact catcaacaac tactggggct tcagaccccg    960
gtccctcaga gtcaaaatct tcaacattca agtcaaagag gtcacggtgc aggactccac   1020
caccaccatc gccaacaacc tcacctccac cgtccaagtg tttacggacg acgactacca   1080
gctgccctac gtcgtcggca acgggaccga gggatgcctg ccggccttcc ctccgcaggt   1140
cttacgctg ccgcagtacg gttacgcgac gctgaaccgc gacaacacag aaaatcccac   1200
cgagaggagc agcttcttct gcctagagta ctttcccagc aagatgctga aacgggcaa   1260
caactttgag tttacctaca actttgagga ggtgcccttc cactccagct cgctcccag   1320
tcagaacctg ttcaagctgg ccaacccgct ggtggaccag tacttgtacc gcttcgtgag   1380
cacaaataac actggcggag tccagttcaa caagaacctg gccggagat acgccaacac   1440
ctacaaaaac tggttcccgg ggcccatggg ccgaacccag ggctggaacc tgggctccgg   1500
ggtcaaccgc gccagtgtca gcgccttcgc cacgaccaat aggatggagc tcgagggcgc   1560
gagttaccag gtgcccccgc agccgaacgg catgaccaac aacctccagg cagcaacac   1620
ctatgccctg gagaacacta tgatcttcaa cagccagccg gcgaacccgg gcaccaccgc   1680
cacgtacctc gagggcaaca tgctcatcac cagcgagagc gagacgcagc cggtgaaccg   1740
cgtggcgtac aacgtcggcg ggcagatggc caccaacaac cagagctcca ccactgcccc   1800
cgcgaccggc acgtacaacc tccaggaaat cgtgcccggc agcgtgtgga tggagaggga   1860
cgtgtacctc caaggaccca tctgggccaa gatcccagag acggggggcgc actttcaccc   1920
ctctccggcc atgggcggat tcggactcaa acacccaccg cccatgatgc tcatcaagaa   1980
cacgcctgtg cccggaaata tcaccagctt ctcggacgtg cccgtcagca gcttcatcac   2040
ccagtacagc accgggcagg tcaccgtgga gatggagtgg gagctcaaga aggaaaactc   2100
caagaggtgg aacccagaga tccagtacac aaacaactac aacgaccccc agtttgtgga   2160
ctttgccccg gacagcaccg gggaatacag aaccaccaga cctatcggaa cccgatacct   2220
tacccgaccc ctttaaccca ttcatgtcgc ataccctcaa taaa                    2264
```

<210> SEQ ID NO 9
<211> LENGTH: 2264
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 9

```
aggctctcat tgttcccga gacgcctcgc agttcagacg tgactgttga tcccgctcct     60
ctgcgaccgc tcaattggaa ttcaagattg gttggaagaa gttggtgaag gtcttcgcga   120
```

-continued

```
gtttttgggc cttgaagcgg gcccaccgaa accaaaaccc aatcagcagc atcaagatca      180
agcccgtggt cttgtgctgc ctggttataa ctatctcgga cccggaaacg gtctcgatcg      240
aggagagcct gtcaacaggg cagacgaggt cgcgcgagag cacgacatct cgtacaacga      300
gcagcttgag gcgggagaca accctacct caagtacaac cacgcggacg ccgagtttca       360
ggagaagctc gccgacgaca catccttcgg gggaaacctc ggaaaggcag tctttcaggc      420
caagaaaagg gttctcgaac cttttggcct ggttgaagag ggtgctaaga cggcccctac      480
cggaaagcgg atagacgacc actttccaaa aagaaagaag gctcggaccg aagaggactc      540
caagccttcc acctcgtcag acgccgaagc tggacccagc ggatcccagc agctgcaaat      600
cccagcccaa ccagcctcaa gtttgggagc tgatacaatg tctgcgggag gtggcggccc      660
attgggcgac aataaccaag gtgccgatgg agtgggcaat gcctcgggag attggcattg      720
cgattccacg tggatggggg acagagtcgt caccaagtcc acccgaacct gggtgctgcc      780
cagctacaac aaccaccagt accgagagat caaaagcggc tccgtcgacg gaagcaacgc      840
caacgcctac tttggataca gcaccccctg ggggtacttt gactttaacc gcttccacag      900
ccactggagc ccccgagact ggcaaagact catcaacaac tactggggct tcagaccccg      960
gtccctcaga gtcaaaatct tcaacattca gtcaaagag gtcacggtgc aggactccac      1020
caccaccatc gccaacaacc tcacctccac cgtccaagtg tttacggacg acgactacca     1080
gctgccctac gtcgtcggca acgggaccga gggatgcctg ccggccttcc ctccgcaggt     1140
cttacgctg ccgcagtacg gttacgcgac gctgaaccgc gacaacacag aaaatcccac      1200
cgagaggagc agcttcttct gcctagagta ctttcccagc aagatgctga aacgggcaa     1260
caactttgag tttacctaca actttgagga ggtgcccttc cactccagct cgctcccag    1320
tcagaacctg ttcaagctgg ccaacccgct ggtggaccag tacttgtacc gcttcgtgag   1380
cacaaataac actggcggag tccagttcaa caagaacctg gccgggagat acgccaacac    1440
ctacaaaaac tggttcccgg ggcccatggg ccgaacccag ggctggaacc tgggctccgg    1500
ggtcaaccgc gccagtgtca gcgccttcgc cacgaccaat aggatggagc tcgagggcgc    1560
gagttaccag gtgccccgc agccgaacgg catgaccaac aacctccagg gcagcaacac      1620
ctatgccctg gagaacacta tgatcttcaa cagccagccg gcgaacccgg gcaccaccgc    1680
cacgtacctc gagggcaaca tgctcatcac cagcgagagc gagacgcagc cggtgaaccg    1740
cgtggcgtac aacgtcggcg ggcagatggc caccaacaac cagagctcca ccactgcccc   1800
cgcgaccggc acgtacaacc tccaggaaat cgtgcccggc agcgtgtgga tggagaggga    1860
cgtgtacctc caaggaccca tctgggccaa gatcccagag acggggcgc actttcacc     1920
ctctccggcc atgggcggat tcggactcaa acacccaccg cccatgatgc tcatcaagaa     1980
cacgcctgtg cccggaaata tcaccagctt ctcggacgtg cccgtcagca gcttcatcac    2040
ccagtacagc accgggcagg tcaccgtgga gatggagtgg gagctcaaga aggaaaactc   2100
caagaggtgg aacccagaga tccagtacac aaacaactac aacgacccc agtttgtgga    2160
ctttgccccg gacagcaccg gggaatacag aaccaccaga cctatcggaa cccgatacct   2220
tacccgaccc cttaacccca ttcatgtcgc ataccctcaa taaa                     2264
```

<210> SEQ ID NO 10
<211> LENGTH: 1292
<212> TYPE: DNA
<213> ORGANISM: Artificial Sequence
<220> FEATURE:

<223> OTHER INFORMATION: Description of Artificial Sequence:/Note = synthetic construct

<400> SEQUENCE: 10

| | | | | | |
|---|---|---|---|---|---|
| agcgcaaacg | gctcgtcgcg | cagtttctgg | cagaatcctc | gcagcgctcg | caggaggcgg | 60 |
| cttcgcagcg | tgagttctcg | gctgacccgg | tcatcaaaag | caagacttcc | cagaaataca | 120 |
| tggcgctcgt | caactggctc | gtggagcacg | gcatcacttc | cgagaagcag | tggatccagg | 180 |
| aaaatcagga | gagctacctc | tccttcaact | ccaccggcaa | ctctcggagc | cagatcaagg | 240 |
| ccgcgctcga | caacgcgacc | aaaattatga | gtctgacaaa | aagcgcggtg | gactacctcg | 300 |
| tggggagctc | cgttcccgag | gacatttcaa | aaaacagaat | ctggcaaatt | tttgagatga | 360 |
| atggctacga | cccggcctac | gcgggatcca | tcctctacgg | ctggtgtcag | cgctccttca | 420 |
| acaagaggaa | caccgtctgg | ctctacggac | ccgccacgac | cggcaagacc | aacatcgcgg | 480 |
| aggccatcgc | ccacactgtg | cccttttacg | gctgcgtgaa | ctggaccaat | gaaaactttc | 540 |
| cctttaatga | ctgtgtggac | aaaatgctca | tttggtggga | ggagggaaag | atgaccaaca | 600 |
| aggtggttga | atccgccaag | gccatcctgg | ggggctcaaa | ggtgcgggtc | gatcagaaat | 660 |
| gtaaatcctc | tgttcaaatt | gattctaccc | ctgtcattgt | aacttccaat | acaaacatgt | 720 |
| gtgtggtggt | ggatgggaat | tccacgacct | tgaacacca | gcagccgctg | gaggaccgca | 780 |
| tgttcaaatt | tgaactgact | aagcggctcc | cgccagattt | tggcaagatt | actaagcagg | 840 |
| aagtcaagga | cttttttgct | tgggcaaagg | tcaatcaggt | gccggtgact | cacgagttta | 900 |
| aagttcccag | ggaattggcg | ggaactaaag | gggcggagaa | atctctaaaa | cgcccactgg | 960 |
| gtgacgtcac | caatactagc | tataaaagtc | tggagaagcg | ggccaggctc | tcatttgttc | 1020 |
| ccgagacgcc | tcgcagttca | gacgtgactg | ttgatcccgc | tcctctgcga | ccgctcaatt | 1080 |
| ggaattcaag | gtatgattgc | aaatgtgact | atcatgctca | atttgacaac | atttctaaca | 1140 |
| aatgtgatga | atgtgaatat | ttgaatcggg | gcaaaaatgg | atgtatctgt | cacaatgtaa | 1200 |
| ctcactgtca | aatttgtcat | gggattcccc | cctgggaaaa | ggaaaacttg | tcagattttg | 1260 |
| gggattttga | cgatgccaat | aaagaacagt | aa | | | 1292 |

<210> SEQ ID NO 11
<211> LENGTH: 1870
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 11

| | | | | | |
|---|---|---|---|---|---|
| attctttgct | ctggactgct | agaggaccct | cgctgccatg | gctaccttct | atgaagtcat | 60 |
| tgttcgcgtc | ccatttgacg | tggaggaaca | tctgcctgga | atttctgaca | gctttgtgga | 120 |
| ctgggtaact | ggtcaaattt | gggagctgcc | tccagagtca | gatttaaatt | tgactctggt | 180 |
| tgaacagcct | cagttgacgg | tggctgatag | aattcgccgc | gtgttcctgt | acgagtggaa | 240 |
| caaattttcc | aagcaggagt | ccaaattctt | tgtgcagttt | gaaaagggat | ctgaatattt | 300 |
| tcatctgcac | acgcttgtgg | agacctccgg | catctcttcc | atggtcctcg | gccgctacgt | 360 |
| gagtcagatt | cgcgcccagc | tggtgaaagt | ggtcttccag | ggaattgaac | ccagatcaa | 420 |
| cgactgggtc | gccatcacca | aggtaaagaa | gggcggagcc | aataaggtgg | tggattctgg | 480 |
| gtatattccc | gcctacctgc | tgccgaaggt | ccaaccggag | cttcagtggg | cgtggacaaa | 540 |
| cctggacgag | tataaaattgg | ccgccctgaa | tctggaggag | cgcaaacggc | tcgtcgcgca | 600 |

-continued

```
gtttctggca gaatcctcgc agcgctcgca ggaggcggct tcgcagcgtg agttctcggc    660
tgacccggtc atcaaaagca agacttccca gaaatacatg gcgctcgtca actggctcgt    720
ggagcacggc atcacttccg agaagcagtg gatccaggaa atcaggaga gctacctctc     780
cttcaactcc accggcaact ctcggagcca gatcaaggcc gcgctcgaca acgcgaccaa    840
aattatgagt ctgacaaaaa gcgcggtgga ctacctcgtg gggagctccg ttcccgagga    900
catttcaaaa aacagaatct ggcaaatttt tgagatgaat ggctacgacc cggcctacgc    960
gggatccatc ctctacggct ggtgtcagcg ctccttcaac aagaggaaca ccgtctggct   1020
ctacggaccc gccacgaccg gcaagaccaa catcgcggag gccatcgccc acactgtgcc   1080
cttttacggc tgcgtgaact ggaccaatga aactttccc tttaatgact gtgtggacaa    1140
aatgctcatt tggtgggagg agggaaagat gaccaacaag gtggttgaat ccgccaaggc   1200
catcctgggg ggctcaaagg tgcgggtcga tcagaaatgt aaatcctctg ttcaaattga   1260
ttctacccct gtcattgtaa cttccaatac aaacatgtgt gtggtggtgg atgggaattc   1320
cacgaccttt gaacaccagc agccgctgga ggaccgcatg ttcaaatttg aactgactaa   1380
gcggctcccg ccagattttg gcaagattac taagcaggaa gtcaaggact tttttgcttg   1440
ggcaaaggtc aatcaggtgc cggtgactca cgagtttaaa gttcccaggg aattggcggg   1500
aactaaaggg gcggagaaat ctctaaaacg cccactgggt gacgtcacca atactagcta   1560
taaaagtctg gagaagcggg ccaggctctc atttgttccc gagacgcctc gcagttcaga   1620
cgtgactgtt gatcccgctc ctctgcgacc gctcaattgg aattcaaggt atgattgcaa   1680
atgtgactat catgctcaat ttgacaacat ttctaacaaa tgtgatgaat gtgaatattt   1740
gaatcggggc aaaaatggat gtatctgtca caatgtaact cactgtcaaa tttgtcatgg   1800
gattcccccc tgggaaaagg aaaacttgtc agattttggg gattttgacg atgccaataa   1860
agaacagtaa                                                           1870
```

<210> SEQ ID NO 12
<211> LENGTH: 330
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 12

```
Met Ala Leu Val Asn Trp Leu Val Glu His Gly Ile Thr Ser Glu Lys
 1               5                  10                  15

Gln Trp Ile Gln Glu Asn Gln Glu Ser Tyr Leu Ser Phe Asn Ser Thr
            20                  25                  30

Gly Asn Ser Arg Ser Gln Ile Lys Ala Ala Leu Asp Asn Ala Thr Lys
        35                  40                  45

Ile Met Ser Leu Thr Lys Ser Ala Val Asp Tyr Leu Val Gly Ser Ser
    50                  55                  60

Val Pro Glu Asp Ile Ser Lys Asn Arg Ile Trp Gln Ile Phe Glu Met
65                  70                  75                  80

Asn Gly Tyr Asp Pro Ala Tyr Ala Gly Ser Ile Leu Tyr Gly Trp Cys
                85                  90                  95

Gln Arg Ser Phe Asn Lys Arg Asn Thr Val Trp Leu Tyr Gly Pro Ala
            100                 105                 110

Thr Thr Gly Lys Thr Asn Ile Ala Glu Ala Ile Ala His Thr Val Pro
        115                 120                 125
```

Phe Tyr Gly Cys Val Asn Trp Thr Asn Glu Asn Phe Pro Phe Asn Asp
            130                 135                 140

Cys Val Asp Lys Met Leu Ile Trp Trp Glu Glu Gly Lys Met Thr Asn
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Val Gln Ile Asp Ser Thr Pro Val
            180                 185                 190

Ile Val Thr Ser Asn Thr Asn Met Cys Val Val Asp Gly Asn Ser
            195                 200                 205

Thr Thr Phe Glu His Gln Gln Pro Leu Glu Asp Arg Met Phe Lys Phe
            210                 215                 220

Glu Leu Thr Lys Arg Leu Pro Pro Asp Phe Gly Lys Ile Thr Lys Gln
225                 230                 235                 240

Glu Val Lys Asp Phe Phe Ala Trp Ala Lys Val Asn Gln Val Pro Val
                245                 250                 255

Thr His Glu Phe Lys Val Pro Arg Glu Leu Ala Gly Thr Lys Gly Ala
            260                 265                 270

Glu Lys Ser Leu Lys Arg Pro Leu Gly Asp Val Thr Asn Thr Ser Tyr
            275                 280                 285

Lys Ser Leu Glu Lys Arg Ala Arg Leu Ser Phe Val Pro Glu Thr Pro
            290                 295                 300

Arg Ser Ser Asp Val Thr Val Asp Pro Ala Pro Leu Arg Pro Leu Asn
305                 310                 315                 320

Trp Asn Ser Arg Leu Val Gly Arg Ser Trp
                325                 330

<210> SEQ ID NO 13
<211> LENGTH: 1115
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 13
aggagcgcaa acggctcgtc gcgcagtttc tggcagaatc ctcgcagcgc tcgcaggagg      60
cggcttcgca gcgtgagttc tcggctgacc cggtcatcaa aagcaagact tcccagaaat     120
acatggcgct cgtcaactgg ctcgtggagc acggcatcac ttccgagaag cagtggatcc     180
aggaaaatca ggagagctac ctctccttca actccaccgg caactctcgg agccagatca     240
aggccgcgct cgacaacgcg accaaaatta tgagtctgac aaaaagcgcg gtggactacc     300
tcgtggggag ctccgttccc gaggacattt caaaaaacag aatctggcaa atttttgaga     360
tgaatggcta cgacccggcc tacgcgggat ccatcctcta cggctggtgt cagcgctcct     420
tcaacaagag gaacaccgtc tggctctacg acccgccac gaccggcaag accaacatcg     480
cggaggccat cgcccacact gtgccctttt acggctgcgt gaactggacc aatgaaaact     540 ttcccttta tgactgtgtg acaaaatgc tcatttggtg ggaggaggga agatgacca      600 acaaggtggt tgaatccgcc aaggccatcc tgggggctc aaaggtgcgg gtcgatcaga     660
aatgtaaatc ctctgttcaa attgattcta cccctgtcat tgtaacttcc aatacaaaca     720
tgtgtgtggt ggtggatggg aattccacga cctttgaaca ccagcagccg ctggaggacc     780
gcatgttcaa atttgaactg actaagcggc tcccgccaga ttttggcaag attactaagc     840

```
aggaagtcaa ggactttttt gcttgggcaa aggtcaatca ggtgccggtg actcacgagt    900
ttaaagttcc cagggaattg gcgggaacta aggggcgga gaaatctcta aaacgcccac    960
tgggtgacgt caccaatact agctataaaa gtctggagaa gcgggccagg ctctcatttg   1020
ttcccgagac gcctcgcagt tcagacgtga ctgttgatcc cgctcctctg cgaccgctca   1080
attggaattc aagattggtt ggaagaagtt ggtga                              1115
```

<210> SEQ ID NO 14
<211> LENGTH: 550
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 14

```
Met Ala Thr Phe Tyr Glu Val Ile Val Arg Val Pro Phe Asp Val Glu
  1               5                  10                  15

Glu His Leu Pro Gly Ile Ser Asp Ser Phe Val Asp Trp Val Thr Gly
             20                  25                  30

Gln Ile Trp Glu Leu Pro Pro Glu Ser Asp Leu Asn Leu Thr Leu Val
         35                  40                  45

Glu Gln Pro Gln Leu Thr Val Ala Asp Arg Ile Arg Arg Val Phe Leu
     50                  55                  60

Tyr Glu Trp Asn Lys Phe Ser Lys Gln Glu Ser Lys Phe Phe Val Gln
 65                  70                  75                  80

Phe Glu Lys Gly Ser Glu Tyr Phe His Leu His Thr Leu Val Glu Thr
                 85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Gly Ala Asn Lys Val
    130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
            180                 185                 190

Ser Ser Gln Arg Ser Gln Glu Ala Ala Ser Gln Arg Glu Phe Ser Ala
        195                 200                 205

Asp Pro Val Ile Lys Ser Lys Thr Ser Gln Lys Tyr Met Ala Leu Val
    210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Thr Lys Ile Met Ser Leu
            260                 265                 270

Thr Lys Ser Ala Val Asp Tyr Leu Val Gly Ser Ser Val Pro Glu Asp
        275                 280                 285

Ile Ser Lys Asn Arg Ile Trp Gln Ile Phe Glu Met Asn Gly Tyr Asp
    290                 295                 300

Pro Ala Tyr Ala Gly Ser Ile Leu Tyr Gly Trp Cys Gln Arg Ser Phe
```

```
                305                 310                 315                 320
Asn Lys Arg Asn Thr Val Trp Leu Tyr Gly Pro Ala Thr Thr Gly Lys
            325                 330                 335

Thr Asn Ile Ala Glu Ala Ile Ala His Thr Val Pro Phe Tyr Gly Cys
        340                 345                 350

Val Asn Trp Thr Asn Glu Asn Phe Pro Phe Asn Asp Cys Val Asp Lys
        355                 360                 365

Met Leu Ile Trp Trp Glu Glu Gly Lys Met Thr Asn Lys Val Val Glu
    370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
            405                 410                 415

Asn Thr Asn Met Cys Val Val Asp Gly Asn Ser Thr Thr Phe Glu
        420                 425                 430

His Gln Gln Pro Leu Glu Asp Arg Met Phe Lys Phe Glu Leu Thr Lys
        435                 440                 445

Arg Leu Pro Pro Asp Phe Gly Lys Ile Thr Lys Gln Glu Val Lys Asp
450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
            485                 490                 495

Lys Arg Pro Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
            515                 520                 525

Val Thr Val Asp Pro Ala Pro Leu Arg Pro Leu Asn Trp Asn Ser Arg
        530                 535                 540

Leu Val Gly Arg Ser Trp
545                 550

<210> SEQ ID NO 15
<211> LENGTH: 1690
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 15
attctttgct ctggactgct agaggaccct cgctgccatg gctaccttct atgaagtcat    60
tgttcgcgtc ccatttgacg tggaggaaca tctgcctgga atttctgaca gctttgtgga   120
ctgggtaact ggtcaaattt gggagctgcc tccagagtca gatttaaatt tgactctggt   180
tgaacagcct cagttgacgg tggctgatag aattcgccgc gtgttcctgt acgagtggaa   240
caaattttcc aagcaggagt ccaaattctt tgtgcagttt gaaaagggat ctgaatattt   300
tcatctgcac acgcttgtgg agacctccgg catctcttcc atggtcctcg gccgctacgt   360
gagtcagatt cgcgcccagc tggtgaaagt ggtcttccag ggaattgaac cccagatcaa   420
cgactgggtc gccatcacca aggtaaagaa gggcggagcc aataaggtgg tggattctgg   480
gtatattccc gcctacctgc tgccgaaggt ccaaccggag cttcagtggg cgtggacaaa   540
cctggacgag tataaattgg ccgccctgaa tctggaggag cgcaaacggc tcgtcgcgca   600
gtttctggca gaatcctcgc agcgctcgca ggaggcggct tcgcagcgtg agttctcggc   660
```

```
tgacccggtc atcaaaagca agacttccca gaaatacatg gcgctcgtca actggctcgt    720
ggagcacggc atcacttccg agaagcagtg gatccaggaa atcaggaga gctacctctc    780 cttcaactcc accggcaact ctcggagcca gatcaaggcc gcgctcgaca acgcgaccaa    840
aattatgagt ctgacaaaaa gcgcggtgga ctacctcgtg gggagctccg ttcccgagga    900
catttcaaaa aacagaatct ggcaaatttt tgagatgaat ggctacgacc cggcctacgc    960
gggatccatc ctctacggct ggtgtcagcg ctccttcaac aagaggaaca ccgtctggct   1020
ctacggaccc gccacgaccg gcaagaccaa catcgcggag gccatcgccc acactgtgcc   1080
cttttacggc tgcgtgaact ggaccaatga aaactttccc tttaatgact gtgtggacaa   1140
aatgctcatt tggtgggagg agggaaagat gaccaacaag gtggttgaat ccgccaaggc   1200
catcctgggg ggctcaaagg tgcgggtcga tcagaaatgt aaatcctctg ttcaaattga   1260 ttctaccccct gtcattgtaa cttccaatac aaacatgtgt gtggtggtgg atgggaattc   1320
cacgaccttt gaacaccagc agccgctgga ggaccgcatg ttcaaatttg aactgactaa   1380
gcggctcccg ccagattttg caagattac taagcaggaa gtcaaggact tttttgcttg   1440
ggcaaaggtc aatcaggtgc cggtgactca cgagtttaaa gttcccaggg aattggcggg   1500
aactaagggg gcggagaaat ctctaaaacg cccactgggt gacgtcacca atactagcta   1560
taaaagtctg gagaagcggg ccaggctctc atttgttccc gagacgcctc gcagttcaga   1620
cgtgactgtt gatcccgctc ctctgcgacc gctcaattgg aattcaagat tggttggaag   1680
aagttggtga                                                         1690
```

<210> SEQ ID NO 16
<211> LENGTH: 145
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 16

```
ccatcaccaa ggtaaagaag ggcggagcca ataaggtggt ggattctggg tatattcccg     60
cctacctgct gccgaaggtc caaccggagc ttcagtgggc gtggacaaac ctggacgagt    120
ataaattggc cgccctgaat ctgga                                         145
```

<210> SEQ ID NO 17
<211> LENGTH: 174
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 17

```
taagcaggaa gtcaaggact tttttgcttg ggcaaaggtc aatcaggtgc cggtgactca     60
cgagtttaaa gttcccaggg aattggcggg aactaagggg gcggagaaat ctctaaaacg    120
cccactgggt gacgtcacca atactagcta taaaagtctg gagaagcggg ccag          174
```

<210> SEQ ID NO 18
<211> LENGTH: 187
<212> TYPE: DNA
<213> ORGANISM: Artificial Sequence
<220> FEATURE:
<223> OTHER INFORMATION: Description of Artificial Sequence:/Note = synthetic construct

```
<400> SEQUENCE: 18
cactctcaag caagggggtt ttgtaagcag tgatgtcata atgatgtaat gcttattgtc    60
acgcgatagt taatgattaa cagtcatgtg atgtgtttta tccaatagga agaaagcgcg   120
cgtatgagtt ctcgcgagac ttccggggta taaaagaccg agtgaacgag cccgccgcca   180
ttctttg                                                            187

<210> SEQ ID NO 19
<211> LENGTH: 168
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 19
aaacctcctt gcttgagagt gtggcactct ccccctgtc gcgttcgctc gctcgctggc    60
tcgtttgggg gggtggcagc tcaaagagct gccagacgac ggccctctgg ccgtcgcccc   120
cccaaacgag ccagcgagcg agcgaacgcg acagggggga gagtgcca               168

<210> SEQ ID NO 20
<211> LENGTH: 168
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 20
aaacctcctt gcttgagagt gtggcactct ccccctgtc gcgttcgctc gctcgctggc    60
tcgtttgggg gggcgacggc cagagggccg tcgtctgccg gctctttgag ctgccacccc   120
cccaaacgag ccagcgagcg agcgaacgcg acagggggga gagtgcca               168

<210> SEQ ID NO 21
<211> LENGTH: 8
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 21 cggtgtga                                                             8

<210> SEQ ID NO 22
<211> LENGTH: 8
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 22 cggttgag                                                             8

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:/Note =
      synthetic construct
```

<400> SEQUENCE: 23
caaaacctcc ttgcttgaga g                                           21

<210> SEQ ID NO 24
<211> LENGTH: 4675
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 24

| | | | | | |
|---|---|---|---|---|---|
| ttggccactc | cctctctgcg | cgctcgctcg | ctcactgagg | ccgggcgacc | aaaggtcgcc | 60 |
| cgacgcccgg | gctttgcccg | ggcggcctca | gtgagcgagc | gagcgcgcag | agagggagtg | 120 |
| gccaactcca | tcactagggg | ttcctggagg | ggtggagtcg | tgacgtgaat | tacgtcatag | 180 |
| ggttagggag | gtcctgtatt | agaggtcacg | tgagtgtttt | gcgacatttt | gcgacaccat | 240 |
| gtggtcacgc | tgggtattta | agcccgagtg | agcacgcagg | gtctccattt | tgaagcggga | 300 |
| ggtttgaacg | cgcagccgcc | atgccggggt | tttacgagat | tgtgattaag | gtccccagcg | 360 |
| accttgacgg | gcatctgccc | ggcatttctg | acagctttgt | gaactgggtg | ccgagaagg | 420 |
| aatgggagtt | gccgccagat | tctgacatgg | atctgaatct | gattgagcag | gcaccccctga | 480 |
| ccgtggccga | gaagctgcag | cgcgactttc | tgacggaatg | gcgccgtgtg | agtaaggccc | 540 |
| cggaggcct | tttctttgtg | caatttgaga | agggagagag | ctacttccac | atgcacgtgc | 600 |
| tcgtggaaac | caccggggtg | aaatccatgg | ttttgggacg | tttcctgagt | cagattcgcg | 660 |
| aaaaactgat | tcagagaatt | taccgcggga | tcgagccgac | tttgccaaac | tggttcgcgg | 720 |
| tcacaaagac | cagaaatggc | gccggaggcg | ggaacaaggt | ggtggatgag | tgctacatcc | 780 |
| ccaattactt | gctccccaaa | acccagcctg | agctccagtg | ggcgtggact | aatatggaac | 840 |
| agtatttaag | cgcctgtttg | aatctcacgg | agcgtaaacg | gttggtggcg | cagcatctga | 900 |
| cgcacgtgtc | gcagacgcag | gagcagaaca | aagagaatca | gaatcccaat | tctgatgcgc | 960 |
| cggtgatcag | atcaaaaact | tcagccaggt | acatggagct | ggtcgggtgg | ctcgtggaca | 1020 |
| aggggattac | ctcggagaag | cagtggatcc | aggaggacca | ggcctcatac | atctccttca | 1080 |
| atgcggcctc | caactcgcgg | tcccaaatca | aggctgcctt | ggacaatgcg | ggaaagatta | 1140 |
| tgagcctgac | taaaaccgcc | cccgactacc | tggtgggcca | gcagcccgtg | gaggacattt | 1200 |
| ccagcaatcg | gatttataaa | attttggaac | taaacgggta | cgatccccaa | tatgcggctt | 1260 |
| ccgtctttct | gggatgggcc | acgaaaaagt | tcggcaagag | gaacaccatc | tggctgtttg | 1320 |
| ggcctgcaac | taccgggaag | accaacatcg | cggaggccat | agcccacact | gtgcccttct | 1380 |
| acgggtgcgt | aaactggacc | aatgagaact | ttcccttcaa | cgactgtgtc | gacaagatgg | 1440 |
| tgatctggtg | ggaggagggg | aagatgaccg | ccaaggtcgt | ggagtcggcc | aaagccattc | 1500 |
| tcggaggaag | caaggtgcgc | gtggaccaga | aatgcaagtc | ctcggcccag | atagacccga | 1560 |
| ctcccgtgat | cgtcacctcc | aacaccaaca | tgtgcgccgt | gattgacggg | aactcaacga | 1620 |
| ccttcgaaca | ccagcagccc | ttgcaagacc | ggatgttcaa | atttgaactc | acccgccgtc | 1680 |
| tggatcatga | ctttgggaag | gtcaccaagc | aggaagtcaa | agacttttc | cggtgggcaa | 1740 |
| aggatcacgt | ggttgaggtg | gagcatgaat | tctacgtcaa | aaagggtgga | gccaagaaaa | 1800 |
| gacccgcccc | cagtgacgca | gatataagtg | agcccaaacg | ggtgcgcgag | tcagttgcgc | 1860 |
| agccatcgac | gtcagacgcg | gaagcttcga | tcaactacgc | agacaggtac | caaaacaaat | 1920 |

```
gttctcgtca cgtgggcatg aatctgatgc tgtttccctg cagacaatgc gagagaatga    1980
atcagaattc aaatatctgc ttcactcacg acagaaaga ctgtttagag tgctttcccg     2040
tgtcagaatc tcaacccgtt tctgtcgtca aaaggcgta tcagaaactg tgctacattc     2100
atcatatcat gggaaaggtg ccagacgctt gcactgcctg cgatctggtc aatgtggatt    2160
tggatgactg catctttgaa caataaatga tttaaatcag gtatggctgc cgatggttat    2220
cttccagatt ggctcgagga cactctctct gaaggaataa gacagtggtg gaagctcaaa    2280
cctggcccac caccaccaaa gcccgcagag cggcataagg acgacagcag gggtcttgtg    2340
cttcctgggt acaagtacct cggacccttc aacggactcg acaagggaga gccggtcaac    2400
gaggcagacg ccgcggccct cgagcacgta caaagcctac gaccggcagc tcgacagcgg    2460
agacaacccg tacctcaagt acaaccacgc cgacgcggag tttcaggagc gccttaaaga    2520
agatacgtct tttgggggca acctcggacg agcagtcttc caggcgaaaa agagggttct    2580
tgaacctctg ggcctggttg aggaacctgt taagacggct ccgggaaaaa agaggccggt    2640
agagcactct cctgtggagc cagactcctc ctcgggaacc ggaaaggcgg gccagcagcc    2700
tgcaagaaaa agattgaatt ttggtcagac tggagacgca gactcagtac ctgaccccca    2760
gcctctcgga cagccaccag cagcccctc tggtctggga actaatacga tggctacagg    2820
cagtggcgca ccaatggcag acaataacga gggcgccgac ggagtgggta attcctccgg    2880
aaattggcat tgcgattcca catggatggg cgacagagtc atcaccacca gcacccgaac    2940
ctgggccctg cccacctaca caaccacct ctacaaacaa atttccagcc aatcaggagc    3000
ctcgaacgac aatcactact ttggctacag cacccctgg gggtattttg acttcaacag    3060
attccactgc cacttttcac cacgtgactg gcaaagactc atcaacaaca actggggatt    3120
ccgacccaag agactcaact tcaagctctt taacattcaa gtcaaagagg tcacgcagaa    3180
tgacggtacg acgacgattg ccaataacct taccagcacg gttcaggtgt ttactgactc    3240
ggagtaccag ctcccgtacg tcctcggctc ggcgcatcaa ggatgcctcc cgccgttccc    3300
agcagacgtc ttcatggtgc cacagtatgg atacctcacc ctgaacaacg ggagtcaggc    3360
agtaggacgc tcttcatttt actgcctgga gtactttcct tctcagatgc tgcgtaccgg    3420
aaacaacttt accttcagct acacttttga ggacgttcct ttccacagca gctacgctca    3480
cagccagagt ctggaccgtc tcatgaatcc tctcatcgac cagtacctgt attacttgag    3540
cagaacaaac actccaagtg aaccaccac gcagtcaagg cttcagtttt ctcaggccgg    3600
agcgagtgac attcgggacc agtctaggaa ctggcttcct ggaccctgtt accgccagca    3660
gcgagtatca aagacatctg cggataacaa caacagtgaa tactcgtgga ctggagctac    3720
caagtaccac ctcaatggca gagactctct ggtgaatccg gccatggcaa gccacaagga    3780
cgatgaagaa aagtttttc ctcagagcgg ggttctcatc tttgggaagc aaggctcaga    3840
gaaaacaaat gtgaacattg aaaaggtcat gattacagac gaagaggaaa tcggaacaac    3900
caatcccgtg gctacggagc agtatggttc tgtatctacc aacctccaga gaggcaacag    3960
acaagcagct accgcagatg tcaacacaca aggcgttctt ccaggcatgg tctggcagga    4020
cagagatgtg taccttcagg ggcccatctg gcaaagatt ccacacacgg acggacattt    4080
tcacccctct cccctcatgg gtggattcgg acttaaacac cctcctccac agattctcat    4140
caagaacacc ccggtacctg cgaatccttc gaccacttc agtgcggcaa gtttgcttc     4200
cttcatcaca cagtactcca cgggacacgg tcagcgtgga gatcgagtgg gagctgcaga    4260
```

-continued

```
aggaaaacag caaacgctgg aatcccgaaa ttcagtacac ttccaactac aacaagtctg    4320
ttaatcgtgg acttaccgtg gatactaatg gcgtgtattc agagcctcgc cccattggca    4380
ccagatacct gactcgtaat ctgtaattgc ttgttaatca ataaaccgtt taattcgttt    4440
cagttgaact ttggtctctg cgtatttctt tcttatctag tttccatggc tacgtagata    4500
agtagcatgg cgggttaatc attaactaca aggaacccct agtgatggag ttggccactc    4560
cctctctgcg cgctcgctcg ctcactgagg ccgggcgacc aaaggtcgcc cgacgcccgg    4620
gctttgcccg ggcggcctca gtgagcgagc gagcgcgcag agagggagtg gccaa         4675
```

<210> SEQ ID NO 25
<211> LENGTH: 735
<212> TYPE: PRT
<213> ORGANISM: Artificial Sequence
<220> FEATURE:
<223> OTHER INFORMATION: Description of Artificial Sequence; Note = synthetic construct

<400> SEQUENCE: 25

```
Met Ala Ala Asp Gly Tyr Leu Pro Asp Trp Leu Glu Asp Thr Leu Ser
 1               5                  10                  15

Glu Gly Ile Arg Gln Trp Trp Lys Leu Lys Pro Gly Pro Pro Pro
                20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285
```

```
Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
    595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
```

```
                705                 710                 715                 720
Ser Glu Pro Arg Pro Ile Gly Thr Arg Tyr Leu Thr Arg Asn Leu
                    725                 730                 735

<210> SEQ ID NO 26
<211> LENGTH: 621
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 26

Met Pro Gly Phe Tyr Glu Ile Val Ile Lys Val Pro Ser Asp Leu Asp
 1               5                  10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
        50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335
```

-continued

```
Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
        530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
            565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
    610                 615                 620
```

AAV5 VECTOR FOR TRANSDUCING BRAIN CELLS AND LUNG CELLS

BACKGROUND OF THE INVENTION

1. Field of the Invention

The present invention provides adeno-associated virus 5 (AAV5) and vectors derived therefrom. Thus, the present invention relates to AAV5 vectors for and methods of delivering nucleic acids to cells of subjects. More specifically, the present invention provides methods of delivering nucleic acids to cerebellar cells, ependymal cells, neurons astrocytes, airway epithelial cells and alveolar cells of subjects. More particularly, the invention provides methods of delivering nucleic acids to cerebellar cells, ependymal cells and alveolar cells.

2. Background Art

Adeno associated virus (AAV) is a small nonpathogenic virus of the parvoviridae family (for review see 28). AAV is distinct from the other members of this family by its dependence upon a helper virus for replication. In the absence of a helper virus, AAV has been shown to integrate in a locus specific manner into the q arm of chromosome 19 (21). The approximately 5 kb genome of AAV consists of one segment of single stranded DNA of either plus or minus polarity. Physically, the parvovirus virion is nonenveloped and its icosohedral capsid is approximately 20–25 nm in diameter.

To date 8 serologically distinct AAVs have been identified and 6 have been isolated from humans or primates and are referred to as AAV types 1–6 (1). The most extensively studied of these isolates is AAV type 2 (AAV2). The genome of AAV2 is 4680 nucleotides in length and contains two open reading frames (ORFs), the right ORF and the left ORF. The left ORF encodes the non-structural Rep proteins, Rep40, Rep52, Rep68 and Rep78, which are involved in regulation of replication and transcription in addition to the production of single-stranded progeny genomes (5–8, 11, 12, 15, 17, 19, 21–23, 25, 34, 37–40). Furthermore, two of the Rep proteins have been associated with the preferential integration of AAV genomes into a region of the q arm of human chromosome 19. Rep68/78 have also been shown to possess NTP binding activity as well as DNA and RNA helicase activities. The Rep proteins possess a nuclear localization signal as well as several potential phosphorylation sites. Mutation of one of these kinase sites resulted in a loss of replication activity.

The ends of the genome are short inverted terminal repeats which have the potential to fold into T-shaped hairpin structures that serve as the origin of viral DNA replication. Within the ITR region two elements have been described which are central to the function of the ITR, a GAGC repeat motif and the terminal resolution site (TRS). The repeat motif has been shown to bind Rep when the ITR is in either a linear or hairpin conformation (7, 8, 26).

This binding serves to position Rep68/78 for cleavage at the TRS which occurs in a site- and strand-specific manner. In addition to their role in replication, these two elements appear to be central to viral integration. Contained within the chromosome 19 integration locus is a Rep binding site with an adjacent TRS. These elements have been shown to be functional and necessary for locus specific integration.

The AAV2 virion is a non-enveloped, icosohedral particle approximately 20–25 nm in diameter. The capsid is composed of three related proteins referred to as VP 1,2 and 3 which are encoded by the right ORF. These proteins are found in a ratio of 1:1:10 respectively. The capsid proteins differ from each other by the use of alternative splicing and an unusual start codon. Deletion analysis of has shown that removal or alteration of AAV2 VP1 which is translated from an alternatively spliced message results in a reduced yield of infections particles (15, 16, 38). Mutations within the VP3 coding region result in the failure to produce any single-stranded progeny DNA or infectious particles (15, 16, 38).

The following features of the characterized AAVs have made them attractive vectors for gene transfer (16). AAV vectors have been shown in vitro to stably integrate into the cellular genome; possess a broad host range; transduce both dividing and non dividing cells in vitro and in vivo (13, 20, 30, 32) and maintain high levels of expression of the transduced genes (41). Viral particles are heat stable, resistant to solvents, detergents, changes in pH, temperature, and can be concentrated on CsCl gradients (1,2). Integration of AAV provirus is not associated with any long term negative effects on cell growth or differentiation (3,42). The ITRs have been shown to be the only cis elements required for replication, packaging and integration (35) and may contain some promoter activities (14).

AAV2 was originally thought to infect primate and non-primate cell types provided the appropriate helper virus was present. However, the inability of AAV2 to infect certain cell types is now known to be due to the particular cellular tropism exhibited by the AAV2 virus. Recent work has shown that some cell lines are transduced very poorly by AAV2 (30). Binding studies have indicated that heparin sulfate proteoglycans are necessary for high efficiency transduction with AAV2. AAV5 is a unique member of the parvovirus family. The present DNA hybridization data indicate a low level of homology with the published AAV1–4 sequences (31). The present invention shows that, unlike AAV2, AAV5 transduction is not effected by heparin as AAV2 is and therefore will not be restricted to the same cell types as AAV2.

The present invention provides a vector comprising the AAV5 virus or a vector comprising subparts of the virus, as well as AAV5 viral particles. While AAV5 is similar to AAV2, the two viruses are found herein to be physically and genetically distinct. These differences endow AAV5 with some unique properties and advantages which better suit it as a vector for gene therapy. For example, one of the limiting features of using AAV2 as a vector for gene therapy is production of large amounts of virus. Using standard production techniques, AAV5 is produced at a 10–50 fold higher level compared to AAV2. Because of its unique TRS site and rep proteins, AAV5 should also have a distinct integration locus compared to AAV2.

Furthermore, as shown herein, AAV5 capsid protein, again surprisingly, is distinct from AAV2 capsid protein and exhibits different tissue tropism, thus making AAV5 capsid-containing particles suitable for transducing cell types for which AAV2 is unsuited or less well-suited. AAV2 and AAV5 have been shown to be serologically distinct and thus, in a gene therapy application, AAV5, and AAV5-derived vectors, would allow for transduction of a patient who already possess neutralizing antibodies to AAV2 either as a result of natural immunological defense or from prior exposure to AAV2 vectors. Another advantage of AAV5 is that AAV5 cannot be rescued by other serotypes. Only AAV5 can rescue the integrated AAV5 genome and effect replication, thus avoiding unintended replication of AAV5 caused by other AAV serotypes. Thus, the present invention, by providing these new recombinant vectors and particles based on AAV5 provides a new and highly useful series of vectors.

SUMMARY OF THE INVENTION

The present invention provides methods of delivering a nucleic acid to specific regions, tissues and cell types of the central nervous system (CNS) such as ependymal cells, cerebellar cells, neurons, and astrocytes. In particular, the nucleic acids are delivered to specific regions and cells of the brain, particulary, ependymal cells and cerebellar cells.

The present invention also provides methods of delivering a nucleic acid to lung cells such as alveolar cells.

The present invention provides a nucleic acid vector comprising a pair of adeno-associated virus 5 (AAV5) inverted terminal repeats and a promoter between the inverted terminal repeats.

The present invention further provides an AAV5 particle containing a vector comprising a pair of AAV2, AAV4 or AAV5 inverted terminal repeats.

Additionally, the instant invention provides an isolated nucleic acid comprising the nucleotide sequence set forth in SEQ ID NO:1 (AAV5 genome). Furthermore, the present invention provides an isolated nucleic acid consisting essentially of the nucleotide sequence set forth in SEQ ID NO:1 (AAV5 genome).

The present invention provides an isolated nucleic acid encoding an AAV5 Rep protein, for example, the nucleic acid as set forth in SEQ ID NO:10. Additionally provided is an isolated full-length AAV5 Rep protein or a unique fragment thereof. Additionally provided is an isolated AAV5 Rep 40 protein having the amino acid sequence set forth in SEQ ID NO:12, or a unique fragment thereof Additionally provided is an isolated AAV5 Rep 52 protein having the amino acid sequence set forth in SEQ ID NO:2, or a unique fragment thereof. Additionally provided is an isolated AAV5 Rep 68 protein, having the amino acid sequence set forth in SEQ ID NO:14 or a unique fragment thereof. Additionally provided is an isolated AAV5 Rep 78 protein having the amino acid sequence set forth in SEQ ID NO:3, or a unique fragment thereof. The sequences for these proteins are provided below in the Sequence Listing and elsewhere in the application where the proteins are described.

The present invention further provides an isolated AAV5 capsid protein, VP1, having the amino acid sequence set forth in SEQ ID NO:4, or a unique fragment thereof. Additionally provided is an isolated AAV5 capsid protein, VP2, having the amino acid sequence set forth in SEQ ID NO:5, or a unique fragment thereof. Also provided is an isolated AAV5 capsid protein, VP3, having the amino acid sequence set forth in SEQ ID NO:6, or a unique fragment thereof.

The present invention additionally provides an isolated nucleic acid encoding AAV5 capsid protein, for example, the nucleic acid set forth in SEQ ID NO:7, or a unique fragment thereof.

The present invention provides an isolated nucleic acid encoding an AAV5 inverted terminal repeat, for example, the nucleic acid set forth in SEQ ID NO: 19 or SEQ ID NO: 20, or a unique fragment thereof.

The present invention further provides an AAV5 particle comprising a capsid protein consisting essentially of the amino acid sequence set forth in SEQ ID NO:4, or a unique fragment thereof.

Additionally provided by the present invention is an isolated nucleic acid comprising an AAV5 p5 promoter having the nucleic acid sequence set forth in SEQ ID NO: 18, or a unique fragment thereof.

The instant invention provides a method of screening a cell for infectivity by AAV5 comprising contacting the cell with AAV5 and detecting the presence of AAV5 in the cells.

The present invention further provides a method of delivering a nucleic acid to a cell comprising administering to the cell an AAV5 particle containing a vector comprising the nucleic acid inserted between a pair of AAV inverted terminal repeats, thereby delivering the nucleic acid to the cell.

The present invention also provides a method of delivering a nucleic acid to a subject comprising administering to a cell from the subject an AAV5 particle comprising the nucleic acid inserted between a pair of AAV inverted terminal repeats, and returning the cell to the subject, thereby delivering the nucleic acid to the subject.

The present invention also provides a method of delivering a nucleic acid to a cell in a subject comprising administering to the subject an AAV5 particle comprising the nucleic acid inserted between a pair of AAV inverted terminal repeats, thereby delivering the nucleic acid to a cell in the subject.

The instant invention further provides a method of delivering a nucleic acid to a cell in a subject having antibodies to AAV2 comprising administering to the subject an AAV5 particle comprising the nucleic acid, thereby delivering the nucleic acid to a cell in the subject.

BRIEF DESCRIPTION OF THE DRAWINGS

FIG. 4 is a sequence comparison of the AAV2 genome (SEQ ID NO: 24) and the AAV5 genome (SEQ ID NO: 1).

FIG. 5 is a sequence comparison of the AAV2 VP1 capsid protein (SEQ ID NO: 25) and the AAV5 VP1 capsid protein (SEQ ID NO: 4).

FIG. 6 is a sequence comparison of the AAV2 rep 78 protein (SEQ ID NO: 26) and the AAV5 rep 78 protein (SE ID NO: 3).

FIG. 15E shows the quantitative β-gal activity of airway epithelia infected the different recombinant AAV serotypes (AAV2/βGal, AAV4/βGal, and AAV5/βGal). Data are the mean β-gal activity per mg protein±SEM (n=4–12). Asterisk indicates p<0.01.

Asterisk indicates p<0.01.

Figure 19A:
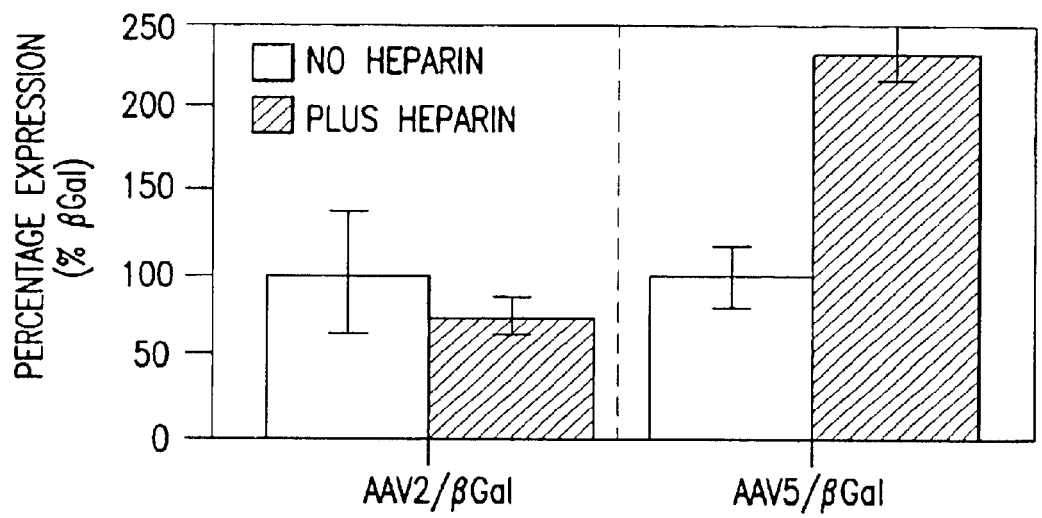

FIGS. 19A,B shows the effect of soluble heparin on AAV gene transfer to human airway epithelia. To compete off AAV binding and gene transfer, in some conditions the viruses were pretreated with 20 μg/ml of soluble heparin for 30 min. FIG. 19A shows the effect of heparin on AAV gene transfer to human airway epithelia from the apical side and FIG. 5B from the basolateral side. Five hundred particles per cell of either AAV2/βGal or AAV5/βGal were added for 30 min at 4° C. β-galactosidase was measured 14 days later. Data are mean±SEM, n=8 in each group. Asterisk in FIG. 19B indicates p=0.018.

Figure 20A:
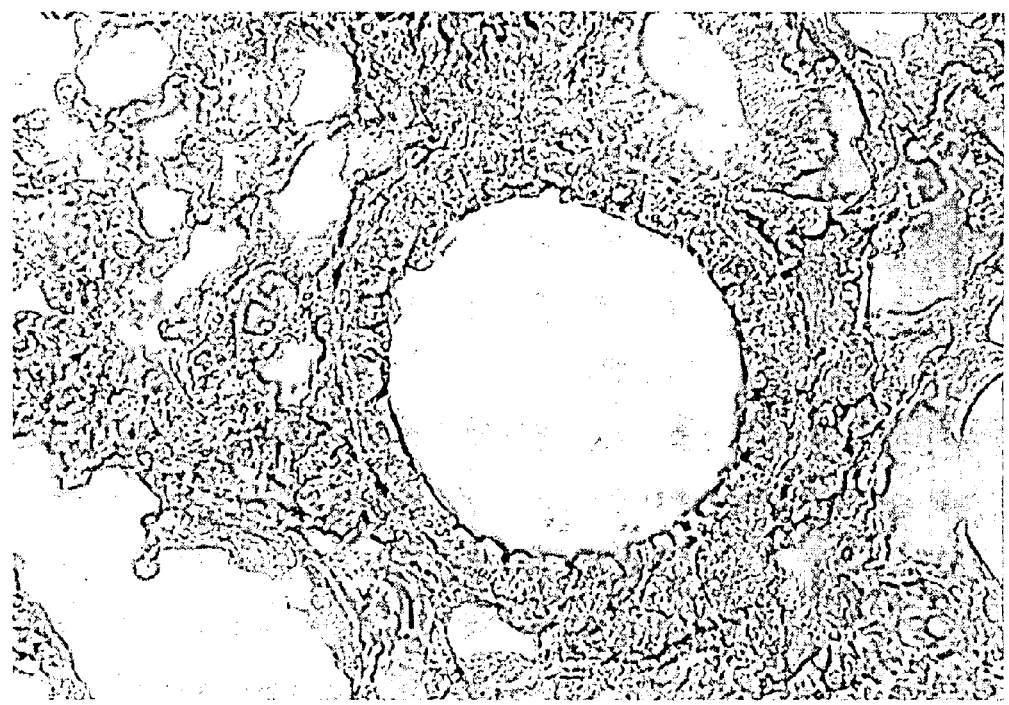
Figure 20B:
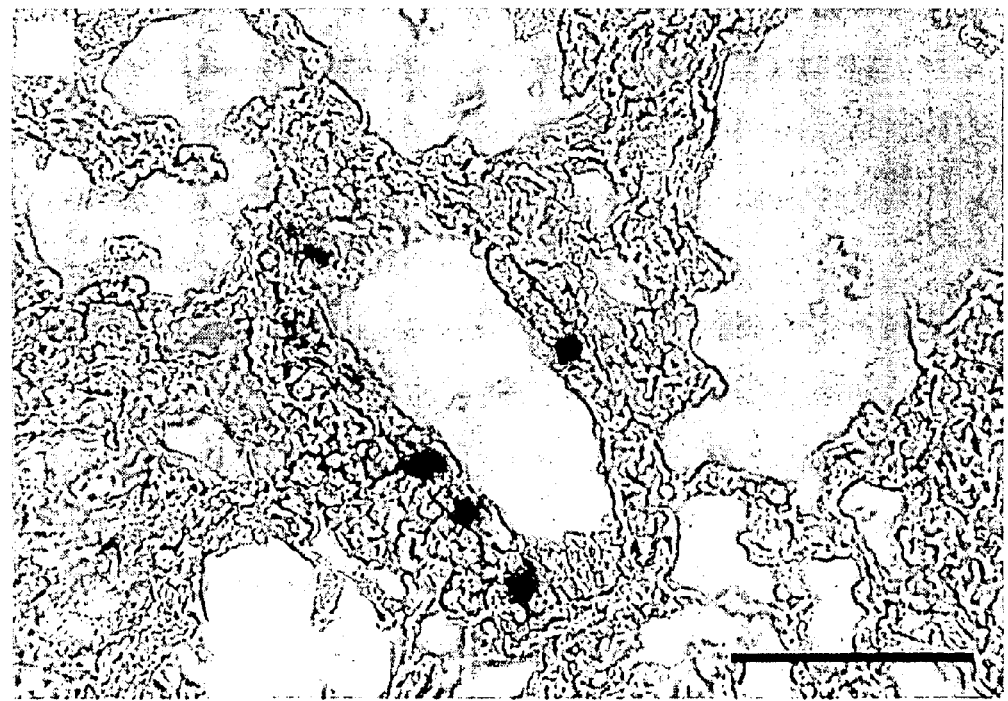
Figure 20C:
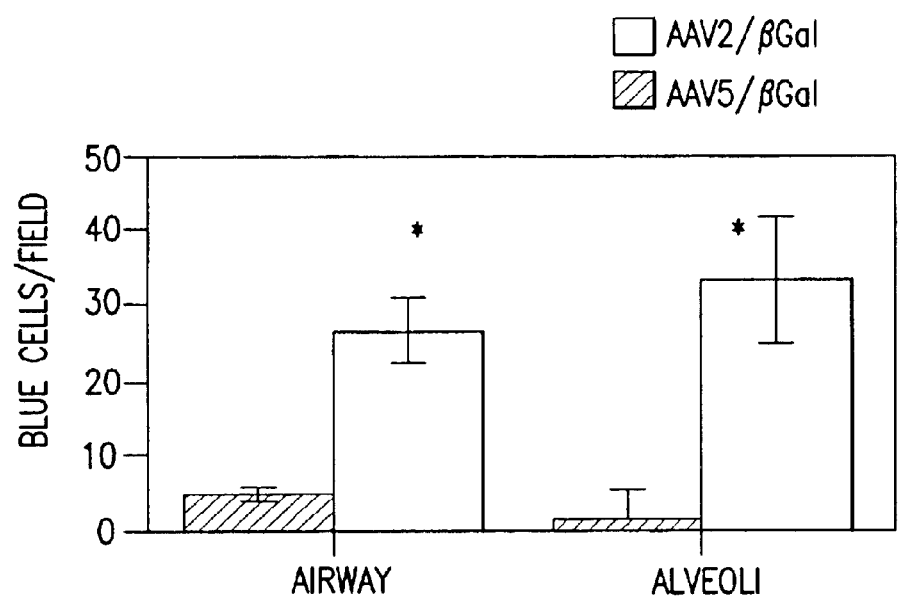

FIGS. 20A-C shows the AAV5/βGal-mediated gene transfer to murine conducting airway epithelia, and alveolar epithelia in vivo. Mice were exposed to $1\times10^{10}$ particles of either AAV2/βGal or AAV5/βGal via nasal instillation. After 30 days the mice were sacrificed, the lungs were fixed and stained with X-Gal. FIGS. 20 A,B shows representative photomicrographs showing ciliated and non-ciliated cells transduced by AAV2/βGal (A) and AAV5/βGal (B). FIG. 20C shows quantitation of gene transfer by number of blue nuclei of βgal-expressing bronchial and alveolar cells per microscopic field. n=5 mice per group. Asterisk indicates p<0.01.

Figure 21:

FIG. 21 shows a sagittal section of a mouse cerebellum injected with AAV5 expressing nuclear targeted β-galactosidase driven off an RSV promoter. At 7 weeks postinjection, the animal was deeply anesthetized and s transcardially perfused with 4% paraformaldehyde. Cerebellum was sectioned at 50 mm thickness and sections were processed for X-gal histochemistry. AAV5 transduced large numbers of Purkinje cells, stellate and basket neurons and a smaller number of Golgi neurons.

Figure 22:
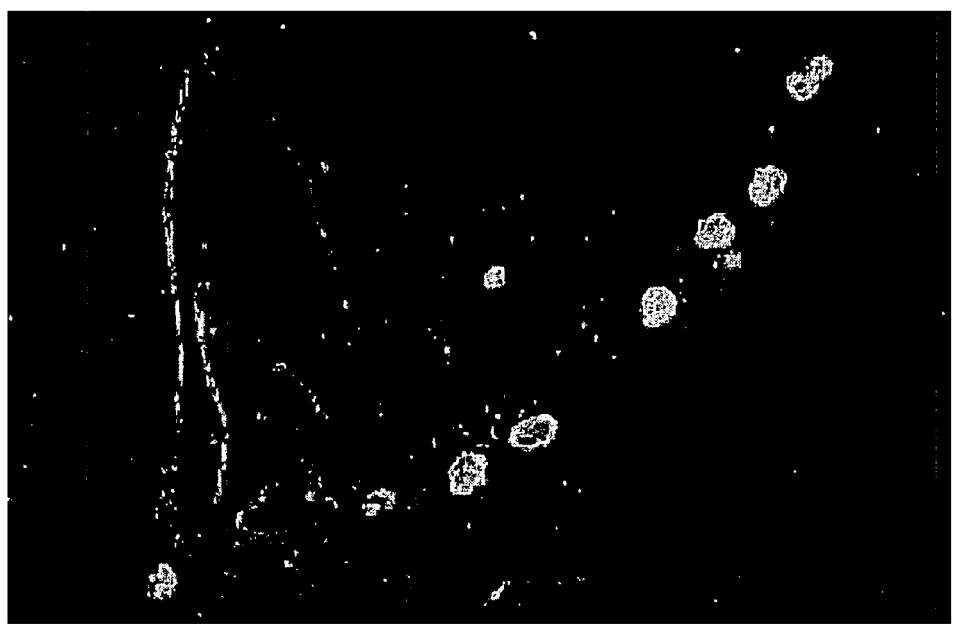

FIG. 22 -double label immunofluorescence showed that within the cerebellar cortex AAV5 transduced neurons but not glia. This section is from the same animal as A and processed with antibodies against glial fibrillary acid protein (GFAP) which is red and β-galactosidase which fluoresces green. Arrow points to a typical β-galactosidase positive cell. Confocal microscopy shows that there is no colocalization between GFAF and AAV5 β-galactosidase. Thus all cells which are transduced are nonglial (neurons).

Figure 23:
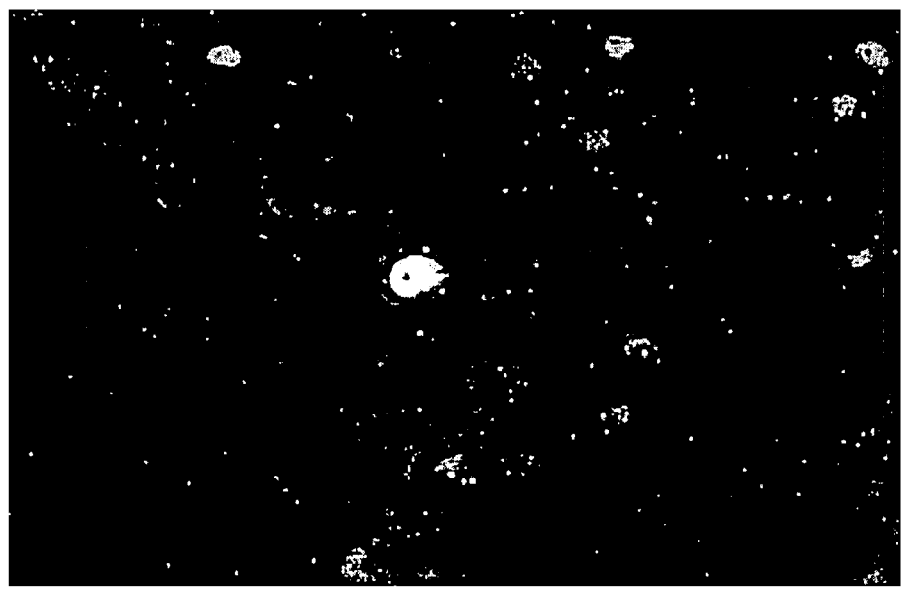

FIG. 23 shows a third cerebellar section from the same animal as FIG. 21 and FIG. 22 which was processed for double label immunofluorescence with antibodies against calbindin (red) and β-galactosidase (green). Calbindin is expressed in Purkinje cells but not other cerebellar neurons. Confocal microscopy showed strong colocalization between calbindin and the AAV5 expressed β-galactosidase in the Purkine cell monolayer (arrow). However there were many β-galactosidase positive neurons in molecular layer and granule cell layer (example arrowhead) that did not express calbindin, confirming that several classes of neurons had been transduced.

DETAILED DESCRIPTION OF THE INVENTION

As used in the specification and in the claims, "a" can mean one or more, depending upon the context in which it is used. The terms "having" and "comprising" are used interchangeably herein, and signify open ended meaning.

The present application provides a recombinant adeno-associated virus 5 (AAV5). This virus has one or more of the characteristics described below. The compositions of the present invention do not include wild-type AAV5. The methods of the present invention can use either wild-type AAV5 or recombinant AAV5-based delivery.

The present invention provides novel AAV5 particles, recombinant AAV5 vectors, recombinant AAV5 virions and novel AAV5 nucleic acids and polypeptides.

An AAV5 particle is a viral particle comprising an AAV5 capsid protein. A recombinant AAV5 vector is a nucleic acid construct that comprises at least one unique nucleic acid of AAV5. A recombinant AAV5 virion is a particle containing a recombinant AAV5 vector, wherin the particle can be either an AAV5 particle as described herein or a non-AAV5 particle. Alternatively, the recombinant AAV5 virion is an AAV5 particle containing a recombinant vector, wherein the vector can be either an AAV5 vector as described herein or a non-AAV5 vector. These vectors, particles, virions, nucleic acids and polypeptides are described below.

The present invention provides the nucleotide sequence of the AAV5 genome and vectors and particles derived therefrom. Specifically, the present invention provides a nucleic acid vector comprising a pair of AAV5 inverted terminal repeats (ITRs) and a promoter between the inverted terminal repeats. While the rep proteins of AAV2 and AAV5 will bind to either a type 2 ITR or a type 5 ITR, efficient genome replication only occurs when type 2 Rep replicates a type 2 ITR and a type 5 Rep replicates a type 5 ITR. This specificity is the result of a difference in DNA cleavage specificity of the two Reps which is necessary for replication. AAV5 Rep cleaves at CGGT^GTGA (SEQ ID NO: 21) and AAV2 Rep cleaves at CGGT^TGAG (SEQ ID NO: 22) (Chiorini et al., 1999. J. Virol. 73 (5) 4293–4298). Mapping of the AAV5 ITR terminal resolution site (TRS) identified this distinct cleavage site, CGGT^GTGA, which is absent from the ITRs of other AAV serotypes. Therefore, the minimum sequence necessary to distinguish AAV5 from AAV2 is the TRS site where Rep cleaves in order to replicate the virus. Examples of the type 5 ITRs are shown in SEQ ID NO: 19 and SEQ ID NO: 20, AAV5 ITR "flip" and AAV5 "flop", respectively. Minor modifications in an ITR of either orientation are contemplated and are those that will not interfere with the hairpin structure formed by the AAV5 ITR as described herein. Furthermore, to be considered within the term "AAV5 ITR" the nucleotide sequence must retain one or more features described herein that distinguish the AAV5 ITR from the ITRs of other serotypes, e.g. it must retain the Rep binding site described herein.

The D– region of the AAV5 ITR (SEQ ID NO: 23), a single stranded region of the ITR, inboard of the TRS site, has been shown to bind a factor which depending on its phosphorylation state correlates with the conversion of the AAV from a single stranded genome to a transcriptionally active form that allows for expression of the viral DNA. This region is conserved between AAV2, 3, 4, and 6 but is divergent in AAV5. The D+ region is the reverse complement of the D– region.

The promoter can be any desired promoter, selected by known considerations, such as the level of expression of a nucleic acid functionally linked to the promoter and the cell type in which the vector is to be used. That is, the promoter can be tissue/cell-specific. Promoters can be prokaryotic, eukaryotic, fungal, nuclear, mitochondrial, viral or plant promoters. Promoters can be exogenous or endogenous to the cell type being transduced by the vector. Promoters can include, for example, bacterial promoters, known strong promoters such as SV40 or the inducible metallothionein promoter, or an AAV promoter, such as an AAV p5 promoter. Additionally, chimeric regulatory promoters for targeted gene expression can be utilized. Examples of these regulatory systems, which are known in the art, include the tetracycline based regulatory system which utilizes the tet transactivator protein (tTA), a chimeric protein containing the VP 16 activation domain fused to the tet repressor of *Escherichia coli*, the IPTG based regulatory system, the CID based regulatory system, and the Ecdysone based regulatory system (44). Other promoters include promoters derived from actin genes, immunoglobulin genes, cytomegalovirus (CMV), adenovirus, bovine papilloma virus, adenoviral promoters, such as the adenoviral major late promoter, an inducible heat shock promoter, respiratory syncytial virus, Rous sarcomas virus (RSV), etc., specifically, the promoter can be AAV2 p5 promoter or AAV5 p5 promoter. More specifically, the AAV5 p5 promoter can be about same location in SEQ ID NO: 1 as the AAV2 p5 promoter, in the corresponding AAV2 published sequence. An example of an AAV5 p5 promoter is nucleotides 220–338 of SEQ ID NO: 1. Additionally, the p5 promoter may be enhanced by nucleotides 1–130 of SEQ ID NO:1. Furthermore, smaller fragments of p5 promoter that retain promoter activity can readily be determined by standard procedures including, for example, constructing a series of deletions in the p5 promoter, linking the deletion to a reporter gene, and determining whether the reporter gene is expressed, i.e., transcribed and/or translated. The promoter can be the promoter of any of the AAV serotypes, and can be the p19 promoter (SEQ ID NO: 16) or the p40 promoter set forth in the sequence listing as SEQ ID NO: 17.

It should be recognized that any errors in any of the nucleotide sequences disclosed herein can be corrected, for example, by using the hybridization procedure described below with various probes derived from the described sequences such that the coding sequence can be reisolated and resequenced. Rapid screening for point mutations can also be achieved with the use of polymerase chain reaction-single strand conformation polymorphism PCR-SSCP) (43). The corresponding amino acid sequence can then be corrected accordingly.

The AAV5-derived vector of the invention can further comprise a heterologous nucleic acid functionally linked to the promoter. By "heterologous nucleic acid" is meant that any heterologous or exogenous nucleic acid, i.e. not normally found in wild-type AAV5 can be inserted into the vector for transfer into a cell, tissue or organism. By "functionally linked" is meant that the promoter can promote expression of the heterologous nucleic acid, as is known in the art, and can include the appropriate orientation of the promoter relative to the heterologous nucleic acid. Furthermore, the heterologous nucleic acid preferably has all appropriate sequences for expression of the nucleic acid. The nucleic acid can include, for example, expression control sequences, such as an enhancer, and necessary information processing sites, such as ribosome binding sites, RNA splice sites, polyadenylation sites, and transcriptional terminator sequences.

The heterologous nucleic acid can encode beneficial proteins or polypeptides that replace missing or defective proteins required by the cell or subject into which the vector is transferred or can encode a cytotoxic polypeptide that can be directed, e.g., to cancer cells or other cells whose death would be beneficial to the subject. The heterologous nucleic acid can also encode antisense RNAs that can bind to, and thereby inactivate, mRNAs made by the subject that encode harmful proteins. The heterologous nucleic acid can also encode ribozymes that can effect the sequence-specific inhibition of gene expression by the cleavage of mRNAs. In one embodiment, antisense polynucleotides can be produced from a heterologous expression cassette in an AAV5 vector construct where the expression cassette contains a sequence that promotes cell-type specific expression (Wirak et al., *EMBO* 10:289 (1991)). For general methods relating to antisense polynucleotides, see *Antisense RNA and DNA*, D. A. Melton, Ed., Cold Spring Harbor Laboratory, Cold Spring Harbor, N.Y. (1988).

Examples of heterologous nucleic acids which can be administered to a cell or subject as part of the present AAV5 vector can include, but are not limited to the following: nucleic acids encoding secretory and nonsecretory proteins, nucleic acids encoding therapeutic agents, such as tumor necrosis factors (TNF), such as TNF-α; interferons, such as interferon-α, interferon-β, and interferon-γ; interleukins, such as IL-1, IL-1β, and ILs -2 through -14; GM-CSF; adenosine deaminase; cellular growth factors, such as lymphokines; soluble CD4; Factor VIII; Factor IX; T-cell receptors; LDL receptor; ApoE; ApoC; alpha-1 antitrypsin; ornithine transcarbamylase (OTC); cystic fibrosis transmembrane receptor (CFTR); insulin; anti-apoptotic gene products; proteins promoting neuronal survival, such as growth factors and glutamate receptors; Fc receptors for antigen binding domains of antibodies, such as immunoglobulins; anti-HIV decoy tar elements; and antisense sequences which inhibit viral replication, such as antisense sequences which inhibit replication of hepatitis B or hepatitis non-A, non-B virus. The nucleic acid is chosen considering several factors, including the cell to be transfected. Where the target cell is a blood cell, for example, particularly useful nucleic acids to use are those which allow the blood cells to exert a therapeutic effect, such as a gene encoding a clotting factor for use in treatment of hemophilia. Another target cell is the lung airway cell, which can be used to administer nucleic acids, such as those coding for the cystic fibrosis transmembrane receptor, which could provide a gene therapeutic treatment for cystic fibrosis. Other target cells include muscle cells where useful nucleic acids, such as those encoding cytokines and growth factors, can be transduced and the protein the nucleic acid encodes can be expressed and secreted to exert its effects on other cells, tissues and organs, such as the liver. Furthermore, the nucleic acid can encode more than one gene product, limited only, if the nucleic acid is to be packaged in a capsid, by the size of nucleic acid that can be packaged.

Furthermore, suitable nucleic acids can include those that, when transferred into a primary cell, such as a blood cell, cause the transferred cell to target a site in the body where that cell's presence would be beneficial. For example, blood cells such as TIL cells can be modified, such as by transfer into the cell of a Fab portion of a monoclonal antibody, to recognize a selected antigen. Another example would be to introduce a nucleic acid that would target a therapeutic blood cell to tumor cells. Nucleic acids useful in treating cancer cells include those encoding chemotactic factors which cause an inflammatory response at a specific site, thereby having a therapeutic effect.

Cells, particularly blood cells, muscle cells, airway epithelial cells, brain cells and endothelial cells having such nucleic acids transferred into them can be useful in a variety of diseases, syndromes and conditions. For example, suitable nucleic acids include nucleic acids encoding soluble CD4, used in the treatment of AIDS and α-antitrypsin, used in the treatment of emphysema caused by a-antitrypsin deficiency. Other diseases, syndromes and conditions in which such cells can be useful include, for example, adenosine deaminase deficiency, sickle cell deficiency, brain disorders such as Alzheimer's disease, Huntington's disease, lysosomal storage diseases, Gaucher's disease, Hurler's disease, Krabbe's disease, motor neuron diseases such as amylotrophic lateral sclerosis and dominant spinal cerebellar ataxias (examples include SCA1, SCA2, and SCA3), thalassemia, hemophilia, diabetes, phenylketonuria, growth disorders and heart diseases, such as those caused by alterations in cholesterol metabolism, and defects of the immune system.

As another example, hepatocytes can be transfected with the present vectors having useful nucleic acids to treat liver disease. For example, a nucleic acid encoding OTC can be used to transfect hepatocytes (ex vivo and returned to the liver or in vivo) to treat congenital hyperammonemia, caused by an inherited deficiency in OTC. Another example is to use a nucleic acid encoding LDL to target hepatocytes ex vivo or in vivo to treat inherited LDL receptor deficiency. Such transfected hepatocytes can also be used to treat acquired infectious diseases, such as diseases resulting from a viral infection. For example, transduced hepatocyte precursors can be used to treat viral hepatitis, such as hepatitis B and non-A, non-B hepatitis, for example by transducing the hepatocyte precursor with a nucleic acid encoding an antisense RNA that inhibits viral replication. Another example includes transferring a vector of the present invention having a nucleic acid encoding a protein, such as α-interferon, which can confer resistance to the hepatitis virus.

For a procedure using transfected hepatocytes or hepatocyte precursors, hepatocyte precursors having a vector of the present invention transferred in can be grown in tissue culture, removed from the tissue culture vessel, and introduced to the body, such as by a surgical method. In this example, the tissue would be placed directly into the liver, or into the body cavity in proximity to the liver, as in a transplant or graft. Alternatively, the cells can simply be directly injected into the liver, into the portal circulatory system, or into the spleen, from which the cells can be transported to the liver via the circulatory system. Furthermore, the cells can be attached to a support, such as microcarrier beads, which can then be introduced, such as by injection, into the peritoneal cavity. Once the cells are in the liver, by whatever means, the cells can then express the nucleic acid and/or differentiate into mature hepatocytes which can express the nucleic acid.

The AAV5-derived vector can include any normally occurring AAV5 sequences in addition to an ITR and promoter. Examples of vector constructs are provided below.

The present vector or AAV5 particle or recombinant AAV5 virion can utilize any unique fragment of the present AAV5 nucleic acids, including the AAV5 nucleic acids set forth in SEQ ID NOS: 1 and 7–11, 13, 15, 16, 17, and 18. To be unique, the fragment must be of sufficient size to distinguish it from other known sequences, most readily determined by comparing any nucleic acid fragment to the nucleotide sequences of nucleic acids in computer databases, such as GenBank. Such comparative searches are standard in the art. Typically, a unique fragment useful as a primer or probe will be at least about 8 or 10, preferable at least 20 or 25 nucleotides in length, depending upon the specific nucleotide content of the sequence. Additionally, fragments can be, for example, at least about 30, 40, 50, 75, 100, 200 or 500 nucleotides in length and can encode polypeptides or be probes. The nucleic acid can be single or double stranded, depending upon the purpose for which it is intended. Where desired, the nucleic acid can be RNA.

The present invention further provides an isolated AAV5 capsid protein to contain the vector. In particular, the present invention provides not only a polypeptide comprising all three AAV5 coat proteins, i.e., VP1, VP2 and VP3, but also a polypeptide comprising each AAV5 coat protein individually, SEQ ID NOS: 4, 5, and 6, respectively. Thus an AAV5 particle comprising an AAV5 capsid protein comprises at least one AAV5 coat protein VP1, VP2 or VP3. An AAV5 particle comprising an AAV5 capsid protein can be utilized to deliver a nucleic acid vector to a cell, tissue or subject. For example, the herein described AAV5 vectors can be encapsidated in an AAV5 capsid-derived particle and utilized in a gene delivery method. Furthermore, other viral nucleic acids can be encapsidated in the AAV5 particle and utilized in such delivery methods. For example, an AAV1, 2,3,4, or 6 vector (e.g. AAV1,2,3,4, or 6 ITR and nucleic acid of interest) can be encapsidated in an AAV5 particle and administered. Furthermore, an AAV5 chimeric capsid incorporating both AAV2 capsid and AAV5 capsid sequences can be generated, by standard cloning methods, selecting regions from the known sequences of each protein as desired. For example, particularly antigenic regions of the AAV2 capsid protein can be replaced with the corresponding region of the AAV5 capsid protein. In addition to chimeric capsids incorporating AAV2 capsid sequences, chimeric capsids incorporating AAV1, 3, 4, or 6 and AAV5 capsid sequences can be generated, by standard cloning methods, selecting regions from the known sequences of each protein as desired.

The capsids can also be modified to alter their specific tropism by genetically altering the capsid to encode a specific ligand to a cell surface receptor. Alternatively, the capsid can be chemically modified by conjugating a ligand to a cell surface receptor. By genetically or chemically altering the capsids, the tropism can be modified to direct AAV5 to a particular cell or population of cells. The capsids can also be altered immunologically by conjugating the capsid to an antibody that recognizes a specific protein on the target cell or population of cells.

The capsids can also be assembled into empty particles by expression in mammalian, bacterial, fungal or insect cells. For example, AAV2 particles are known to be made from VP3 and VP2 capsid proteins in baculovirus. The same basic protocol can produce an empty AAV5 particle comprising an AAV5 capsid protein.

The herein described recombinant AAV5 nucleic acid derived vector can be encapsidated in an AAV particle. In particular, it can be encapsidated in an AAV1 particle, an AAV2 particle, an AAV3 particle, an AAV4 particle, an AAV5 particle or an AAV6 particle, a portion of any of these capsids, or a chimeric capsid particle as described above, by standard methods using the appropriate capsid proteins in the encapsidation process, as long as the nucleic acid vector fits within the size limitation of the particle utilized. The encapsidation process itself is standard in the art. The AAV5 replication machinery, i.e. the rep initiator proteins and other functions required for replication, can be utilized to produce the AAV5 genome that can be packaged in an AAV1, 2, 3, 4, 5 or 6 capsid.

The recombinant AAV5 virion containing a vector can also be produced by recombinant methods utilizing multiple plasmids. In one example, the AAV5 rep nucleic acid would be cloned into one plasmid, the AAV5 ITR nucleic acid would be cloned into another plasmid and the AAV1, 2, 3, 4, 5 or 6 capsid nucleic acid would be cloned on another plasmid. These plasmids would then be introduced into cells. The cells that were efficiently transduced by all three plasmids, would exhibit specific integration as well as the ability to produce recombinant AAV5 virion. Additionally, two plasmids could be used where the AAV5 rep nucleic acid would be cloned into one plasmid and the AAV5 ITR and AAV5 capsid would be cloned into another plasmid. These plasmids would then be introduced into cells. The cells that were efficiently transduced by both plasmids, would exhibit specific integration as well as the ability to produce recombinant AAV5 virion.

An AAV5 capsid polypeptide encoding the entire VP1, VP2, and VP3 polypeptide can have greater than 56% overall homology to the polypeptide having the amino acid sequence encoded by nucleotides in SEQ ID NOS:7,8 and 9, as shown in FIGS. 4 and 5. The capsid protein can have about 70% homology, about 75% homology, 80% homology, 85% homology, 90% homology, 95% homology, 98% homology, 99% homology, or even 100% homology to the protein having the amino acid sequence encoded by the nucleotides set forth in SEQ ID NOS:7, 8 or 9. The percent homology used to identify proteins herein, can be based on a nucleotide-by-nucleotide comparison or more preferable is based on a computerized algorithm as described herein. Variations in the amino acid sequence of the AAV5 capsid protein are contemplated herein, as long as the resulting particle comprising an AAV5 capsid protein remains antigenically or immunologically distinct from AAV1, AAV2, AAV3, AAV4 or AAV6 capsid, as can be routinely determined by standard methods.

Specifically, for example, ELISA and Western blots can be used to determine whether a viral particle is antigenically or immunologically distinct from AAV2 or the other serotypes. Furthermore, the AAV5 particle preferably retains tissue tropism distinction from AAV2, such as that exemplified in the examples herein, An AAV5 chimeric particle comprising at least one AAV5 coat protein may have a different tissue tropism from that of an AAV5 particle consisting only of AAV5 coat proteins, but is still distinct from the tropism of an AAV2 particle, in that it will infect some cells not infected by AAV2 or an AAV2 particle.

The invention further provides a recombinant AAV5 virion, comprising an AAV5 particle containing, i.e., encapsidating, a vector comprising a pair of AAV5 inverted terminal repeats. The recombinant vector can further comprise an AAV5 Rep-encoding nucleic acid. The vector encapsidated in the particle can further comprise an exogenous nucleic acid inserted between the inverted terminal repeats. AAV5 Rep confers targeted integration and efficient replication, thus production of recombinant AAV5, comprising AAV5 Rep, yields more particles than production of recombinant AAV2. Since AAV5 is more efficient at replicating and packaging its genome, the exogenous nucleic acid inserted, or in the AAV5 capsids of the present invention, between the inverted terminal repeats can be packaged in the AAV1, 2, 3, 4, or 6 capsids to achieve the specific tissue tropism conferred by the capsid proteins.

The invention further contemplates chimeric recombinant ITRs that contains a rep binding site and a TRS site recognized by that Rep protein. By "Rep protein" is meant all four of the Rep proteins, Rep 40, Rep 78, Rep 52, Rep 68. Alternatively, "Rep protein" could be one or more of the Rep proteins described herein. One example of a chimeric ITR would consist of an AAV5 D region (SEQ ID NO: 23), an AAV5 TRS site (SEQ ID NO: 21), an AAV2 hairpin and an AAV2 binding site. Another example would be an AAV5 D region, an AAV5 TRS site, an AAV3 hairpin and an AAV3 binding site. In these chimeric ITRs, the D region can be from AAV1, 2, 3, 4, 5 or 6. The hairpin can be derived from AAV 1,2 3, 4, 5, 6. The binding site can be derived from any of AAV1, 2, 3, 4, 5 or 6. Preferably, the D region and the TRS are from the same serotype.

The chimeric ITRs can be combined with AAV5 Rep protein and any of the AAV serotype capsids to obtain recombinant virion. For example, recombinant virion can be produced by an AAV5 D region, an AAV5 TRS site, an AAV2 hairpin, an AAV2 binding site, AAV5 Rep protein and AAV1 capsid. This recombinant virion would possess the cellular tropism conferred by the AAV1 capsid protein and would possess the efficient replication conferred by the AAV5 Rep.

Other examples of the ITR, Rep protein and Capsids that will produce recombinant virion are provided in the list below:

5ITR+5Rep+5Cap=virion
5ITR+5Rep+1Cap=virion
5ITR+5Rep+2Cap=virion
5ITR+5Rep+3Cap=virion
5ITR+5Rep+4Cap=virion
5ITR+5Rep+6Cap=virion
1ITR+1Rep+5Cap=virion
2ITR+2Rep+5Cap=virion
3ITR+3Rep+5Cap=virion
4ITR+4Rep+5Cap=virion
6ITR+6Rep+5Cap=virion In any of the constructs described herein, inclusion of a promoter is preferred. As used in the constructs herein, unless otherwise specified, Cap (capsid) refers to any of AAV5 VP1, AAV5 VP2, AAV5 VP3, combinations thereof, functional fragments of any of VP1, VP2 or VP3, or chimeric capsids as described herein. The ITRs of the constructs described herein, can be chimeric recombinant ITRs as described elsewhere in the application.

Conjugates of recombinant or wild-type AAV5 virions and nucleic acids or proteins can be used to deliver those molecules to a cell. For example, the purified AAV5 can be used as a vehicle for delivering DNA bound to the exterior of the virus. Examples of this are to conjugate the DNA to the virion by a bridge using poly-L-lysine or other charged molecule. Also contemplated are virosomes that contain AAV5 structural proteins (AAV5 capsid proteins), lipids such as DOTAP, and nucleic acids that are complexed via charge interaction to introduce DNA into cells.

Also provided by this invention are conjugates that utilize the AAV5 capsid or a unique region of the AAV5 capsid protein (e.g. VP1, VP2 or VP3 or combinations thereof) to introduce DNA into cells. For example, the type 5 VP3 protein or fragment thereof, can be conjugated to a DNA on a plasmid that is conjugated to a lipid. Cells can be infected using the targeting ability of the VP3 capsid protein to achieve the desired tissue tropism, specific to AAV5. Type 5 VP1 and VP2 proteins can also be utilized to introduce DNA or other molecules into cells. By further incorporating the Rep protein and the AAV TRS into the DNA-containing conjugate, cells can be transduced and targeted integration can be achieved. For example, if AAV5 specific targeted integration is desired, a conjugate composed of the AAV5 VP3 capsid, AAV5 rep or a fragment of AAV5 rep, AAV5 TRS, the rep binding site, the heterologous DNA of interest, and a lipid, can be utilized to achieve AAV5 specific tropism and AAV5 specific targeted integration in the genome.

Further provided by this invention are chimeric viruses where AAV5 can be combined with herpes virus, herpes virus amplicons, baculovirus or other viruses to achieve a desired tropism associated with another virus. For example, the AAV5 ITRs could be inserted in the herpes virus and cells could be infected. Post-infection, the ITRs of AAV5 could be acted on by AAV5 rep provided in the system or in a separate vehicle to rescue AAV5 from the genome. Therefore, the cellular tropism of the herpes simplex virus can be combined with AAV5 rep mediated targeted integration. Other viruses that could be utilized to construct chimeric viruses include, lentivirus, retrovirus, pseudotyped retroviral vectors, and adenoviral vectors.

The present invention farther provides isolated nucleic acids of AAV5. For example, provided is an isolated nucleic acid comprising the nucleotide sequence set forth in SEQ ID NO:1 (AAV5 genome). This nucleic acid, or portions thereof, can be inserted into vectors, such as plasmids, yeast artificial chromosomes, or other viral vector (particle), if desired, by standard cloning methods. The present invention also provides an isolated nucleic acid consisting essentially of the nucleotide sequence set forth in SEQ ID NO:1. The nucleotides of SEQ ID NO:1 can have minor modifications and still be contemplated by the present invention. For example, modifications that do not alter the amino acid encoded by any given codon (such as by modification of the third, "wobble," position in a codon) can readily be made, and such alterations are known in the art. Furthermore, modifications that cause a resulting neutral (conserved) amino acid substitution of a similar amino acid can be made in a coding region of the genome. Additionally, modifications as described herein for the AAV5 components, such as the ITRs, the p5 promoter, etc. are contemplated in this invention. Furthermore, modifications to regions of SEQ ID NO:1 other than in the ITR, TRS Rep binding site and hairpin are likely to be tolerated without serious impact on the function of the nucleic acid as a recombinant vector.

As used herein, the term "isolated" refers to a nucleic acid separated or significantly free from at least some of the other components of the naturally occurring organism, for example, the cell structural components or viral components commonly found associated with nucleic acids in the environment of the virus and/or other nucleic acids. The isolation of the native nucleic acids can be accomplished, for example, by techniques such as cell lysis followed by phenol plus chloroform extraction, followed by ethanol precipitation of the nucleic acids. The nucleic acids of this invention can be isolated from cells according to any of many methods well known in the art.

As used herein, the term "nucleic acid" refers to single-or multiple stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for any of the novel genes discussed herein or may include alternative codons which encode the same amino acid as those provided herein, including that which is found in the naturally occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides).

The present invention additionally provides an isolated nucleic acid that selectively hybridizes with any nucleic acid disclosed herein, including the entire AAV5 genome and any unique fragment thereof, including the Rep and capsid encoding sequences (e.g. SEQ ID NOS: 1, 7, 8, 9, 10, 11, 13, 15, 16, 17, 18, 19, 20, 21, 22 and 23). Specifically, the nucleic acid can selectively or specifically hybridize to an isolated nucleic acid consisting of the nucleotide sequence set forth in SEQ ID NO:1 (AAV5 genome). The present invention further provides an isolated nucleic acid that selectively or specifically hybridizes with an isolated nucleic acid comprising the nucleotide sequence set forth in SEQ ID NO:1 (AAV5 genome). By "selectively hybridizes" as used herein is meant a nucleic acid that hybridizes to one of the disclosed nucleic acids under sufficient stringency conditions without significant hybridization to a nucleic acid encoding an unrelated protein, and particularly, without detectably hybridizing to nucleic acids of AAV2. Thus, a nucleic acid that selectively hybridizes with a nucleic acid of the present invention will not selectively hybridize under stringent conditions with a nucleic acid encoding a different protein or the corresponding protein from a different serotype of the virus, and vice versa. A "specifically hybridizing" nucleic acid is one that hybridizes under stringent conditions to only a nucleic acid found in AAV5. Therefore, nucleic acids for use, for example, as primers and probes to detect or amplify the target nucleic acids are contemplated herein. Nucleic acid fragments that selectively hybridize to any given nucleic acid can be used, e.g., as primers and or probes for further hybridization or for amplification methods (e.g., polymerase chain reaction (PCR), ligase chain reaction (LCR)). Additionally, for example, a primer or probe can be designed that selectively hybridizes with both AAV5 and a gene of interest carried within the AAV5 vector (i.e., a chimeric nucleic acid).

Stringency of hybridization is controlled by both temperature and salt concentration of either or both of the hybridization and washing steps. Typically, the stringency of hybridization to achieve selective hybridization involves hybridization in high ionic strength solution (6×SSC or 6×SSPE) at a temperature that is about 12–25° C. below the Tm (the melting temperature at which half of the molecules dissociate from their hybridization partners) followed by washing at a combination of temperature and salt concentration chosen so that the washing temperature is about 5° C. to 20° C. below the $T_m$. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The washing temperatures can be used as described above to achieve selective stringency, as is known in the art. (Sambrook et al., *Molecular Cloning: A Laboratory Manual,* 2nd Ed., Cold Spring Harbor Laboratory, Cold Spring Harbor, N.Y., 1989; Kunkel et al. *Methods Enzymol.* 1987:154:367, 1987). A preferable stringent hybridization condition for a DNA:DNA hybridization can be at about 68° C. (in aqueous solution) in 6× SSC or 6× SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

A nucleic acid that selectively hybridizes to any portion of the AAV5 genome is contemplated herein. Therefore, a nucleic acid that selectively hybridizes to AAV5 can be of longer length than the AAV5 genome, it can be about the same length as the AAV5 genome or it can be shorter than the AAV5 genome. The length of the nucleic acid is limited on the shorter end of the size range only by its specificity for hybridization to AAV5, i.e., once it is too short, typically less than about 5 to 7 nucleotides in length, it will no longer bind specifically to AAV5, but rather will hybridize to numerous background nucleic acids. Additionally contemplated by this invention is a nucleic acid that has a portion that specifically hybridizes to AAV5 and a portion that specifically hybridizes to a gene of interest inserted within AAV5.

The present invention further provides an isolated nucleic acid encoding an adeno-associated virus 5 Rep protein. The AAV5 Rep proteins are encoded by open reading frame (ORF) 1 of the AAV5 genome. Examples of the AAV5 Rep genes are shown in the nucleic acid set forth in SEQ ID NO:1, and include nucleic acids consisting essentially of the nucleotide sequences set forth in SEQ ID NOS:10 (Rep52), 11 (Rep78), 13 (Rep40), and 15 (Rep68), and nucleic acids comprising the nucleotide sequences set forth in SEQ ID NOS:10, 11, 13, and 15. However, the present invention contemplates that the Rep nucleic acid can include any one, two, three, or four of the four Rep proteins, in any order, in such a nucleic acid. Furthermore, minor modifications are contemplated in the nucleic acid, such as silent mutations in the coding sequences, mutations that make neutral or conservative changes in the encoded amino acid sequence, and mutations in regulatory regions that do not disrupt the expression of the gene. Examples of other minor modifications are known in the art. Further modifications can be made in the nucleic acid, such as to disrupt or alter expression of one or more of the Rep proteins in order to, for example, determine the effect of such a disruption; such as to mutate one or more of the Rep proteins to determine the resulting effect, etc. However, in general, a modified nucleic acid encoding a Rep protein will have at least about 85%, about 90%, about 93%, about 95%, about 98% or 100% homology to the Rep nucleic acid sequences described herein e.g., SEQ ID NOS: 10, 11, 13 and 15, and the Rep polypeptide encoded therein will have overall about 93%, about 95%, about 98%, about 99% or 100% homology with the amino acid sequence described herein, e.g., SEQ ID NOS:2, 3, 12 and 14. Percent homology is determined by the techniques described herein.

The present invention also provides an isolated nucleic acid that selectively or specifically hybridizes with a nucleic acid consisting essentially of the nucleotide sequence set forth in SEQ ID NOS:10, 11, 13 and 15, and an isolated nucleic acid that selectively hybridizes with a nucleic acid comprising the nucleotide sequence set forth in SEQ ID NOS:10, 11, 13 and 15. "Selectively hybridizing" and "stringency of hybridization" is defined elsewhere herein.

As described above, the present invention provides the nucleic acid encoding a Rep 40 protein and, in particular an isolated nucleic acid comprising the nucleotide sequence set forth in SEQ ID NO: 13, an isolated nucleic acid consisting essentially of the nucleotide sequence set forth in SEQ ID NO: 13, and a nucleic acid encoding the adeno-associated virus 5 protein having the amino acid sequence set forth in SEQ ID NO: 12. The present invention also provides the nucleic acid encoding a Rep 52 protein, and in particular an isolated nucleic acid comprising the nucleotide sequence set forth in SEQ ID NO:10, an isolated nucleic acid consisting essentially of the nucleotide sequence set forth in SEQ ID NO:10, and a nucleic acid encoding the adeno-associated virus 5 Rep protein having the amino acid sequence set forth in SEQ ID NO:2. The present invention further provides the nucleic acid encoding a Rep 68 protein and, in particular an isolated nucleic acid comprising the nucleotide sequence set forth in SEQ ID NO: 15, an isolated nucleic acid consisting essentially of the nucleotide sequence set forth in SEQ ID NO: 15, and a nucleic acid encoding the adeno-associated virus 5 protein having the amino acid sequence set forth in SEQ ID NO: 14. And, further, the present invention provides the nucleic acid encoding a Rep 78 protein, and in particular an isolated nucleic acid comprising the nucleotide sequence set forth in SEQ ID NO:11, an isolated nucleic acid consisting essentially of the nucleotide sequence set forth in SEQ ID NO:11, and a nucleic acid encoding the adeno-associated virus 5 Rep protein having the amino acid sequence set forth in SEQ ID NO:3. As described elsewhere herein, these nucleic acids can have minor modifications, including silent nucleotide substitutions, mutations causing conservative amino acid substitutions in the encoded proteins, and mutations in control regions that do not or minimally affect the encoded amino acid sequence.

The present invention further provides a nucleic acid encoding the entire AAV5 Capsid polypeptide. Furthermore, the present invention provides a nucleic acid encoding each of the three AAV5 coat proteins, VP1, VP2, and VP3. Thus, the present invention provides a nucleic acid encoding AAV5 VP1, a nucleic acid encoding AAV5 VP2, and a nucleic acid encoding AAV5 VP3. Thus, the present invention provides a nucleic acid encoding the amino acid sequence set forth in SEQ ID NO:4 (VP1); a nucleic acid encoding the amino acid sequence set forth in SEQ ID NO:5 (VP2), and a nucleic acid encoding the amino acid sequence set forth in SEQ ID NO:6 (VP3). The present invention also specifically provides a nucleic acid comprising SEQ ID NO:7 (VP1 gene); a nucleic acid comprising SEQ ID NO:8 (VP2 gene); and a nucleic acid comprising SEQ ID NO:9 (VP3 gene). The present invention also specifically provides a nucleic acid consisting essentially of SEQ ID NO:7 (VP1 gene), a nucleic acid consisting essentially of SEQ ID NO:8 (VP2 gene), and a nucleic acid consisting essentially of SEQ ID NO:9 (VP3 gene). Minor modifications in the nucleotide sequences encoding the capsid, or coat, proteins are contemplated, as described above for other AAV5 nucleic acids. However, in general, a modified nucleic acid encoding a capsid protein will have at least about 85%, about 90%, about 93%, about 95%, about 98% or 100% homology to the capsid nucleic sequences described herein e.g., SEQ ID NOS: 7, 8, and 9, and the capsid polypeptide encoded therein will have overall about 93%, about 95%, about 98%, about 99% or 100% homology with the amino acid sequence described herein, e.g., SEQ ID NOS:4, 5, and 6. Nucleic acids that selectively hybridize with the nucleic acids of SEQ ID NOS:7,8 and 9 under the conditions described above are also provided.

The present invention also provides a cell containing one or more of the herein described nucleic acids, such as the AAV5 genome, AAV5 ORF1 and ORF2, each AAV5 Rep protein gene, or each AAV5 capsid protein gene. Such a cell can be any desired cell and can be selected based upon the use intended. For example, cells can include bacterial cells, yeast cells, insect cells, human HeLa cells and simian Cos cells as well as other human and mammalian cells and cell lines. Primary cultures as well as established cultures and cell lines can be used. Nucleic acids of the present invention can be delivered into cells by any selected means, in particular depending upon the target cells. Many delivery means are well-known in the art. For example, electroporation, calcium phosphate precipitation, microinjection, cationic or anionic liposomes, and liposomes in combination with a nuclear localization signal peptide for delivery to the nucleus can be utilized, as is known in the art. Additionally, if the nucleic acids are in a viral particle, the cells can simply be transduced with the virion by standard means known in the art for AAV transduction. Small amounts of the recombinant AAV5 virus can be made to infect cells and produce more of itself.

The invention provides purified AAV5 polypeptides. The term "polypeptide" as used herein refers to a polymer of amino acids and includes full-length proteins and fragments thereof Thus, "protein," "polypeptide," and "peptide" are often used interchangeably herein. Substitutions can be selected by known parameters to be neutral (see, e.g., Robinson W E Jr, and Mitchell W M., AIDS 4:S151–S162 (1990)). As will be appreciated by those skilled in the art, the invention also includes those polypeptides having slight variations in amino acid sequences or other properties. Such variations may arise naturally as allelic variations (e.g., due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. Substitutions may be designed based on, for example, the model of Dayhoff, et al. (in *Atlas of Protein Sequence and Structure* 1978, Nat'l Biomed. Res. Found., Washington, D.C.). These modifications can result in changes in the amino acid sequence, provide silent mutations, modify a restriction site, or provide other specific mutations. The location of any modifications to the polypeptide will often determine its impact on function. Particularly, alterations in regions non-essential to protein function will be tolerated with fewer effects on function. Elsewhere in the application regions of the AAV5 proteins are described to provide guidance as to where substitutions, additions or deletions can be made to minimize the likelihood of disturbing the function of the variant.

A polypeptide of the present invention can be readily obtained by any of several means. For example, the polypeptide of interest can be synthesized chemically by standard methods. Additionally, the coding regions of the genes can be recombinantly expressed and the resulting polypeptide isolated by standard methods. Furthermore, an antibody specific for the resulting polypeptide can be raised by standard methods (see, e.g., Harlow and Lane, *Antibodies: A Laboratory Manual*, Cold Spring Harbor Laboratory, Cold Spring Harbor, N.Y., 1988), and the protein can be isolated from a cell expressing the nucleic acid encoding the polypeptide by selective hybridization with the antibody. This protein can be purified to the extent desired by standard methods of protein purification (see, e.g., Sambrook et al., *Molecular Cloning: A Laboratory Manual,* 2nd Ed., Cold Spring Harbor Laboratory, Cold Spring Harbor, N.Y., 1989).

Typically, to be unique, a polypeptide fragment of the present invention will be at least about 5 amino acids in length; however, unique fragments can be 6, 7, 8, 9, 10, 20, 30, 40, 50, 60, 70, 80, 90, 100 or more amino acids in length. A unique polypeptide will typically comprise such a unique fragment; however, a unique polypeptide can also be determined by its overall homology. A unique polypeptide can be 6, 7, 8, 9, 10, 20, 30, 40, 50, 60, 70, 80, 90, 100 or more amino acids in length. Uniqueness of a polypeptide fragment can readily be determined by standard methods such as searches of computer databases of known peptide or nucleic acid sequences or by hybridization studies to the nucleic acid encoding the protein or to the protein itself, as known in the art. The uniqueness of a polypeptide fragment can also be determined immunologically as well as functionally. Uniqueness can be simply determined in an amino acid-by-amino acid comparison of the polypeptides.

An antigenic or immunoreactive fragment of this invention is typically an amino acid sequence of at least about 5 consecutive amino acids, and it can be derived from the AAV5 polypeptide amino acid sequence. An antigenic AAV5 fragment is any fragment unique to the AAV5 protein, as described herein, against which an AAV5-specific antibody can be raised, by standard methods. Thus, the resulting antibody-antigen reaction should be specific for AAV5.

The present invention provides an isolated AAV5 Rep protein. An AAV5 Rep polypeptide is encoded by ORF1 of AAV5. The present invention also provides each individual AAV5 Rep protein. Thus the present invention provides AAV5 Rep 40 (e.g., SEQ ID NO: 12), or a unique fragment thereof. The present invention provides AAV5 Rep 52 (e.g., SEQ ID NO: 2), or a unique fragment thereof. The present invention provides AAV5 Rep 68 (e.g., SEQ ID NO: 14), or a unique fragment thereof. The present invention provides an example of AAV5 Rep 78 (e.g., SEQ ID NO: 3), or a unique fragment thereof. By "unique fragment thereof" is meant any smaller polypeptide fragment encoded by an AAV5 rep gene that is of sufficient length to be found only in the Rep polypeptide. Substitutions and modifications of the amino acid sequence can be made as described above and, farther, can include protein processing modifications, such as glycosylation, to the polypeptide.

The present invention further provides an AAV5 Capsid polypeptide or a unique fragment thereof. AAV5 capsid polypeptide is encoded by ORF 2 of AAV5. The present invention further provides the individual AAV5 capsid proteins, VP1, VP2 and VP3 or unique fragments thereof. Thus, the present invention provides an isolated polypeptide having the amino acid sequence set forth in SEQ ID NO:4 (VP1). The present invention additionally provides an isolated polypeptide having the amino acid sequence set forth in SEQ ID NO:5 (VP2). The present invention also provides an isolated polypeptide having the amino acid sequence set forth in SEQ ID NO:6 (VP3). By "unique fragment thereof" is meant any smaller polypeptide fragment encoded by any AAV5 capsid gene that is of sufficient length to be found only in the AAV5 capsid protein. Substitutions and modifications of the amino acid sequence can be made as described above and, further, can include protein processing modifications, such as glycosylation, to the polypeptide. However, an AAV5 Capsid polypeptide including all three coat proteins will have greater than about 56% overall homology to the polypeptide encoded by the nucleotides set forth in SEQ ID) NOS:4,5 or 6. The protein can have about 65%, about 70%, about 75%, about 80%, about 85%, about 90%, 93%, 95%, 97% or even 100% homology to the amino acid sequence encoded by the nucleotides set forth in SEQ ID NOS:4,5 or 6. An AAV5 VP1 polypeptide can have at least about 58%, about 60%, about 70%, about 80%, about 90%, 93%, 95%, 97% or about 100% homology to the amino acid sequence set forth in SEQ ID NO:4. An AAV5 VP2 polypeptide can have at least about 58%, about 60%, about 70%, about 80%, about 90%, 93%, 95%, 97% or about 100% homology to the amino acid sequence set forth in SEQ ID NO:5. An AAV5 VP3 polypeptide can have at least about 60%, about 70%, about 80%, about 90%, 93%, 95%, 97% or about 100% homology to the amino acid sequence set forth in SEQ ID NO:6.

The present invention further provides an isolated antibody that specifically binds an AAV5 Rep protein or a unique epitope thereof. Also provided are isolated antibodies that specifically bind the AAV5 Rep 52 protein, the AAV5 Rep 40 protein, the AAV5 Rep 68 protein and the AAV5 Rep 78 protein having the amino acid sequences set forth in SEQ ID NO:2, SEQ ID NO: 12, SEQ ID NO: 14 and SEQ ID NO: 3, respectively or that specifically binds a unique fragment thereof. Clearly, any given antibody can recognize and bind one of a number of possible epitopes present in the polypeptide; thus only a unique portion of a polypeptide (having the epitope) may need to be present in an assay to determine if the antibody specifically binds the polypeptide.

The present invention additionally provides an isolated antibody that specifically binds any of the adeno-associated virus 5 Capsid proteins (VP1, VP2 or VP3), a unique epitope thereof, or the polypeptide comprising all three AAV5 coat proteins. Also provided is an isolated antibody that specifically binds the AAV5 capsid protein having the amino acid sequence set forth in SEQ ID NO:4 (VP1), or that specifically binds a unique fragment thereof. The present invention further provides an isolated antibody that specifically binds the AAV5 Capsid protein having the amino acid sequence set forth in SEQ ID NO:5 (VP2), or that specifically binds a unique fragment thereof. The invention additionally provides an isolated antibody that specifically binds the AAV5 Capsid protein having the amino acid sequence set forth in SEQ ID NO:6 (VP3), or that specifically binds a unique fragment thereof Again, any given antibody can recognize and bind one of a number of possible epitopes present in the polypeptide; thus only a unique portion of a polypeptide (having the epitope) may need to be present in an assay to determine if the antibody specifically binds the polypeptide.

The antibody can be a component of a composition that comprises an antibody that specifically binds the AAV5 protein. The composition can further comprise, e.g., serum, serum-free medium, or a pharmaceutically acceptable carrier such as physiological saline, etc.

By "an antibody that specifically binds" an AAV5 polypeptide or protein is meant an antibody that selectively binds to an epitope on any portion of the AAV5 peptide such that the antibody binds specifically to the corresponding AAV5 polypeptide without significant background. Specific binding by an antibody further means that the antibody can be used to selectively remove the target polypeptide from a sample comprising the polypeptide or and can readily be determined by radioimmunoassay (RIA), bioassay, or enzyme-linked immunosorbant (ELISA) technology. An ELISA method effective for the detection of the specific antibody-antigen binding can, for example, be as follows: (1) bind the antibody to a substrate; (2) contact the bound antibody with a sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe the color change.

An antibody can include antibody fragments such as Fab fragments which retain the binding activity. Antibodies can be made as described in, e.g., Harlow and Lane, *Antibodies: A Laboratory Manual*, Cold Spring Harbor Laboratory, Cold Spring Harbor, N.Y. (1988). Briefly, purified antigen can be injected into an animal in an amount and in intervals sufficient to elicit an immune response. Antibodies can either be purified directly, or spleen cells can be obtained from the animal. The cells are then fused with an immortal cell line and screened for antibody secretion. Individual hybridomas are then propagated as individual clones serving as a source for a particular monoclonal antibody.

The present invention additionally provides a method of screening a cell for infectivity by AAV5 comprising contacting the cell with AAV5 and detecting the presence of AAV5 in the cells. AAV5 particles can be detected using any standard physical or biochemical methods. For example, physical methods that can be used for this detection include DNA based methods such as 1) polymerase chain reaction (PCR) for viral DNA or RNA or 2) direct hybridization with labeled probes, and immunological methods such as by 3) antibody directed against the viral structural or non-structural proteins. Catalytic methods of viral detection include, but are not limited to, detection of site and strand specific DNA nicking activity of Rep proteins or replication of an AAV origin-containing substrate. Reporter genes can also be utilized to detect cells that transduct AAV-5. For example, β-gal, green flourescent protein or luciferase can be inserted into a recombinant AAV-5. The cell can then be contacted with the recombinant AAV-5, either in vitro or in vivo and a colorimetric assay could detect a color change in the cells that would indicate transduction of AAV-5 in the cell. Additional detection methods are outlined in Fields, *Virology*, Raven Press, New York, N.Y. 1996.

For screening a cell for infectivity by AAV5, wherein the presence of AAV5 in the cells is determined by nucleic acid hybridization methods, a nucleic acid probe for such detection can comprise, for example, a unique fragment of any of the AAV5 nucleic acids provided herein. The uniqueness of any nucleic acid probe can readily be determined as described herein. Additionally, the presence of AAV5 in cells can be determined by flourescence, antibodies to gene products, focus forming assays, plaque lifts, Western blots and chromogenic assays. The nucleic acid can be, for example, the nucleic acid whose nucleotide sequence is set forth in SEQ ID NO: 1,7, 8, 9, 10, 11, 13, 15, 16, 17, 18, 19, 20, 21, 22, 23 or a unique fragment thereof.

The present invention includes a method of determining the suitability of an AAV5 vector for administration to a subject comprising administering to an antibody-containing sample from the subject an antigenic fragment of an isolated AAV5 Rep or Capsid protein, and detecting neutralizing antibody-antigen reaction in the sample, the presence of a neutralizing reaction indicating the AAV5 vector may be unsuitable for use in the subject. The present method of determining the suitability of an AAV5 vector for administration to a subject can comprise contacting an antibody-containing sample from the subject with a unique antigenic or immunogenic fragment of an AAV5 Rep protein (e.g. Rep 40, Rep 52, Rep 68, Rep 78) and detecting an antibody-antigen reaction in the sample, the presence of a reaction indicating the AAV5 vector to be unsuitable for use in the subject. The AAV5 Rep proteins are provided herein, and their antigenic fragments are routinely determined. The AAV5 capsid protein can be used to select an antigenic or immunogenic fragment, for example from the amino acid sequence set forth in SEQ ID NO:4 (VP1), the amino acid sequence set forth in SEQ ID NO: 5 (VP2) or the amino acid sequence set forth in SEQ ID NO:6 (VP3). Alternatively, or additionally, an antigenic or immunogenic fragment of an isolated AAV5 Rep protein can be utilized in this determination method. The AAV5 Rep protein from which an antigenic fragment is selected can have the amino acid sequence encoded by the nucleic acid set forth in SEQ ID NO:1, the amino acid sequence set forth in SEQ ID NO:2, or the amino acid sequence set forth in SEQ ID NO:3, the amino acid sequence set forth in SEQ ID NO: 12, or the amino acid sequence set forth in SEQ ID NO:14.

The AAV5 polypeptide fragments can be analyzed to determine their anti genicity, immunogenicity and/or specificity. Briefly, various concentrations of a putative immunogenically specific fragment are prepared and administered to a subject and the immunological response (e.g., the production of antibodies or cell mediated immunity) of an animal to each concentration is determined. The amounts of antigen administered depend on the subject, e.g. a human, rabbit or a guinea pig, the condition of the subject, the size of the subject, etc. Thereafter an animal so inoculated with the antigen can be exposed to the AAV5 viral particle or AAV5 protein to test the immunoreactivity or the antigenicity of the specific immunogenic fragment. The specificity of a putative antigenic or immunogenic fragment can be ascertained by testing sera, other fluids or lymphocytes from the inoculated animal for cross reactivity with other closely related viruses, such as AAV1, AAV2, AAV3, AAV4 and AAV5.

The hemagglutination assay can also be used to rapidly identify and detect AAV5 viral particles. Detection of hemagglutination activity correlates with infectivity and can be used to titer the virus. This assay could also be used to identify antibodies in a patients serum which might interact with the virus. Hemagglutination has been shown to correlate with infectivity and therefore hemagglutination may be a useful assay for identify cellular receptors for AAV5.

By the "suitability of an AAV5 vector for administration to a subject" is meant a determination of whether the AAV5 vector will elicit a neutralizing immune response upon administration to a particular subject. A vector that does not elicit a significant immune response is a potentially suitable vector, whereas a vector that elicits a significant, neutralizing immune response (e.g. at least 90%) is thus likely to be unsuitable for use in that subject. Significance of any detectable immune response is a standard parameter understood by the skilled artisan in the field. For example, one can incubate the subject's serum with the virus, then determine whether that virus retains its ability to transduce cells in culture. If such virus cannot transduce cells in culture, the vector likely has elicited a significant immune response.

Alternatively, or additionally, one skilled in the art could determine whether or not AAV5 administration would be suitable for a particular cell type of a subject. For example, the artisan could culture muscle cells in vitro and transduce the cells with AAV5 in the presence or absence of the subject's serum. If there is a reduction in transduction efficiency, this could indicate the presence of a neutralizing antibody or other factors that may inhibit transduction. Normally, greater than 90% inhibition would have to be observed in order to rule out the use of AAV-5 as a vector. However, this limitation could be overcome by treating the subject with an immunosuppressant that could block the factors inhibiting transduction.

As will be recognized by those skilled in the art, numerous types of immunoassays are available for use in the present invention to detect binding between an antibody and an AAV5 polypeptide of this invention. For instance, direct and indirect binding assays, competitive assays, sandwich assays, and the like, as are generally described in, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, N.Y. (1988). For example, enzyme immunoassays such as immunofluorescence assays (IFA), enzyme linked immunosorbent assays (ELISA) and immunoblotting can be readily adapted to accomplish the detection of the antibody. An ELISA method effective for the detection of the antibody bound to the antigen can, for example, be as follows: (1) bind the antigen to a substrate; (2) contact the bound antigen with a fluid or tissue sample containing the antibody; (3) contact the above with a secondary antibody specific for the antigen and bound to a detectable moiety (e.g., horseradish peroxidase enzyme or alkaline phosphatase enzyme); (4) contact the above with the substrate for the enzyme; (5) contact the above with a color reagent; (6) observe color change.

The antibody-containing sample of this method can comprise any biological sample which would contain the antibody or a cell containing the antibody, such as blood, plasma, serum, bone marrow, saliva and urine.

The present invention also provides a method of producing the AAV5 virus by transducing a cell with the nucleic acid encoding the virus.

The present method further provides a method of delivering an exogenous (heterologous) nucleic acid to a cell comprising administering to the cell an AAV5 particle containing a vector comprising the nucleic acid inserted between a pair of AAV inverted terminal repeats, thereby delivering the nucleic acid to the cell.

The AAV ITRs in the vector for the herein described delivery methods can be AAV5 ITRs (SEQ ID NOS: 19 and 20). Furthermore, the AAV ITRs in the vector for the herein described nucleic acid delivery methods can also comprise AAV1, AAV2, AAV3, AAV4, or AAV6 inverted terminal repeats.

The present invention also includes a method of delivering a heterologous nucleic acid to a subject comprising administering to a cell from the subject an AAV5 virion or particle comprising the nucleic acid inserted between a pair of AAV inverted terminal repeats, and returning the cell to the subject, thereby delivering the nucleic acid to the subject. The AAV ITRs can be any AAV ITRs, including AAV5 ITRs and AAV2 ITRs. For example, in an ex vivo administration, cells are isolated from a subject by standard means according to the cell type and placed in appropriate culture medium, again according to cell type (see, e.g., ATCC catalog). Viral particles are then contacted with the cells as described above, and the virus is allowed to transduce the cells. Cells can then be transplanted back into the subject's body, again by means standard for the cell type and tissue (e. g., in general, U.S. Pat. No. 5,399,346; for neural cells, Dunnett, S. B. and Björklund, A., eds., *Transplantation: Neural Transplantation-A Practical Approach*, Oxford University Press, Oxford (1992)). If desired, prior to transplantation, the cells can be studied for degree of transduction by the virus, by known detection means and as described herein. Cells for ex vivo transduction followed by transplantation into a subject can be selected from those listed above, or can be any other selected cell including progenitor cells of the cells listed above. Preferably, a selected cell type is examined for its capability to be transfected by AAV5. Preferably, the selected cell will be a cell readily transduced with AAV5 particles; however, depending upon the application, even cells with relatively low transduction efficiencies can be useful, particularly if the cell is from a tissue or organ in which even production of a small amount of the protein or antisense RNA encoded by the vector will be beneficial to the subject.

The present invention further provides a method of delivering a nucleic acid to a cell in a subject comprising administering to the subject an AAV5 virion or particle comprising the nucleic acid inserted between a pair of AAV inverted terminal repeats, thereby delivering the nucleic acid to a cell in the subject. Administration can be an ex vivo administration directly to a cell removed from a subject, such as any of the cells listed above, followed by replacement of the cell back into the subject, or administration can be in vivo administration to a cell in the subject. For ex vivo administration, cells are isolated from a subject by standard means according to the cell type and placed in appropriate culture medium, again according to cell type (see, e.g., ATCC catalog). Viral particles are then contacted with the cells as described above, and the virus is allowed to transfect the cells. Cells can then be transplanted back into the subject's body, again by means standard for the cell type and tissue (e. g., for neural cells, Dunnett, S. B. and Björklund, A., eds., *Transplantation: Neural Transplantation—A Practical Approach*, Oxford University Press, Oxford (1992)). If desired, prior to transplantation, the cells can be studied for degree of transfection by the virus, by known detection means and as described herein.

The present invention further provides a method of delivering a nucleic acid to a cell in a subject having neutralizing antibodies to AAV2 comprising administering to the subject an AAV5 virion or particle comprising the nucleic acid, thereby delivering the nucleic acid to a cell in the subject. A subject that has neutralizing antibodies to AAV2 can readily be determined by any of several known means, such as contacting AAV2 protein(s) with an antibody-containing sample, such as blood, from a subject and detecting an antigen-antibody reaction in the sample. Delivery of the AAV5 particle can be by either ex vivo or in vivo administration as herein described. Thus, a subject who might have an adverse immunogenic reaction to a vector administered in an AAV2 viral particle can have a desired nucleic acid delivered using an AAV5 particle. This delivery system can be particularly useful for subjects who have received therapy utilizing AAV2 particles in the past and have developed antibodies to AAV2. An AAV5 regimen can now be substituted to deliver the desired nucleic acid.

In any of the methods of delivering heterologous nucleic acids to a cell or subject described herein, the AAV5-conjugated nucleic acid or AAV5 particle-conjugated nucleic acids described herein can be used.

In vivo administration to a human subject or an animal model can be by any of many standard means for administering viruses, depending upon the target organ, tissue or cell. Virus particles can be administered orally, parenterally (e.g., intravenously), by intramuscular injection, by direct tissue or organ injection, by intraperitoneal injection, topically, transdermally, via aerosol delivery, via the mucosa or the like. Viral nucleic acids (non-encapsidated) can also be administered, e.g., as a complex with cationic liposomes, or encapsulated in anionic liposomes. The present compositions can include various amounts of the selected viral particle or non-encapsidated viral nucleic acid in combination with a pharmaceutically acceptable carrier and, in addition, if desired, may include other medicinal agents, pharmaceutical agents, carriers, adjuvants, diluents, etc. Parental administration, if used, is generally characterized by injection. Injectables can be prepared in conventional forms, either as liquid solutions or suspensions, solid forms suitable for solution or suspension in liquid prior to injection, or as emulsions. Dosages will depend upon the mode of administration, the disease or condition to be treated, and the individual subject's condition, but will be that dosage typical for and used in administration of other AAV vectors, such as AAV2 vectors. Often a single dose can be sufficient; however, the dose can be repeated if desirable.

Administration methods can be used to treat brain disorders such as Parkinson's disease, Alzheimer's disease, and demyelination disease. Other diseases that can be treated by these methods include metabolic disorders such as, muscoloskeletal diseases, cardiovascular disease, cancer, and autoimmune disorders.

Administration of this recombinant AAV5 virion or particle to the cell can be accomplished by any means, including simply contacting the particle, optionally contained in a desired liquid such as tissue culture medium, or a buffered saline solution, with the cells. The virion can be allowed to remain in contact with the cells for any desired length of time, and typically the virion is administered and allowed to remain indefinitely. For such in vitro methods; the virion can be administered to the cell by standard viral transduction methods, as known in the art and as exemplified herein. Titers of virus to administer can vary, particularly depending upon the cell type, but will be typical of that used for AAV transduction in general which is well known in the art. Additionally the titers used to transduce the particular cells in the present examples can be utilized.

The cells that can be transduced by the present recombinant AAV5 virion or particle can include any desired cell, such as the following cells and cells derived from the following tissues, human as well as other mammalian tissues, such as primate, horse, sheep, goat, pig, dog, rat, and mouse: Adipocytes, Adenocyte, Adrenal cortex, Airway epithelial cells, Alveolar cells, Amnion, Aorta, Ascites, Astrocyte, Bladder, Bone, Bone marrow, Brain, Breast, Bronchus, Cardiac muscle, Cecum, Cerebellar, Cervix, Chorion, Colon, Conjunctiva, Connective tissue, Cornea, Dermis, Duodenum, Endometrium, Endothelium, Endothelial cells, Ependymal cells, Epithelial tissue, Epithelial cells, Epidermis, Esophagus, Eye, Fascia, Fibroblasts, Foreskin, Gastric, Glial cells, Glioblast, Gonad, Hepatic cells, Histocyte, Ileum, Intestine, small Intestine, Jejunum, Keratinocytes, Kidney, Larynx, Leukocytes, Lipocyte, Liver, Lung, Lymph node, Lymphoblast, Lymphocytes, Macrophages, Mammary alveolar nodule, Mammary gland, Mastocyte, Maxilla, Melanocytes, Mesenchymal, Monocytes, Mouth, Myelin, Myoblasts Nervous tissue, Neuroblast, Neurons, Neuroglia, Osteoblasts, Osteogenic cells, Ovary, Palate, Pancreas, Papilloma, Peritoneum, Pituicytes, Pharynx, Placenta, Plasma cells, Pleura, Prostate, Rectum, Salivary gland, Skeletal muscle, Skin, Smooth muscle, Somatic, Spinal cord, Spleen, Squamous, Stomach, Submandibular gland, Submaxillary gland, Synoviocytes, Testis, Thymus, Thyroid, Trabeculae, Trachea, Turbinate, Umbilical cord, Ureter, and Uterus. Thus, the particles and virions of the present invention can be used to deliver a nucleic acid to these cells.

More specifically, the present invention provides a method of delivering a nucleic acid to an ependymal cell, comprising administering to the ependymal cell an AAV5 particle containing a vector comprising the nucleic acid inserted between a pair of AAV inverted terminal repeats, thereby delivering the nucleic acid to the ependymal cell.

Also provided by the present invention is a method of delivering a nucleic acid to a neuron, comprising administering to the neuron an AAV5 particle containing a vector comprising the nucleic acid inserted between a pair of AAV inverted terminal repeats, thereby delivering the nucleic acid to the neuron.

Further provided by this invention is a method of delivering a nucleic acid to an astrocyte, comprising administering to an astrocyte an AAV5 particle containing a vector comprising the nucleic acid inserted between a pair of AAV inverted terminal repeats, thereby delivering the nucleic acid to an astrocyte.

The present invention also provides a method of delivering a nucleic acid to an airway epithelial cell, comprising administering to an airway epithelial cell an AAV5 particle containing a vector comprising the nucleic acid inserted between a pair of AAV inverted terminal repeats, thereby delivering the nucleic acid to the airway epithelial cell.

The present invention also provides a method of delivering a nucleic acid to an alveolar cell, comprising administering to an alveolar cell an AAV5 particle containing a vector comprising the nucleic acid inserted between a pair of AAV inverted terminal repeats, thereby delivering the nucleic acid to the alveolar cell.

The present invention also provides a method of delivering a nucleic acid to a cerebellar cell, comprising administering to a cerebellar cell an AAV5 particle containing a vector comprising the nucleic acid inserted between a pair of AAV inverted terminal repeats, thereby delivering the nucleic acid to the cerebellar cell.

Also provided is a method of delivering a nucleic acid to an ependymal cell in a subject comprising administering to the subject an AAV5 particle comprising the nucleic acid inserted between a pair of AAV inverted terminal repeats, thereby delivering the nucleic acid to an ependymal cell in the subject.

Further provided is a method of delivering a nucleic acid to a neuron in a subject comprising administering to the subject an AAV5 particle comprising the nucleic acid inserted between a pair of AAV inverted terminal repeats, thereby delivering the nucleic acid to a neuron in the subject.

Also provided is a method of delivering a nucleic acid to an astrocyte in a subject comprising administering to the subject an AAV5 particle comprising the nucleic acid inserted between a pair of AAV inverted terminal repeats, thereby delivering the nucleic acid to an astrocyte in the subject.

Also provided is a method of delivering a nucleic acid to an alveolar cell in a subject comprising administering to the subject an AAV5 particle comprising the nucleic acid inserted between a pair of AAV inverted terminal repeats, thereby delivering the nucleic acid to an alveolar cell in the subject.

Also provided is a method of delivering a nucleic acid to a cerebellar cell in a subject comprising administering to the subject an AAV5 particle comprising the nucleic acid inserted between a pair of AAV inverted terminal repeats, thereby delivering the nucleic acid to a cerebellar cell in the subject.

Further provided is a method of delivering a nucleic acid to an airway epithelial cell in a subject comprising administering to the subject an AAV5 particle comprising the nucleic acid inserted between a pair of AAV inverted terminal repeats, thereby delivering the nucleic acid to an airway epithelial cell in the subject.

The use of AAV5 to deliver genes to the airway epithelia would be of benefit in genetic diseases like cystic fibrosis, pseudohypoaldosteronism, and immotile cilia syndrome. Furthermore, delivering genes to the airway epithelia would be of impact in several non-genetic diseases. For example, delivering genes that make antibiotic like peptides would be useful to prevent or treat bronchitis; delivering genes that make growth factors would be of value in common diseases like chronic bronchitis. Also, AAV5 could be used to deliver genes that may play a role in asthma, like IL-10, or antibodies to IgE and interleukins. The use of AAV5 to deliver genes to the alveolar epithelia would be of benefit in genetic diseases like alpha-1-antitrypsin. Furthermore, delivering genes to the alveolar epithelia would be of significance in several pulmonary non-genetic diseases. For example, delivering surfactant protein to premature babies or patients with ARDS; delivering genes that make antibiotic like peptides would be useful to prevent or treat pneumonia (perhaps of antibiotic-resistant organisms); delivering genes that make growth factors would be of value in emphysema; delivering genes that over-express the epithelial sodium channel or the Na-K ATPase could be used to treat cardiogenic and non-cardiogenic pulmonary edema; delivering genes that have an anti-fibrosis effect like interferon for pulmonary fibrosis would also be useful. Also, AAV5 could be used to deliver genes that may have a systemic effect like anti-hypertension drugs, insulin, coagulation factors, antibiotics, growth factors, hormones and others.

The present invention provides recombinant vectors based on AAV5. Such vectors may be useful for transducing erythroid progenitor cells or cells lacking heparin sulfate proteoglycans which is very inefficient with AAY2 based vectors. These vectors may also be useful for transducing cells with a nucleic acid of interest in order to produce cell lines that could be used to screen for agents that interact with the gene product of the nucleic acid of interest. In addition to transduction of other cell types, transduction of erythroid cells would be useful for the treatment of cancer and genetic diseases which can be corrected by bone marrow transplants using matched donors. Some examples of this type of treatment include, but are not limited to, the introduction of a therapeutic gene such as genes encoding interferons, interleukins, tumor necrosis factors, adenosine deaminase, cellular growth factors such as lymphokines, blood coagulation factors such as factor VIII and IX, cholesterol metabolism uptake and transport protein such as EpoE and LDL receptor, and antisense sequences to inhibit viral replication of, for example, hepatitis or HIV.

The present invention provides a vector comprising the AAV5 virus as well as AAV5 viral particles. While AAV5 is similar to AAV2, the two viruses are found herein to be physically and genetically distinct. These differences endow AAV5 with some unique advantages which better suit it as a vector for gene therapy.

Furthermore, as shown herein, AAV5 capsid protein is distinct from AAV2 capsid protein and exhibits different tissue tropism. AAV2 and AAV5 likely utilize distinct cellular receptors. AAV2 and AAV5 are serologically distinct and thus, in a gene therapy application, AAV5 would allow for transduction of a patient who already possess neutralizing antibodies to AAV2 either as a result of natural immunological defense or from prior exposure to AAV2 vectors.

The present invention is more particularly described in the following examples which are intended as illustrative only since numerous modifications and variations therein will be apparent to those skilled in the art.

EXAMPLE I

To understand the nature of AAV5 virus and to determine its usefulness as a vector for gene transfer, it was cloned and sequenced.

Cell Culture and Virus Propagation

Cos and HeLa cells were maintained as monolayer cultures in D10 medium (Dulbecco's modified Eagle's medium containing 10% fetal calf serum, 100 µg/ml penicillin, 100 units/ml streptomycin and IX Fungizone as recommended by the manufacturer, (GIBCO, Gaithersburg, Md., USA). All other cell types were grown under standard conditions which have been previously reported.

Virus was produced as previously described for AAV2 using the Beta galactosidase vector plasmid and a helper plasmid containing the AAV5 Rep and Cap genes (9). The helper plasmid was constructed in such a way to minimize any homologous sequence between the helper and vector plasmids. This step was taken to minimize the potential for wild-type (wt) particle formation by homologous recombination.

DNA Cloning and Sequencing and Analysis

In order to clone the genome of AAV5, infectious cell lysate was expanded in adherent cos cells and then suspension HeLa cells with the resulting viral particles isolated by CsCl isopynic gradient centrifugation. DNA dot blots of Aliquots of the gradient fractions indicated that the highest concentration of viral genomes were contained in fractions with a refractive index of approx. 1.372. While the initial description of the virus did not determine the density of the particles, this value is similar to that of AAV2. Analysis of annealed virion derived DNA obtained from these fractions indicated a major species of 4.6 kb in length which upon restriction analysis gave bands similar in size to those previously reported. Additional restriction mapping indicated a unique BssHII site at one end of the viral genome. This site was used to clone the major fragment of the viral genome. Additional overlapping clones were isolated and the sequence determined. Two distinct open reading frames (ORF) were identified. Computer analysis indicated that the left-hand ORF is approx 60% similar to that of the Rep gene of AAV2. Of the 4 other reported AAV serotypes, all have greater than 90% similarity in this ORF. The right ORF of the viral capsid proteins is also approximately 60% homologous to the Capsid ORF of AAV2. As with other AAV serotypes reported, the divergence between AAV5 and AAV2 is clustered in multiple blocks. By using the published three dimensional structure of the canine parvovirus and computer aided sequence comparisons, a number of these divergent regions have been shown to be on the exterior of the virus and thus suggest an altered tissue tropism.

Within the p5 promoter, a number of the core transcriptional elements are conserved such as the tataa box and YY1 site around the transcriptional start site. However the YY1 site at −60 and the upstream E-Box elements are not detectable suggesting an alternative method of regulation or activation.

The inverted terminal repeats (ITRs) of the virus were cloned as a fragment from the right end of the genome. The resulting fragment was found to contain a number of sequence changes compared to AAV2. However, these changes were found to be complementary and did not affect the ability of this region to fold into a hairpin structure. Within the stem region of the hairpin two sequence elements have been found to be critical for the function of the ITRs as origins of viral replication. A repeat motif of GAGC/T which serves as the recognition site of Rep and a GGTTGAG sequence downstream of the Rep binding site which is the position of Rep's site and strand specific cleavage reaction. This sequence is not conserved between AAV5 and the other cloned AAV's suggesting that the ITRs and Rep proteins of AAV5 cannot compliment the other known AAV's.

Figure 1:
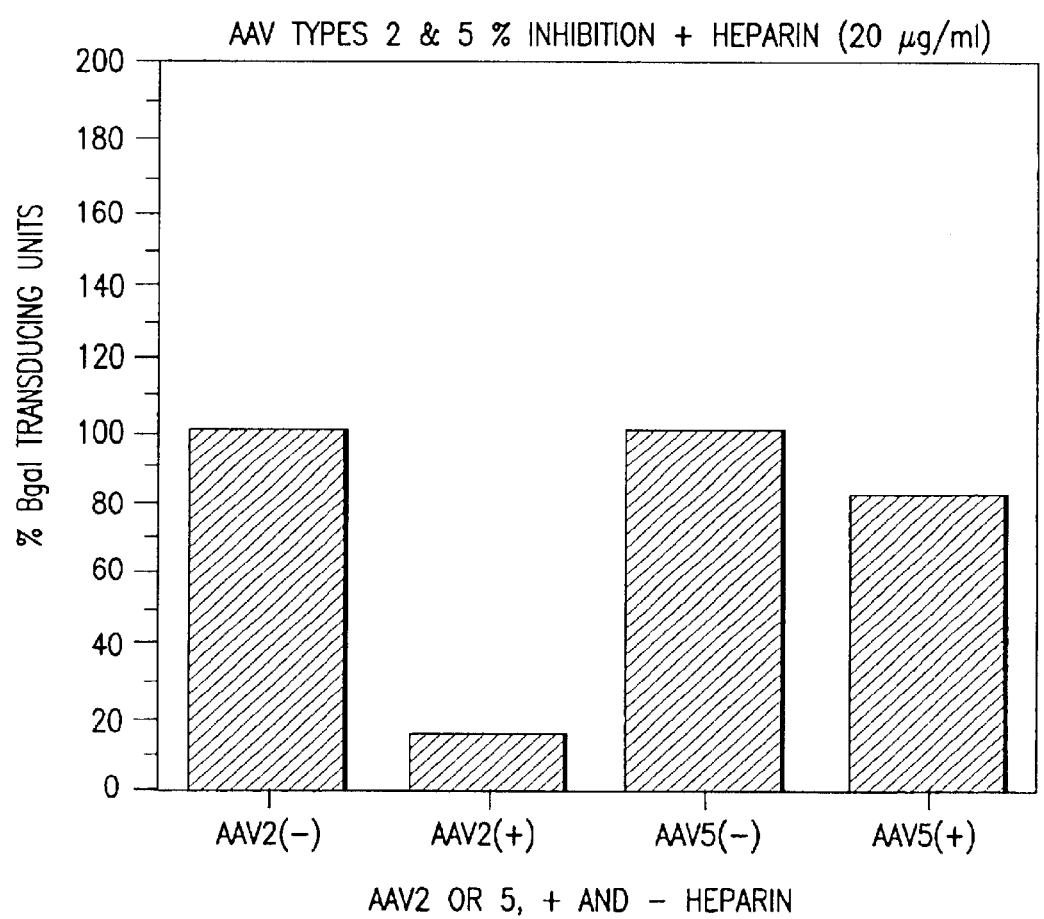
FIG. 1 shows Heparin inhibition results. Cos cells were plated in 12 well dishes at $5 \times 10^4$ cells per well. Serial dilutions of AAV2 or AAV5 produced and purified as previously described and supplemented with $5 \times 10^5$ particles of wt adenovirus were incubated for 1 hr at Rt in the presence of 20 µg/ml heparin (sigma). Following this incubation the virus was added to the cells in 400 µl of media for 1 hr after which the media was removed, the cells rinsed and fresh media added. After 24 hrs the plates were stained for Bgal activity.
Figure 2:
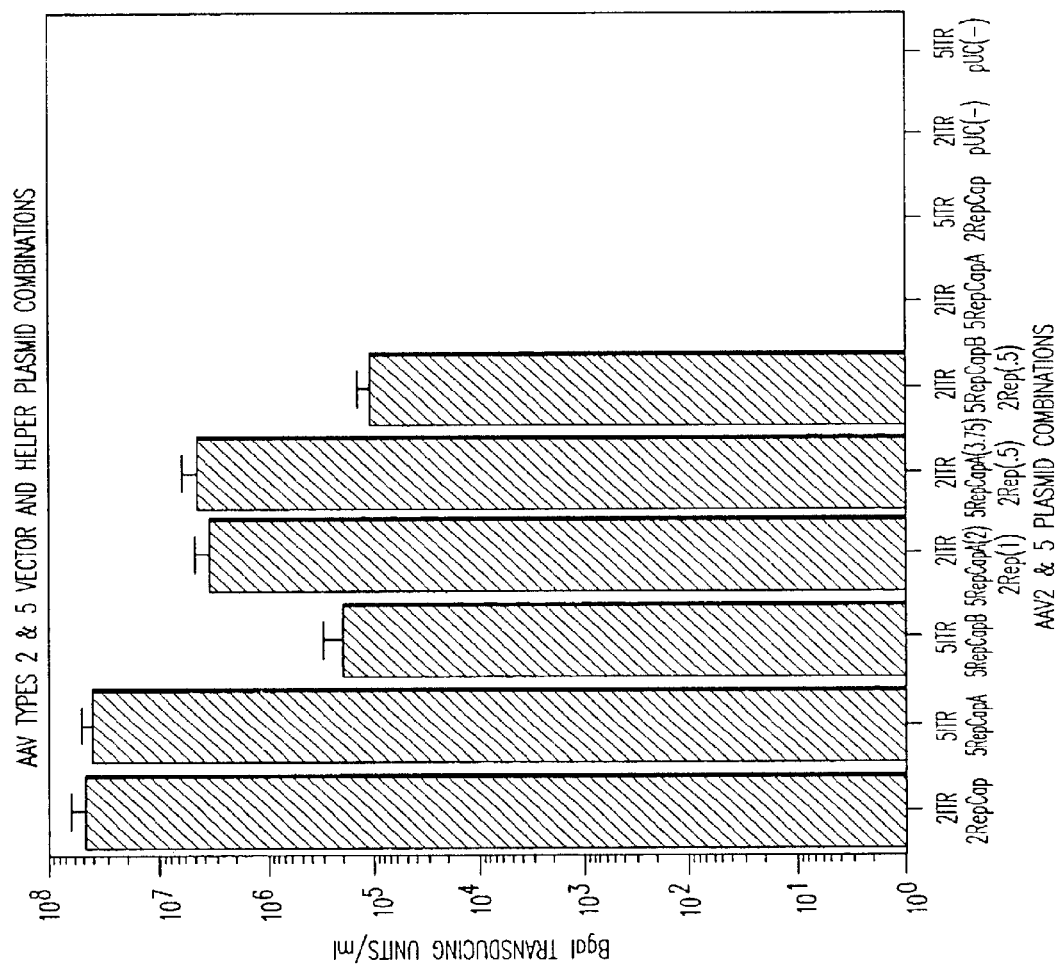
FIG. 2 shows AAV2 and AAV5 vector and helper complementation. Recombinant AAV particles were produced as previously described using a variety of vector and helper plasmids as indicated the bottom of the graph. The vector plasmids contained the Bgal gene with and RSV promoter and flanked by either AAV2 ITRs (2ITR) or AAV5 ITRs (5ITR). The helper plasmids tested contained either AAV2 Rep and cap genes (2repcap) AAV5 rep and cap genes with or without an SV40 promoter (SrepcapA and Srepcapb respectively) only the AAV2 rep gene (2rep) in varying amounts (1) or (0.5) or an empty vector (pUC). The resulting AAV particles were then titered on cos cells. AAV particles were only produced when the same serotype of ITR and Rep were present.
Figure 3:
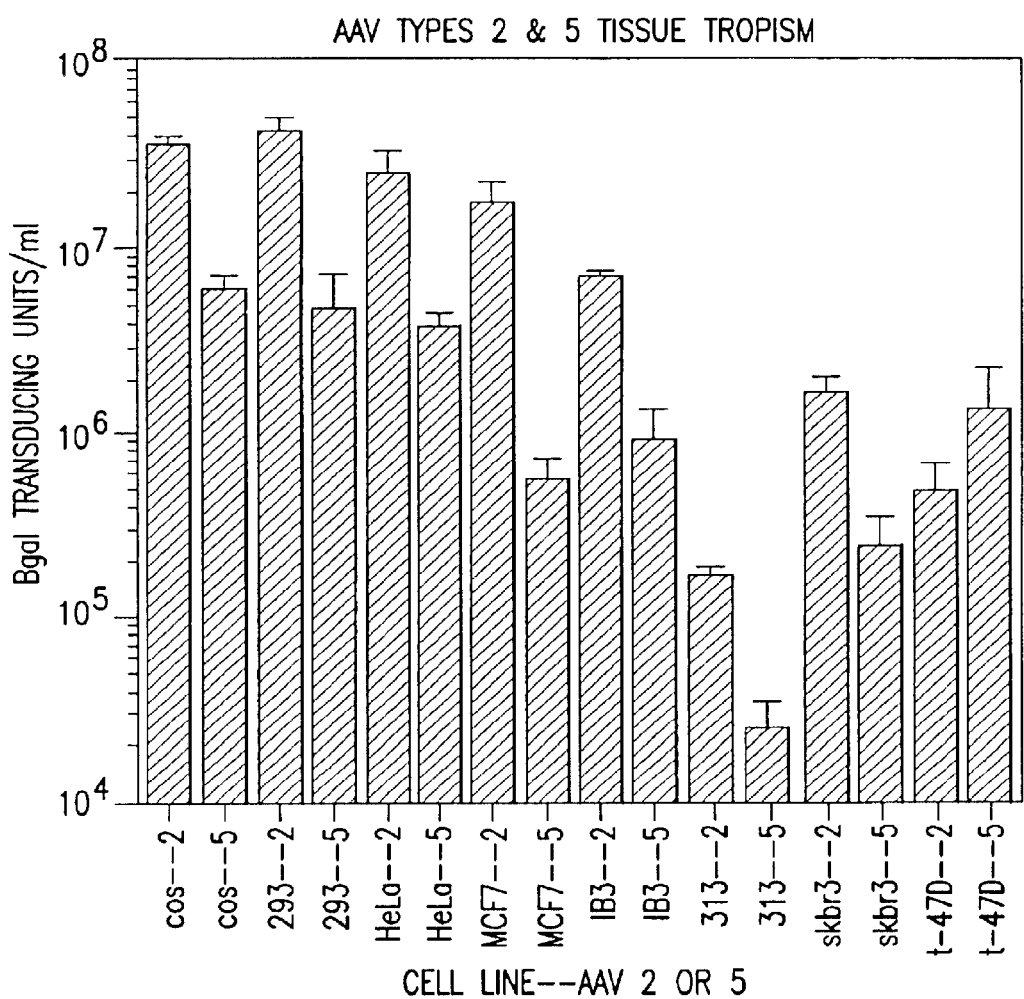
FIG. 3 shows AAV2 and AAV5 tissue tropism. Transduction of a variety of cell types indicated that AAV2 and AAV5 transduce cells with different efficiencies. Equal number of either AAV2 or AAV5 particles were used to transduce a variety of cell types and the number of bgal positive cells is reported.

To test the cross complementarity of AAV2 ITR containing genome and AAV5 ITR containing genomes recombinant particles were packaged either using type 2 Rep and Cap or type 5 Rep and Cap expression plasmids as previously described. As shown in FIG. 2, viral particles were produced only when the respective expression plasmids were used to package the cognate ITRs. This result is distinct from that of other serotypes of AAV which have shown cross complementary in packaging.

This specificity of AAV5 Rep for AAV5 ITRs was confirmed using a terminal resolution assay which can identify the site within one ITR cleaved by the Rep protein. Incubation of the Type 5 Rep protein with a type 2 ITR did not produce any cleavage products. In contrast, addition of type 2 Rep cleaved the DNA at the expected site. However AAV5 Rep did produce cleavage products when incubated with a type 5 ITR. The site mapped to a region 21 bases from the Rep binding motif that is similar to AAV2 TRS. The site in AAV2 is CGGT TGAG (SEQ ID NO: 22) but in type 5 ITR is CGGT GTGA (SEQ ID NO: 21). The ability of AAV5 Rep to cleave at a different but similarly positioned site may result in integration of AAV5 at a distinct chromosomal locus compared to AAV2.

Recombinant virus produced using AAV5 Rep and Cap was obtained at a greater titer than type 2. For example, in a comparative study, virus was isolated from $8 \times 10^7$ COS cells by CsCl banding and the distribution of the Beta galactosidase genomes across the gradient were determined by DNA dot blots of aliquots of gradient fractions. DNA dot blot titers indicated that AAV5 particles were produced at a 10–50 fold higher level than AAV2.

The sequence divergence in the capsid protein ORF implies that the tissue tropism of AAV2 and AAV5 would differ. To study the transduction efficiency of AAV5 and AAV2, a variety of cell lines were transduced with serial dilution's of the purified virus expressing the gene for nuclear localized Beta galactosidase activity. Approx. $2 \times 10^4$ cells were exposed to virus in 1 ml of serum containing media for a period of 48–60 hrs. After this time the cells were fixed and stained for Beta-galactosidase activity with 5-Bromo4-chloro-3-indolyl-b-D-galactopyranoside (Xgal) (ICN Biochemicals). Biological titers were determined by counting the number of positive cells in the different dilutions using a calibrated microscope ocular then multiplying by the area of the well. Titers were determined by the average number of cells in a minimum of 10 fields/well. Transduction of cos, HeLa, and 293, and IB3 cells with a similar number of particles showed approximately 10 fold decrease in titer with AAV5 compared with AAV2. In contrast MCF7 cells showed a 50–100 fold difference in transduction efficiency. Furthermore, both vectors transduced NIH 3T3 cells relatively poorly.

A recent publication reported that heparin proteoglycans on the surface of cells are involved in viral transduction. Addition of soluble heparin has been shown to inhibit transduction by blocking viral binding. Since the transduction data suggested a difference in tissue tropism for AAV5 and AAV2, the sensitivity of AAV5 transduction to heparin was determined. At an MOI of 100, the addition of 20 $\mu$g/ml of heparin had no effect on AAV5 transduction. In contrast this amount of heparin inhibited 90% of the AAV2 transduction. Even at an MOI of 1000, no inhibition of AAV5 transduction was detected. These data support the conclusions of the tissue tropism study, i.e. that AAV2 and AAV5 may utilize a distinct cell surface molecules and therefore the mechanism of uptake may differ as well.

AAV5 is a distinct virus within the dependovirus family based on sequence analysis, tissue tropism, and sensitivity to heparin. While elements of the P5 promoter are retained between AAV2–6 some elements are absent in AAV5 suggesting alternative mechanism of regulation. The ITR and Rep ORF are distinct from those previously identified and fail to complement the packaging of AAV2 based genomes. The ITR of AAV5 contains a different TRS compared to other serotypes of AAV which is responsible for the lack of complementation of the ITRs. This unique TRS should also result in a different integration locus for AAV5 compared to that of AAV2. Furthermore the production of recombinant AAV5 particles using standard packaging systems is approx. 10–50 fold better than AAV2. The majority of the differences in the capsid proteins lies in regions which have been proposed to be on the exterior of the surface of the parvovirus. These changes are most likely responsible for the lack of cross reactive antibodies and altered tissue tropism compared to AAV2.

From the Rep ORF of AAV2, 4 proteins are produced; The p5 promoter (SEQ ID NO: 18) produces rep 68 (a spliced site mutant) and rep78 and the p19 promoter (SEQ ID NO: 16) produces rep 40 (a spliced site mutant) and rep 52. While these regions are not well conserved within the Rep ORF of AAV5 some splice acceptor and donor sites exist in approximately the same region as the AAV2 sites. These sites can be identified using standard computer analysis programs such as signal in the PCGENE program. Therefore the sequences of the Rep proteins can be routinely identified as in other AAV serotypes.

Hemagglutination Assay

Hemagglutination activity was measured essentially as described previously (Chiorini et al 1997 J. Virol. Vol 71 6823–6833) Briefly 2 fold serial dilutions of virus in EDTA-buffered saline were mixed with an equal volume of 0.4% red blood cells in plastic U-bottom 96 well plates. The reaction was complete after a 2-h incubation at 8° C. Addition of purified AAV5 to a hemagglutination assay resulted in hemagglutination activity.

EXAMPLE II

Transduction of Airway Epithelial Cells

Figure 7:
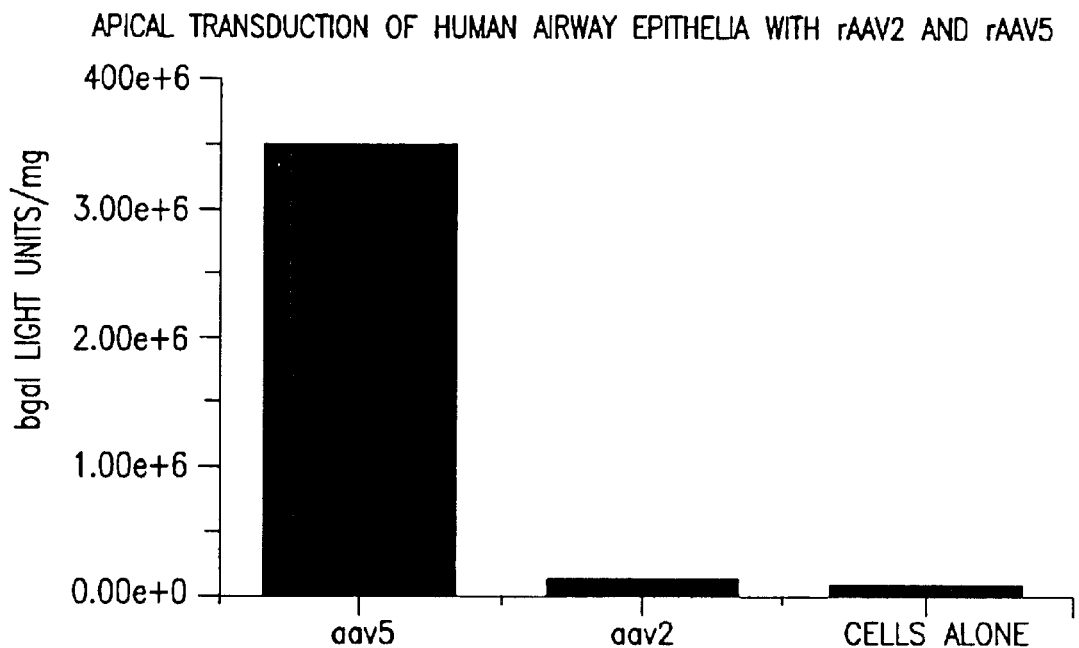
FIG. 7 shows the transduction of airway epithelial cells by AAV5. Primary airway epithelial cells were cultured and plated. Cells were transducted with an equivalent number of rAAV2 or rAAV5 particles containing a nuclear localized β-gal transgene with 50 particles of virus/cell (MOI 50) and continued in culture for 10 days. β-gal activity was determined and the relative transduction efficiency compared. AAV5 transduced these cells 50- fold more efficiently than AAV2. This is the first time apical cells or cells exposed to the air have been shown to be infected by a gene therapy agent.

Primary airway epithilial cells were cultured and plated as previously described (Fasbender et al. J. Clin Invest. 1998 Jul. 1; 102 (1): 184–93). Cells were transducted with an equivalent number of rAAV2 or rAAV5 particles containing a nuclear localized β-gal transgene with 50 particles of virus/cell (MOI 50) and continued in culture for 10 days. β-gal activity was determined following the procedure of (Chiorini et al. 1995 HGT Vol: 6 1531–1541) and the relative transduction efficiency compared. As shown In FIG. 7, AAV5 transduced these cells 50- fold more efficiently than AAV2. This is the first time apical cells or cells exposed to the air have been shown to be infected by a gene therapy agent.

Transduction of Striated Muscle

Figure 8:
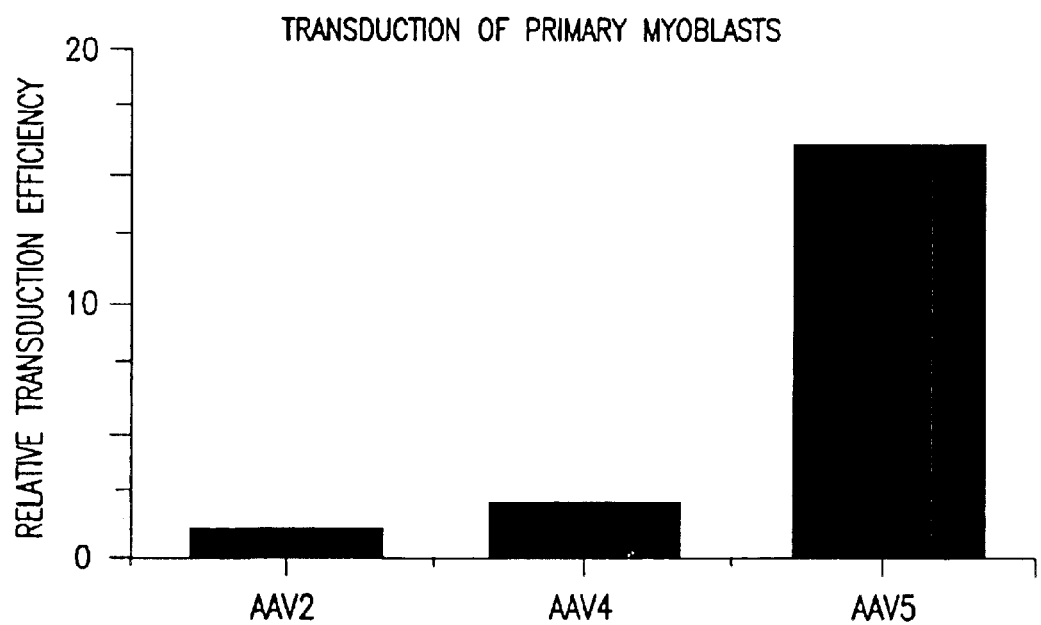
FIG. 8 shows transduction of striated muscle by AAV5. Chicken myoblasts were cultured and plated. Cells were allowed to fuse and then transduced with a similar number of particles of rAAV2 or rAAV5 containing a nuclear localized β-gal transgene after 5 days in culture. The cells were stained for β-gal activity and the relative transduction efficiency compared. AAV5 transduced these cells approximately 16 fold more efficiently than AAV2.

Chicken myoblasts were cultured and plated as previously described (Rhodes & Yamada 1995 NAR Vol 23 (12) 2305–13). Cells were allowed to fuse and then transduced with a similar number of particles of rAAV2 or rAAV5 containing a nuclear localized β-gal transgene as previously described above after 5 days in culture. The cells were stained for β-gal activity following the procedure of (Chiorini et al. 1995 HGT Vol: 6 1531–1541) and the relative transduction efficiency compared. As shown in FIG. 8, AAV5 transduced these cells approximately 16 fold more efficiently than AAV2.

Transduction of Rat Brain Explants

Figure 9:
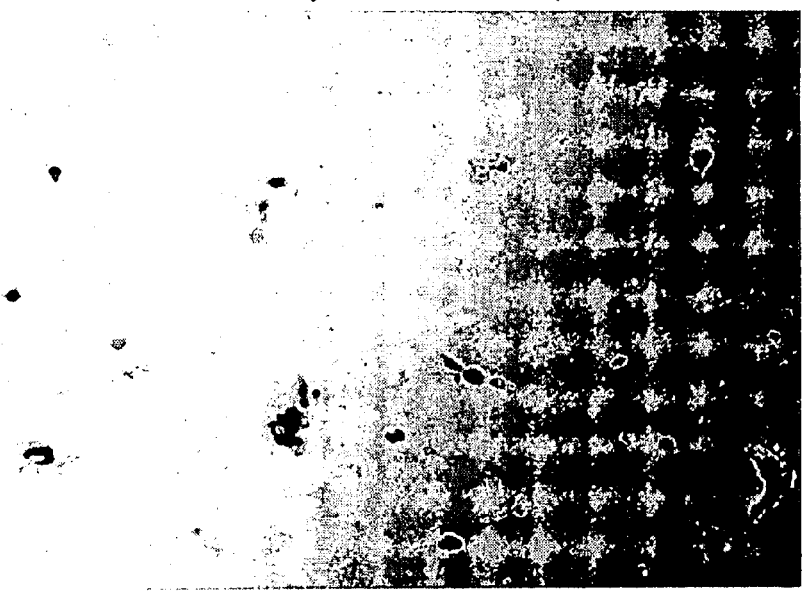
FIG. 9 shows transduction of rat brain explants by AAV5. Primary neonatal rat brain explants were prepared. After 7 days in culture, cells were transduced with a similar number of particles of rAAV5 containing a nuclear localized β-gal transgene. After 5 days in culture, the cells were stained for β-gal activity. Transduction was detected in a variety of cell types including astrocytes, neuronal cells and glial cells.

Primary neonatal rat brain explants were prepared as previously described (Scortegagna et al. Neurotoxicology. 1997; 18 (2): 331–9). After 7 days in culture, cells were transduced with a similar number of particles of rAAV5 containing a nuclear localized β-gal transgene as previously described. After 5 days in culture, the cells were stained for β-gal activity following the procedure of (Chiorini et al. 1995 HGT Vol: 6 1531–1541). As shown in FIG. 9, transduction was detected in a variety of cell types including astroytes, neuronal cells and glial cells.

Transduction of Human Umbilical Vein Endothelial Cells

Figure 10:
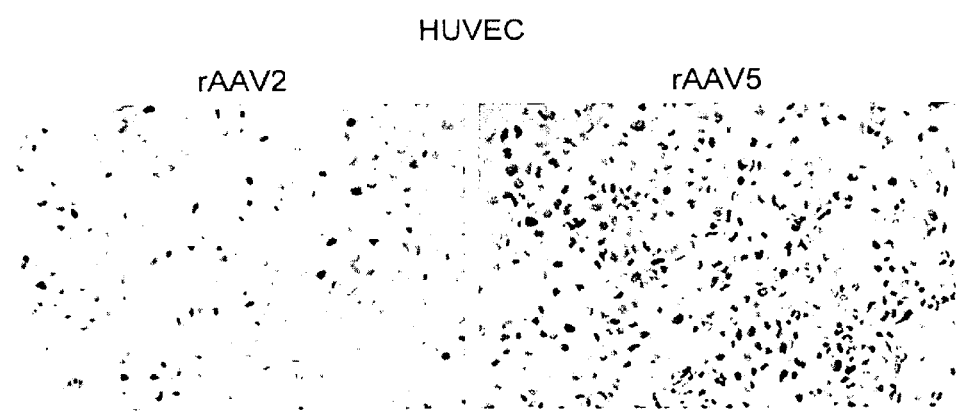
FIG. 10 shows transduction of human umbilical vein endothelial cells by AAV5. Human umbilical vein endothelial cells were cultured and plated. Cells were transduced with rAAV2 or rAAV5 containing a nuclear localized β-gal transgene with 10 particles of virus/cell (MOI 5) in minimal media then returned to complete media. After 24 hrs in culture, the cells were stained for β-gal activity and the relative transduction efficiency compared. As shown in AAV5 transduced these cell 5–10 fold more efficiently than AAV2.

Human umbilical vein endothelial cells were cultured and plated as previously described (Gnantenko et al. J Investig Med. 1997 Feb. 45(2): 87–98). Cells were transduced with rAAV2 or rAAV5 containing a nuclear localized β-gal transgene with 10 particles of virus/cell (MOI 5) in minimal media then returned to complete media After 24 hrs in culture the cells were stained for β-gal activity following the procedure of Chiorini et al. (1995 HGT Vol: 6 1531–1541), and the relative transduction efficiency compared. As shown in FIG. 10, AAV5 transduced these cell 5–10 fold more efficiently than AAV2.

Transduction of Human Umbilical Vein Endothelial Cells

Human umbilical vein endothelial cells were cultured and plated as previously described (Gnantenko et al. J Investig Med. 1997 Feb. 45(2): 87–98). Cells were transduced with rAAV2 or rAAV5 containing a nuclear localized β-gal transgene with 10 particles of virus/cell (MOI 5) in minimal media then returned to complete media. After 24 hrs in culture the cells were stained for β-gal activity following the procedure of Chiorini et al. (1995 HGT Vol: 6 1531–1541), and the relative transduction efficiency compared. As shown in FIG. 10, AAV5 transduced these cell 5–10 fold more efficiently than AAV2.

EXAMPLE III

Vector Production

Recombinant adeno-associated viral vectors based on AAV2, AAV4, or AAV5 were prepared using high efficiency electroporation and adenovirus infection as described previously (9). All three vectors contained a nucleus-targeted $E.$ $coli$ β-galactosidase gene with expression driven off the Rous sarcoma virus LTR promoter (RSV). The expression cassette was flanked by AAV2 ITR sequences for rAAV2βgal particles and rAAV4βgal particles. The expression cassette was flanked by AAV5 ITR's for rAAV5βgal particles. The number of recombinant particles were quantified by Southern dot blot, and the biological activity was tested by X-Gal histochemical staining in a serial dilution on Cos cells. The viral titers ranged between $2 \times 10^{11}$ to $3 \times 10^{12}$ particles/ml and the ratio of transducing to total particles was similar to that described previously for each of the types (9,10,45). The recombinant viruses used were screened for wild-type AAV contamination by PCR, and for wild-type adenovirus by a serial dilution assay using an FITC-hexon antibody (less than $10^3$ replication competent adenoviruses/ml) (46).

Injections

Six to 8 week old adult male C57BU6 mice were purchased from Jackson Labs (Bar Harbor, Me.) and housed at the University of Iowa Animal Care facility. All animal procedures were approved by the University of Iowa Animal Care and Use Committee. Virion injections were performed as previously described (24). Briefly, mice were anaesthetized and virions were stereotactically injected into either the right lateral ventricle or the right striatum, using a 26 gauge Hamilton syringe driven by a microinjector (Micro 1, World Precision Instruments, Sarasota, Fla.) at 0.5 µl per minute. For ventricular injections, 10 µl volumes were injected at coordinates 0.4 mm rostral and 1.0 mm lateral to bregma, and at a 2 mm depth. For striatal injections, 5 µl volumes were injected at coordinates 0.4 mm rostral and 2 mm lateral to bregma, and at a 3 mm depth. The doses of virion injected into the striatum, given as particle doses, were as follows: rAAV2βgal, $4 \times 10^9$ (n=5); rAAV4βgal, $2 \times 10^9$ (n=4) or $8 \times 10^9$ (n=3); rAAV5βgal, $1.5 \times 10^{10}$ (n=6) or $3 \times 10^{10}$ (n=2). For injections into the ventricle the doses were as follows: rAAV2βgal, $1 \times 10^9$ (n=3) or $2 \times 10^9$ (n=2); rAAV4βgal, $4 \times 10^9$ (n=8); rAAV5βgal, $3 \times 10^{10}$ (n=4). A minimum of two independent experiments was done for each virion and injection site.

Histochemistry

Three or 15 weeks after injection groups of mice were perfused with 2% paraformaldehyde, the brains were removed and processed as previously described (47). 10 µm thick coronal sections were cut at 100 gm intervals and X-Gal histochemical staining performed to identify β-galactosidase expressing cells (48). For each mouse, the number of β-galactosidase-positive cells in every fourth section, spanning 1.3 mm of tissue rostral and 1.3 mm caudal to the injection site, were counted and summed. These sums allow quantitative comparisons among the three vectors, although they do not reflect the total number of transduced cells in vivo.

Immunofluorescent Staining

Ten micrometer coronal cryosections of brains harvested 15 weeks after intrastriatal injection of rAAV5βgal were dual stained for β-galactosidase and either neuronal or astrocytic markers. The primary antibodies used were as follows: rabbit IgG specific for *E. Coli* β-galactosidase (BioDesign International, Saco Minn.); mouse monoclonal IgG specific for NeuN (Chemicon International, Inc., Temecula, Calif.), which strongly stains neuronal cell nuclei with lighter staining of the cytoplasm; and a Cy5 conjugated mouse monoclonal specific for glial fibrillary acidic protein (GFAP) (Sigma Immunocytochemicals, St. Louis, Mo.), an intermediate filament of astrocytes. Secondary antibodies used were ALEXA 488 goat anti-rabbit IgG (Molecular Probes, Eugene, Ore.) and lissamine-rhodamine goat anti-mouse IgG (Jackson ImmunoResearch Laboratories, West Grove, Pa.). Sections were blocked for 2 h at room temperature in phoshate-buffered saline (PBS) with 3% bovine serum albumin, 10% normal goat serum and 0.1% Triton X-100. Sections were incubated overnight with primary antibodies diluted in PBS with 3% bovine serum albumin and 0.1% Triton X-100 at 4° C., then washed and incubated with secondary antibodies in PBS with 1% normal goat serum and 0.1% Triton X-100 for 2 h at room temperture. Confocal laser microscopy was performed using 63× and 40× oil-immersion objectives on a Zeiss LSM 510 and associated software. Z-series images (0.3 to 1.0 μm wide slices) were captured and analyzed for cellular co-localization of antigens. Colocalization of β-galactosidase and either NeuN or GFAP is represented in 2-color merged images from single slices within the series.

Statistical Analysis

The data was analyzed using a three-way analysis of variance with the three factors consisting of rAAVβgal type, injection location, and time interval following virion injection. A log transformation was applied to the data to normalize the data distribution and reduce heterogeneity of group variances. Bonferroni's method was applied to each set of comparisons to adjust for the number of mice injected and to the p-values for each set of comparisons. A Bonferroni adjusted p-value <0.05 was considered statistically significant.

Quantification of Transduced Cells

Figure 11:
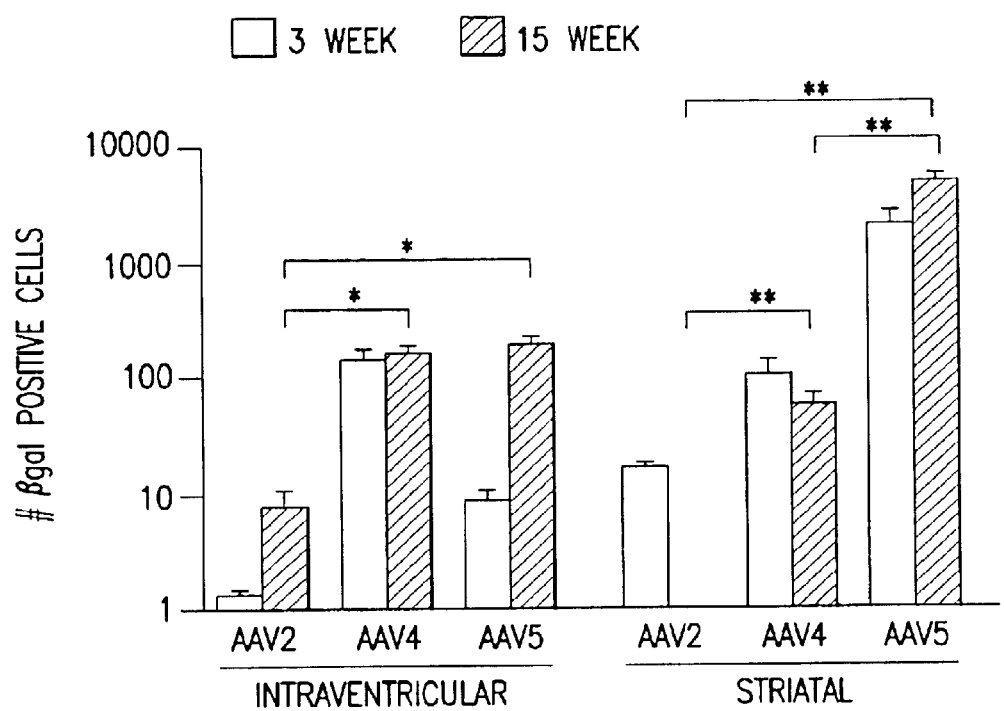
FIG. 11 shows the number of β-galactosidase positive cells after cerebral injection. Animals were injected with rAAV2βgal, rAAV4βgal, or rAAV5βgal into the ventricle or striatum of mice, and brains taken at the times indicated. Blocks (2.6 mm, surrounding the injection site) were sectioned, processed for β-galactosidase histochemistry, and transgene positive cells counted. Data represent mean ±SEM.*, p<0.05, **p<0.005

The efficiency of transduction of rAAV2, rAAV4 and rAAV5 in the brain using recombinant virion expressing the β-galactosidase reporter gene under control of the RSV promoter (rAAV2βgal, rAAV4βgal and rAAV5βgal, respectively) was evaluated. Groups of mice received either 10 μl of vector in the right lateral ventricle, or 5 μl of vector into the right striatum, at the particle doses stated above. Three or 15 weeks later the brains were harvested and transgene positive cells in cryosections spanning 2.6 mm rostral-caudal were quantified (FIG. 11).

Three weeks after intraventricular injection, the number of rAAV4βgal-transduced cells was approximately 100- and 10-fold greater than for rAAV2βgal and rAAV5βgal, respectively. rAAV2βgal yielded the poorest results, with the rare positive cell observed. After 15 weeks the number of rAAV5βgal-transduced cells was increased compared to the 3 week time point, reaching numbers similar to that of rAAV4βgal. This increase in rAAV5βgal expression nearly reached statistical significance (p=0.055). The number of transduced cells also tended to increase from 3 to 15 weeks for rAAV2βgal, but remained significantly lower than for the rAAV4- and rAAV5βgal vectors (p-0.007 and 0.019 respectively).

After striatal injections, strikingly greater numbers of transgene-expressing cells were detected after injection of rAAV5βgal compared to both rAAV2βgal and rAAV4βgal (for both, p<0.0001). In turn, rAAV4βgal transduced more cells than rAAV2βgal by 15 weeks (p=0.001). Comparison of the 3 and 15 week timepoints showed complete loss of rAAV2βgal-mediated transgene expression, but stable expression after rAAV4βgal injection. In contrast, there was a trend toward increased numbers of β-galactosidase-expressing cells from 3 to 15 weeks following rAAV5βgal injections.

Regional Distribution of Transduced Cells

Figure 12A:
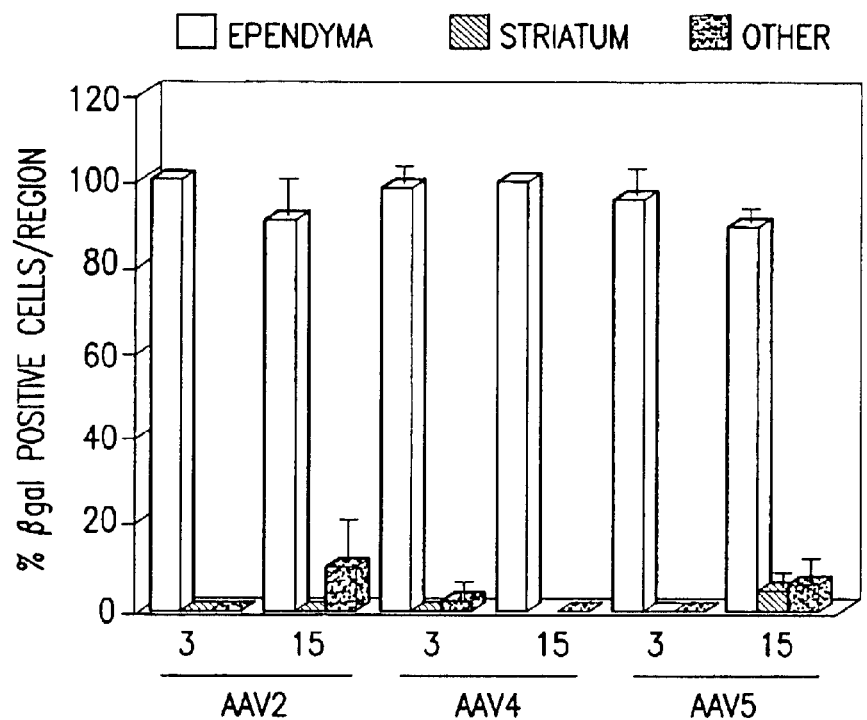
FIGS. 12A and 12B show. The distribution of β-galactosidase positive cells in brains of mice at 3 or 15 weeks following injection of rAAV2βgal, rAAV4βgal or rAAV5βgal. β-galactosidase positive cells within the ependymal, striatal, or 'other' (septal and fornix regions, corpus callosum, and neocortex) regions, from sections encompassing the injection site, were counted and that value represented as a percent of the total number of transgene positive cells. (A) Data from sections obtained 3 or 15 weeks after intraventricular injection. (B) Data from sections obtained 3 or 15 weeks after injection into the striatum. Data represent mean±SEM.
Figure 12B:
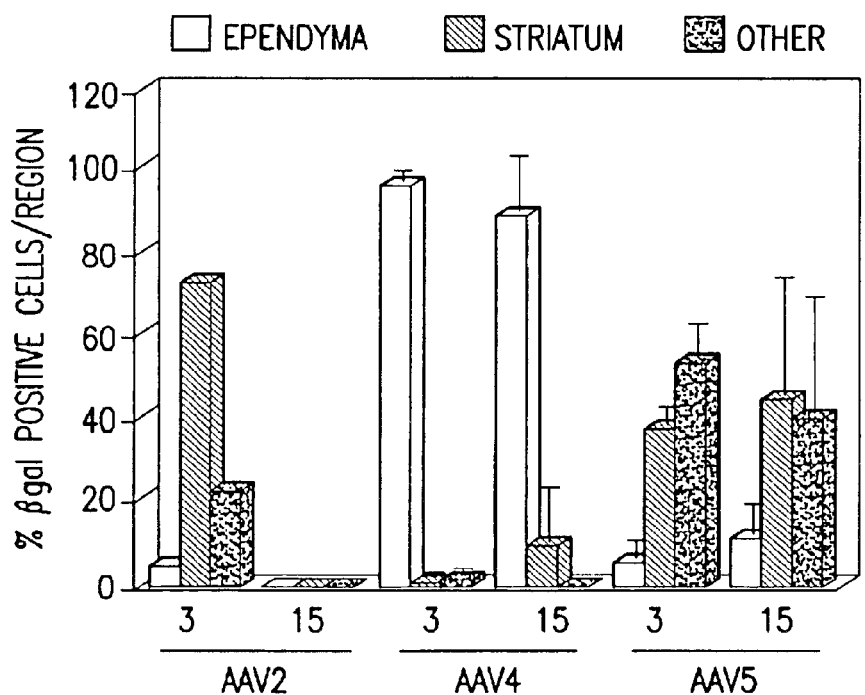
Figure 13C:
FIGS. 13A-F show the β-galactosidase histochemistry for transgene positive cells after striatal injection of rAAV vectors. (A,B) Representative photomicrograph of sections from mice injected with rAAV2βgal. Panel B is a magnified photograph of the transgene positive striatal region seen in A. (C) Demonstration of distinctive ependymal-specific staining for β-galactosidase in sections from animals injected with rAAV4βgal. (D-F). Photomicrographs illustrating the extensive distribution of transgene positive cells after rAAV5βgal injection. (E) Magnification of the striatal region in D. (F) Transgene positive cells in the cortex distant from the injection site. The photomicrographs are representative of at least three independent experiments. fi, fimbria region; lv, lateral ventricle; sp, medial septal region; st, striatum.
Figure 13B:
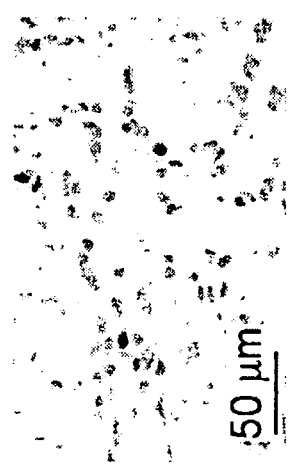
Figure 13A:
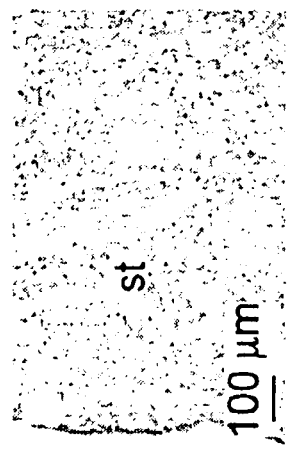
Figure 13F:
Figure 13E:
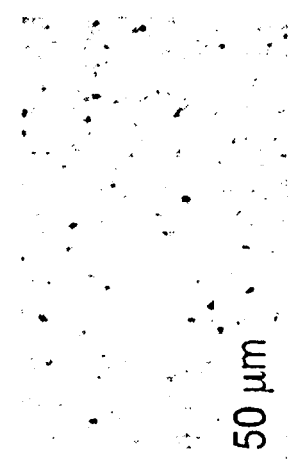
Figure 13D:

To analyze potential regional tropisms, β-galactosidase-positive cells were categorized into ependyma/choroid, striatum, or other (septal area, corpus callosum, neocortex, and fornix) regions. FIG. 12 illustrates the distribution of transduced cells for each virion after intraventricular or intrastriatal injections. Following intraventricular injections, transgene expressing cells were localized predominantly to the ependyma for all rAAVβgal types at both 3 and 15 weeks (FIG. 12A). Striatal injections yielded several interesting results (FIG. 12B). First, rAAV2- and rAAV5βgal virions mediated transduction in multiple regions. Second, this data again demonstrates the global loss in rAAV2βgal-transduced cells in all cerebral regions from 3 to 15 weeks.

The patterns of transduction observed after striatal injections of the three virions are illustrated in FIG. 13, which shows representative images of X-gal-stained sections. Few blue-stained nuclei were evident in the striatum of rAAV2βgal -injected mice (injected dose =$4\times10^9$ particles), and only at the 3 week time point (FIGS. 13A and B), while rAAV4βgal (injected dose =$4\times10^9$ particles) selectively transduced the ependyma (FIG. 13C). rAAV5βgal injections ($1.5\times10_{10}$ particles) resulted in diffuse transduction in multiple cerebral regions, including the striatum (FIG. 13D and E), septal region (FIG. 13D) and neocortex (FIG. 13F). Although the particle dose for rAAV5βgal was only 4 fold greater, the relative spread of cells transduced by rAAV5βgal was extensive; β-galactosidase-expressing cells were detected 4.0 mm in the rostral-caudal, 3.5 mm dorsal-ventral, and 3.2 mm laterally, to encompass much of the injected hemisphere and portions of the medial region.

Characterization of rAAV5βgal-transduced Cells

Figure 14A:
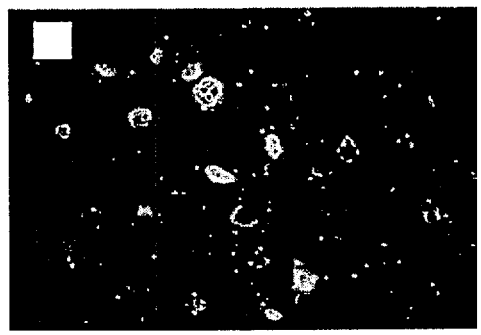
FIGS. 14A-D show the identification of transduced cells after intrastriatal injection of rAAV5βgal. Fifteen weeks after injection of rAAV5βgal coronal brain sections were dual stained for β-galactosidase (green nuclei) and NeuN (neuronal specific, red nuclei and light red cytoplasm), or for β-galactosidase and GFAP (astrocyte-specific, red cell processes). Confocal microscopy image analysis was performed and representative two-color merged images of single z-series slices are shown. In the striatum, both transduced neurons (yellow cell nuclei in A) and transduced astrocytes (B) were detected. In the medial septal region transduction appeared to be restricted to neurons (C), while in the corpus callosum the transduced cells were GFAP positive astrocytes (D). Images were captured using a 40× (A,B,D) or 63× (C) oil immersion objective.
Figure 14B:
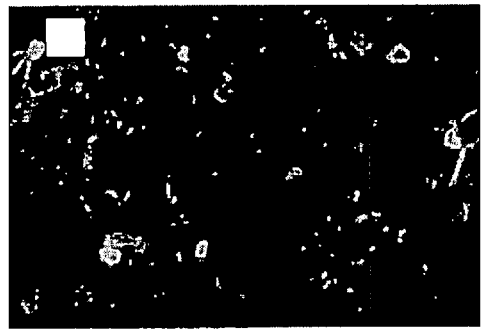
Figure 14C:
Figure 14D:
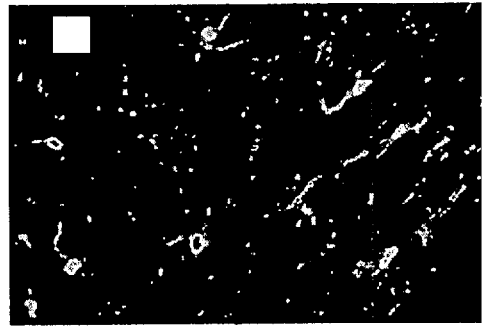

Previous studies have characterized the cell types transduced after parenchymal injection of rAAV2βgal under control of the CMV immediate early enhancer/promoter (CMVp) to be predominantly neurons, with an occasional transgene-expressing astrocyte (20,49,51). To determine which cell types were transduced by rAAV5βgal representative sections of brains harvested 15 weeks after intrastriatal injection were immunofluorescently stained. Confocal microscopy was performed to assess co-localization of β-galactosidase and representative markers. Sections were dual stained for β-galactosidase and either GFAP (astrocyte marker) or NeuN (neuron marker). In the striatum, many transgene-expressing cells stained positive for NeuN, indicating substantial neuronal cell transduction (FIG. 14A). Transduced astrocytes were also evident in the striatum, with GFAP-positive cell processes enveloping β-galactosidase-positive nuclei (FIG. 14B). Analyses of cells transduced in regions outside the striatum revealed that transgene-expressing cells in the cortex were also a mix of neurons and astrocytes, while those in the septal area were predominantly neurons (FIG. 14C). In addition, although rAAV5βgal-transduced cells were noticeably more concentrated in gray matter areas, a minor proportion of transgene-positive nuclei were evident in the corpus callosum, sometimes far-removed from the injection site. In these instances, GFAP immunoreactivity identified these cells as astrocytes (FIG. 14D).

In this study, CNS cell transduction with rAAV2, rAAV4 and rAAV5 virions carrying an RSV-β-galactosidase expression cassette after intracerebral injections into the lateral ventricle or the striatum was assessed. After intraventricular injections, all three virions transduced primarily ependymal cells. Results with rAAV2βgal were similar to prior reports showing that transduced cells were few, and restricted to the ependyma/choroid plexus (49,50). Ependymal cell transduction was more impressive with rAAV4- and rAAV5βgal vectors. Since the rAAV2βgal and rAAV4βgal particles contain identical DNA sequences, differences in transduction efficiencies between these two vectors must be attributed to variations in their capsids. This implies that the rAAV4 capsid mediates more efficient entry into ependymal cells than rAAV2. rAAV5 capsid is also distinct and may likewise target ependyma more efficiently than rAAV2. Differences in the ITR region of rAAV5βgal may additionally influence expression. Interestingly, for rAAV5βgal, the number of β-galactosidase-positive ependymal cells increased significantly after 3 weeks, reaching levels similar to rAAV4βgal at 15 weeks.

Following intrastriatal injections, distinct regional patterns of transduction for all three virions were observed. With rAAV4βgal, numerous positive cells lined the ventricles, with very few transgene-expressing cells in the parenchyma. In contrast, rAAV2βgal and rAAV5βgal vectors transduced predominantly parenchymal cells, and unlike rAAV2βgal (20,49,51), rAAV5βgal transduced a significant proportion of astrocytes as well as neurons. Moreover, rAAV5βgal transduced a greater number of cells, over a larger volume of tissue compared to rAAV2βgal.

When compared to AAV2, heterogeneities in the capsid-encoding regions, heparin-insensitive transduction, and differential abilities to transduce cell lines in vitro together strongly implicate different receptor requirements for cell entry by AAV5 (10,45,56). The enhanced parenchymal cell transduction observed for rAAV5βgal compared to rAAV2βgal, as well as the diffuse and widespread pattern of transduction mediated by rAAV5βgal may similarly reflect distinct receptor requirements. In the rat brain, rAAV2βgal particles have been shown to preferentially bind neurons, but not glial cells, within minutes of injection, and be transported within 30 minutes to neuronal cell nuclei (57). Considering that neuronal subtypes in adult rodent brain express integral membrane heparan sulfate proteoglycans such as syndecans (58,59) and glypican-1 (60), it is conceivable that AAV2 binds strongly to and enters neurons surrounding the injection site. Moreover AAV2 particles may become sequestered in extracellular HSPG in a way that limits vector diffusion and reduces transduction efficiency. An ability of rAAV5βgal to travel in a less restricted fashion may explain these observations of widespread transduction in comparison to rAAV2βgal.

Following intrastriatal injection loss of rAAV2βgal-transduced cells over time consistent with observations of others (20,49,50,51,62,63) was observed. In contrast, transgene expression after rAAV5βgal injection was stable over the time-course of our study. rAAV5 could target to cell subsets better able to sustain RSVp-driven transcription, or there could be positive influences of the AAV5 ITRS on either genome stability or RSV promoter activity.

These experiments explored the use of rAAV5 as a vector for gene transfer to the CNS. rAAV5βgal transduced large numbers of cells, with lasting expression in both neuronal and glial types. More importantly, rAAV5βgal exhibited an extensive transduction volume. Vector diffusion is an extremely valuable feature for gene therapy of CNS diseases exhibiting widespread pathology, such as the neurodegenerative aspect of the lysosomal storage diseases. This characteristic coupled to persistent expression could reduce the need for multiple injection sites and repeat injections, and their obvious associated risks.

EXAMPLE IV
Human Airway Epithelia

Airway epithelial cells were obtained from surgical polypectomies of non-CF patients or from trachea and bronchi of lungs removed for organ donation. Cells were isolated by enzyme digestion as previously described (67). Freshly isolated cells were seeded at a density of $5 \times 10^5$ cells/cm$^2$ onto collagen-coated, 0.6 cm$^2$ diameter Millicell polycarbonate filters (Millipore Corp., Bedford, Mass.). The cells were maintained at 37° C. in a humidified atmosphere of 7% $CO_2$ and air. Twenty-four hours after plating, the mucosal media was removed and the cells were allowed to grow at the air-liquid interface (68, 69). The culture medium consisted of a 1:1 mix of DMEM/Ham's F12, 5% Ultroser G (Biosepra SA, Cedex, France), 100 U/ml penicillin, 100 μg/ml streptomycin, 1% nonessential amino acids, and 0.12 U/ml insulin. Airway epithelia were allowed to reach confluence and develop a transepithelial electrical resistance (Rt), indicating the development of tight junctions and an intact barrier. Epithelia were allowed to differentiate by culturing for at least 14 days after seeding and the presence of a ciliated surface was tested by scanning electron microscopy (70).

Recombinant Adeno-associated Viruses

Recombinant AAV vectors expressing L3-galactosidase, AAV2/βGal, AAV4/62 Gal, AAV5/βGal, were prepared using high efficiency electroporation and packaging initiated by adenovirus infection and characterized as described previously (45). Briefly, rAAV particles were produced by electroporating $8 \times 10^8$ exponentially growing Cos cells with 400 ug of a 1:1 mixture of pAAV2RnLacZ and pSV40oriAAV2 for production of AAV2, pAAV2RnLacZ and pSV40oriAAV4 for AAV4, or pAAV5RnLacZ and pSV40oriAAV5 for AAV5 in 1× RPMI (2.5 ml of 2× RPMI, 1 ml FCS, 1.5 ml $HO_2$, and 50 ul of 1M Hepes pH 7.4) and incubated on ice for 10 min prior to electroporation. Electroporation was performed in a 4 mm gap cuvette (BioRad Richmond Calif.) containing 0.5 mls of the cell DNA mixture using a BTX 600 electroporator. Conditions used for electroporation were 300 Volt, 2100 μF, 48 ohms. Following electroporation the cells were incubated on ice for 10 min then plated into ten 15 cm dishes. The following day the medium was replaced and the cells allowed to recover. Approximately 30–50% of the cells which were initially electroporated reattached to the plates and 90% of these cells show strong expression of the β-gal reporter gene. Two days later, the plates were infected with approximately $5 \times 10^9$ PFU (MOI of 10) of wild-type adenovirus type 5 for 1 h. in serum free media and then supplemented with D10 media. Seventy-two hours post infection the cells were harvested by scraping and the virus and the cells pelleted by low speed centrifugation. The pellet is resuspended in 7.5 ml of TD buffer for every 10 plates (TD=140 mM NaCl, 5 mM KCl, 0.7 mM $K_2HPO_4$, 25 mM Tris/HCl, pH 7.4). Trypsin (0.5 volumes of 0.25%) and sodium deoxycholate (0.5 volumes of 10%) are added to the suspension, gently mixed and incubated at 37° C. for 30 min. The lysate is then homogenized thoroughly (approximately 20 strokes in a Wheaton B homogenizer). CsCl is next added to a final density of 1.4 g/cm$^3$ and the homogenate is distributed into two polyallomer tubes and centrifuged in a SW40.1 swinging bucket rotor at 38,000 RPM for 65 hr at 20° C. The pellicle at the top of the gradient is removed using a pasture pipette and the gradients fractionated by side puncture. Fractions with a refractive index of 1.373–1.371 were pooled for AAV2 and AAV5 and 1.378–1.376 for AAV4, and centrifuged again using an SW50.1 rotor, and fractionated as described above. Refractive indices were determined using a Zeiss refractometer.

Recombinant viruses were titered by Southern blot, and X-Gal staining in a serial dilution on COS-7 cells tested their biological activity. The viral titers ranged between $4 \times 10^{12}$ and $8 \times 10^{12}$ particles/ml. The particle to transduction unit ratio on these cells was similar to that previously reported for all 3 viruses on Cos cells (about $10^4$ to 1). The recombinant viruses used were screened for wild-type AAV contamination by PCR, and for wild-type adenovirus by a serial dilution assay using a FITC-hexon antibody (less than $10^3$ replication competent adenoviruses/ml) (70).

Viral Infection and Binding Assays

Five hundred virions of the recombinant AAV/per cell (in phosphate-buffered saline) were added to the apical surface. Following the indicated incubation time, the viral suspension was removed and the epithelia were rinsed twice with PBS. After infection, the epithelia were incubated at 37° C. for an additional fourteen days.

To assess binding to airway epithelia, the epithelia were incubated for 30 min at 4° C. with 500 virions/cell of AAV2/βGal, AAV4/βGal or AAV5/βGal. The epithelia were then rinsed, and cell-associated AAV viral DNA was measured from cell lysates of seven epithelia per dot. Samples were subjected to 3 freeze/thaw cycles and then blotted onto a nylon membrane (Ambion, Austin, Tex.). Detection of the AAV viral DNA was done by hybridizing with a $^{32}$P-labeled pCMVβgal. Unhybridized probe was washed as follows: two washes with 2% SSC and 0.1× SDS at room temperature for 15 min, one wash with 0.5×SSC and 0.1% SDS at 55° C. for 1 hr, and finally one wash with 0.5× SSC and 0.1% SDS at 65° C. for 30 min. Dot blots were developed and quantitated using a Phosphorimager (Molecular Dynamics, Sunnyvale, Calif.) (71).

Measurement of β-galactosidase Activity

Total β-galactosidase activity was measure using a commercially available method (Galacto-Light, Tropix, Inc., Bedford, Mass.). Briefly, after rinsing with PBS, cells were removed from filters by incubation with 120 μl lysis buffer (25 mM Tris-phosphate, pH 7.8; 2 mM DTT; 2 mM 1,2-diaminocyclohexane-N,N,N',N'-tetraacetic acid; 10% glycerol; and 1% Triton X-100) for 15 min. Light emission was quantified in a luminometer (Analytical Luminescence Laboratory, San Diego Calif.). To histochemically detect β-galactosidase activity, the chromogenic reagent XGal (5-bromo-4chloro-3-indonyl-β-D-galactopyranoside, Boehringer Mannheim) was used. Human airway epithelia and murine lungs were fixed with 1.8% formaldehyde and 2% glutaraldehyde, and then incubated for 16 hr at 37° C. with 313 μl of 40 mg/ml X-Gal in DMSO dissolved in 12.5 ml of PBS (pH 7.8).

Studies in Mice

For in vivo analysis, 6–8 week old C57BL/6 mice (The Jackson Laboratory, Bar Harbor, Mass.) were studied. Mice were lightly anesthetized using a methoxyflurane chamber. Recombinant AAV2 and AAV5 ($1 \times 10^{10}$ particles) were administered intranasally in two 62.5 μl instillations delivered 5 min apart. The experiment was performed with five animals per group. Twenty-eight days after vector administration, animals were sacrificed with $CO_2$. PBS (10 ml) was instilled into the right ventricle and then the lungs and heart were removed intact. The trachea was intubated and instilled at 10 cm of pressure with the following solutions in order: PBS, 4% paraformaldehyde, PBS, and stained overnight with X-Gal stain and finally rinsed with PBS. Lungs were cryosectioned and sections were analyzed by two independent reviewers that were unaware of the experimental identity of the samples. The reviewers counted the number of blue nuclei of βgal-expressing cells from a 5 μm slice obtained every 50 μm (n=20 fields/lung). The total number of airway epithelial cells was estimated by dividing the surface of the epithelia (π2r) by (4.9 μm), an estimate of the diameter of the airway epithelial cells (2425.3±20 airway cells/field).

Figure 15A:
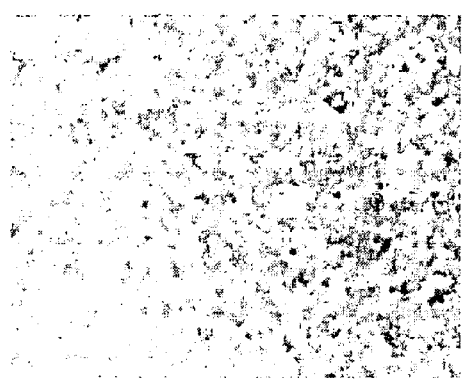
FIGS. 15A-D show gene transfer to the apical surface of well-differentiated human airway epithelia by different recombinant AAV serotypes. (A,D) Enface images of human airway epithelia (A) and epithelia transduced with 500 particles per cell of AAV2/βGal (1), AAV4/βGal (C) and AAV5/βGal (D). The blue staining show cells that have been transduced with vector.
Figure 15B:
Figure 15C:
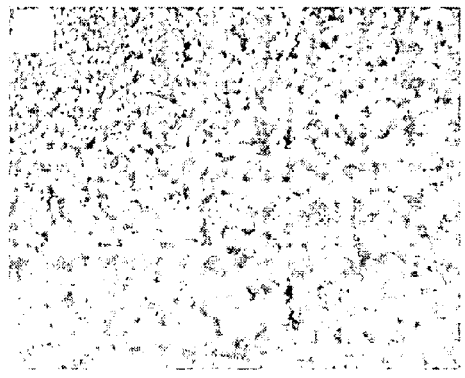
Figure 15D:
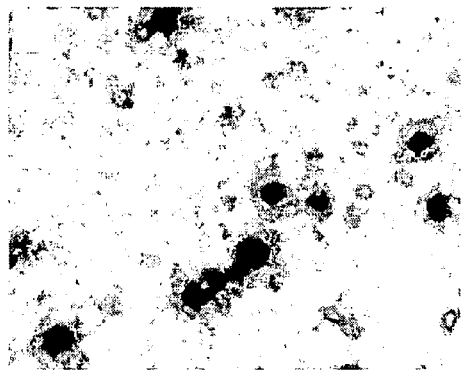

AAV5 can mediate gene transfer through the apical surface of human airway epithelia. Because AAV2, AAV4, and AAV5 have different tropism in cell lines, the efficiency of these different serotypes on primary cultures of differentiated human airway epithelia was compared. Epithelia were transduced for 12 hours at a relatively low particle per cell ratio (500 particles/cell) with an estimated MOI of less than 1. To allow for maximal expression, the epithelia were studied 2 weeks after infection. Quantification of the β-galactosidase activity showed that AAV5-tranduced cells generated approximately 50 fold greater activity than AAV2 or AAV4 transduced cells (FIG. 15E). To histochemically detect the β-galactosidase activity, we stained the epithelia with a chromogenic reagent X-gal. Similar to the quantitative analysis, FIGS. 15B & 15C shows only minimal gene transfer in epithelia transduced by AAV2/βGal or AAV4/βGal compared to epithelia transduced with AAV5/βGal (FIG. 15D). To rule out the possibility of pseudotransduction by protein transfer, the epithelia was assayed 1 hour after the application of the AAV vectors, no β-gal activity was detected over background.

AA V5 Binds to the Apical Surface of Well-differentiated Human Airway Epithelia

Figure 16A:
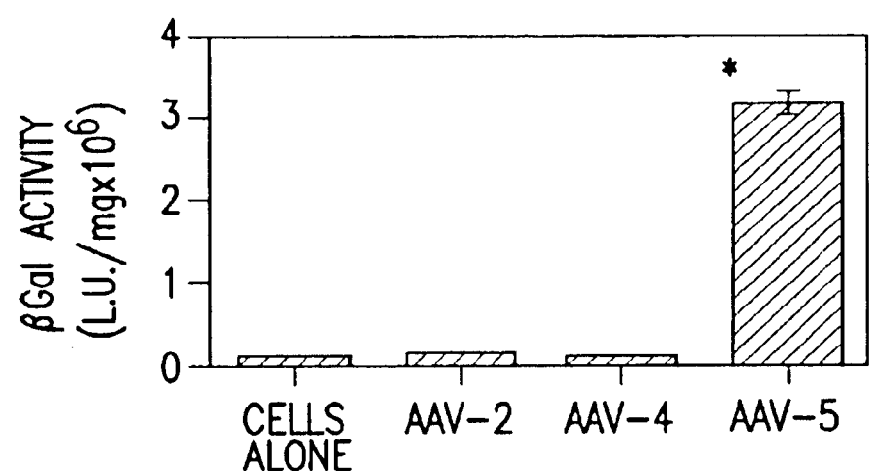
FIGS. 16A and 16B show the binding of AAV2/βGal, AAV4/βGal, and AAV5/βGal to organotypic cultures of ciliated human airway epithelia. A. Figure shows the dot blot of virus bound to the epithelia of 3 experiments with seven epithelia per experiment (input virus 500 particles/cell). For the purpose of quantitation, a dilution series of rAAV plasmid was also blotted and probed to demonstrate the linearity of the detection system. B. Figure shows the results of the quantification of the dot blot data. The data are means±SEM of the percentage of total virus added that remained epithelia-associated after a 30 min incubation. Asterisk indicates p<0.05.
Figure 16B:
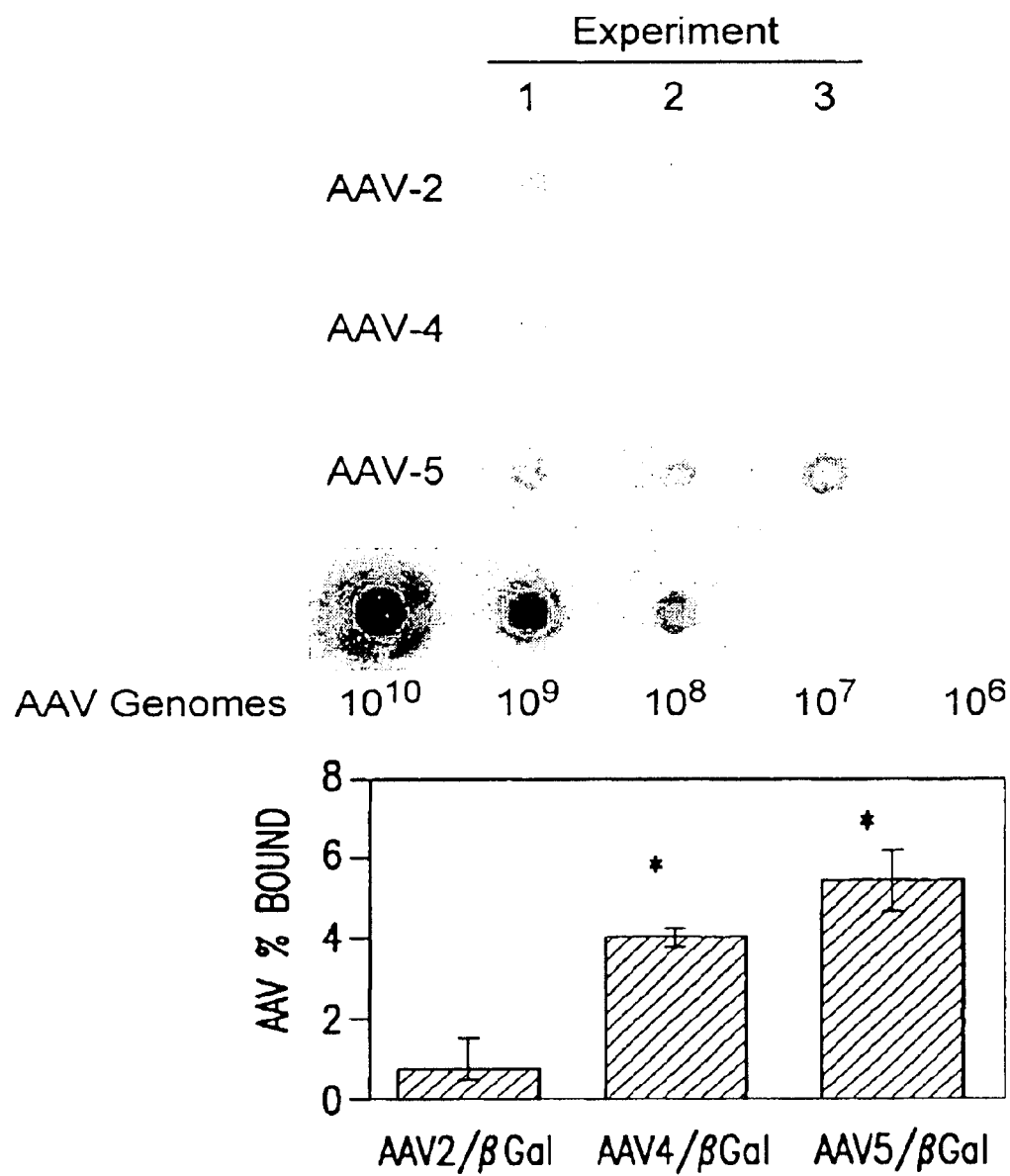

The hypothesis that the improved transduction efficiency of AAV5/βGal relied on increased binding to well-differentiated airway epithelia was tested. Epithelia were incubated for 30 min with 500 particles per cell of AAV2/βGal, AAV4/βGal or AAV5/βGal, then rinsed. Cell-associated AAV was estimated by dot blot analysis. FIG. 16 shows that differentiated airway epithelia bound AAV5 derived vector approximately seven-fold better than AAV2/βGal. Of interest, AAV4/Gal also bound to the apical surface five times more efficiently than AAV2/Gal. These data may explain some of the advantage of AAV5 over AAV2-derived vectors in mediating gene transfer to the airway epithelia.

Figure 17:
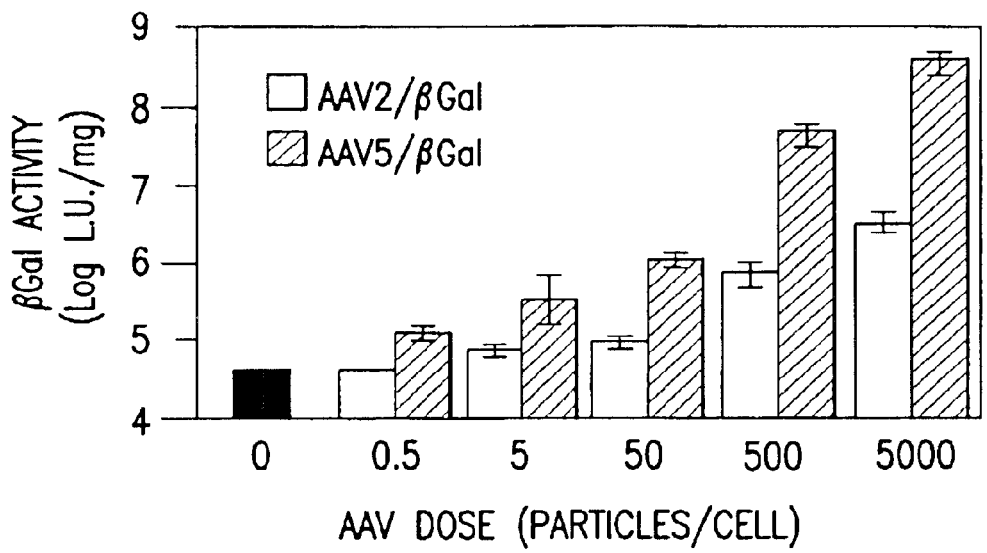
FIG. 17 shows the effect of dose on AAV2/βGal and AAV5/βGal-mediated gene transfer to human airway epithelia. Human airway epithelia were exposed to increasing number of particles per cell of AAV2/βGal and AAV5/βGal from the apical surface. The epithelia were then rinsed after 60 min and incubated for 2 weeks prior to analysis of β-galactosidase activity. Data are the β-gal activity per mg protein±SEM (n=4).

Effect of Dose and Incubation Time on AAV5 Infection of the Apical Surface of Human Airway Epithelia Since AAV5 appeared to bind and mediate gene transfer to the airway epithelia more efficiently than AAV2, the effect of dose of the virus was examined. FIG. 17 shows that in a range of 0.5 to 5000 particles/cell, AAV5 always outperformed AAV2/βGal. The course of AAV5-mediated expression of β-galactosidase in vitro over a month period was also tested. The level of &galactosidase expression was stable over 28 days ($3.4 \times 10^7 \pm 1.4 \times 10^7$ L.U./mg and $3.18 \times 10^7 \pm 1.1 \times 10^7$ L.U./mg for 10 and 28 days respectively.

Figure 18:
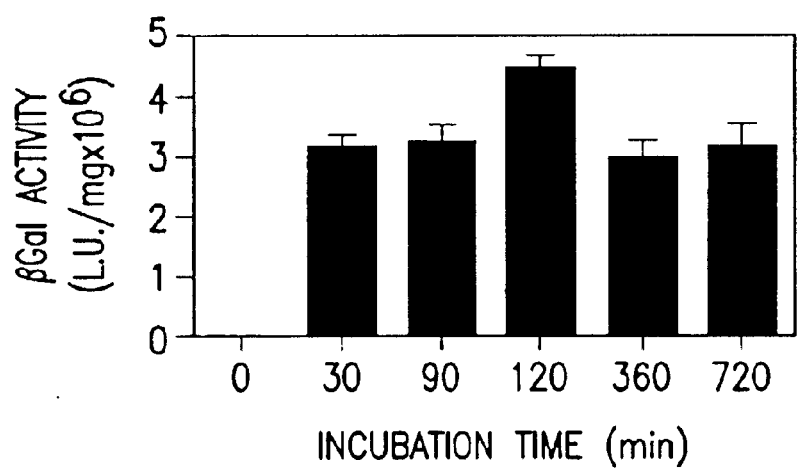
FIG. 18 shows the effect of incubation time on AAV5/βGal-mediated gene transfer to human airway epithelia. Human airway epithelia were exposed to 500 particles per cell of AAV5/βGal from the apical surface. The epithelia were then rinsed after 30, 60 min or 90, 360 and 720 min and incubated for 2 weeks prior to analysis of β-galactosidase activity. Data are the β-gal activity per mg protein±SEM (n=4).

The effect of incubation time for the virion (AAV5/βGal) on airway epithelia was tested. FIG. 18 shows that contrary to what is seen with recombinant adenovirus and AAV2, incubation of airway epithelia with recombinant AAV5 resulted in similar levels of gene transfer with short incubation, 30 min or a prolonged incubation, 12 h. This is in agreement with the increased affinity found for AAV5 compared to AAV2 and adenoviruses and more importantly it suggest there may be an apical receptor for AAV5.

AAV5 Infection of the Apical Surface of Human Airway Epithelia Is not Sensitive to Heparin Competition The low level transduction of airway epithelia by AAV2/βGal is thought to be the result of poor virus binding because the apical membrane of airway epithelia expresses very low levels of HSP and αVβ integrins that may mediate AAV2 binding (54,74). To test the effect of heparin competition on AAV2/βGal and AAV5/βGal transduction of human airway epithelia, the viruses were pre-incubated with 20 μg/ml of soluble heparin. Competition with soluble heparin had minimal effect on the already low level of AAV2/βGal-mediated gene transfer suggesting that the observed low level transduction was not receptor-mediated (FIG. 19A). However more importantly, heparin competition did not inhibit AAV5/βGal-mediated gene transfer to airway epithelia. These data show a novel receptor-mediated pathway for AAV5 binding and infection via the apical surface of human airway epithelia.

Figure 19B:
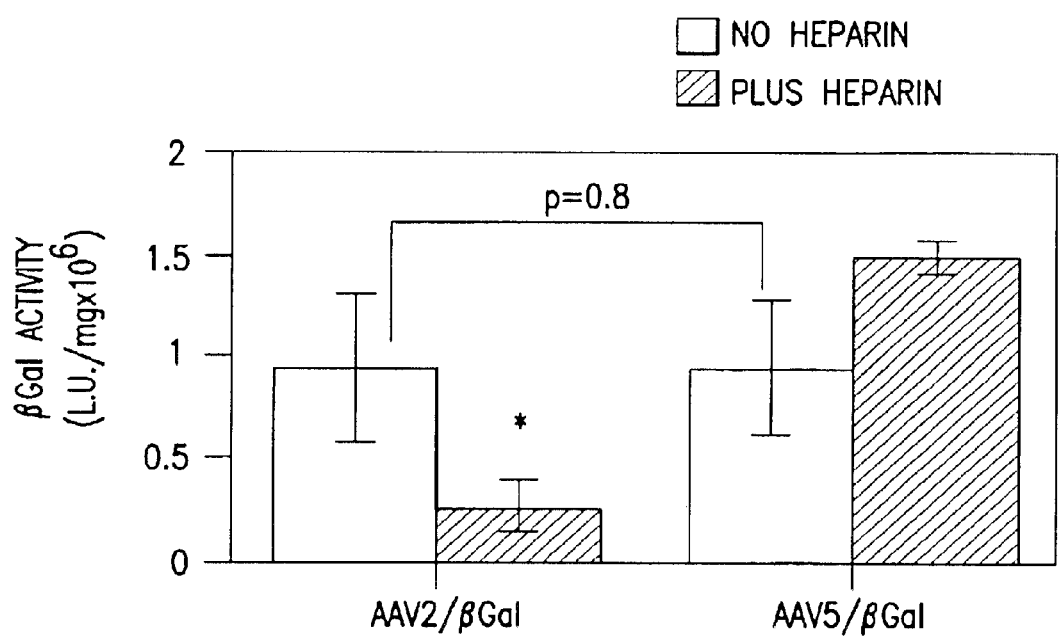

AAV 5 Mediates Gene Transfer through the Basolateral Surface in a Heparin Sulfate Independent Manner The binding of AAV5 to the apical membrane suggests a novel receptor. To test if the receptor for AAV5 is present on the basolateral surface, the transduction experiments were repeated as described in the previous section but vector was applied from the basolateral side. Because AAV2 can infect via the basolateral side, this experimental design also allowed investigation of whether or not AAV5 had an advantage over AAV2 once they were both in the cell. Briefly, the epithelia were turned upside down and 500 virions/cell of AAV5/βGal or AAV2/βGal was carefully applied in a volume of 25 μl to the bottom of the Millipore filter. After 30 min, the epithelia were rinsed thoroughly. To allow for maximal expression, the epithelia were studied 2 weeks after infection. FIG. 19B shows that similar levels of β-galactosidase activity were detected in airway epithelia transduced with either AAV2/βGal or AAV5/βGal. These data suggest that both viruses work equally well when applied to the basolateral side. To test the mechanism of uptake, the studies were repeated in the presence of soluble heparin. As previously reported, basolateral infection of the airway epithelia by AAV2 was competed off by soluble heparin (74). However, the AAV5/βGal transduction via the basolateral surface was not blocked by heparin competition. These data show that that AAV5 binds to a different receptor than AAV2 that is present both on the apical and basolateral surfaces of human airway epithelia.

AAV 5 Mediated Gene Transfer to the Airways in vivo

These data demonstrate improved gene transfer of human ciliated airway epithelia with AAV5 compared to AAV2. To compare the transduction efficiency of AAV5 and AAV2 in vivo, administered either AAV2 or AAV5 ($1 \times 10^{10}$ particles) was administered to 6–8 week old C57BL/6 mice, in a total volume of 125 μl via nasal instillation. After 30 days the mice were sacrificed, and the lungs were fixed and stained with X-Gal as previously described (71). A relatively low viral input was chosen to maximize the difference between specific receptor binding and non-specific binding that may occur when the viral concentrations are very high (70,73, 74,77). Only minimal transduction in mice treated with AAV2/βGal was observed (FIG. 20). In contrast, a significant increase in the number of blue cells in the lungs of mice treated with AAV5 was observed. A 15 fold increase over AAV2 transduction was observed when alveolar cells were transduced with AAV5. These data confirm the in vitro observation that AAV5 is more efficient at mediating gene transfer to the luminal surface of airway epithelia than AAV2 and suggest that murine airway epithelia express the receptor for AAV5.

The data presented in this Example suggest that the capsid of AAV5 is sufficiently different from that of AAV2 to allow for efficient binding and infection of human airway epithelia While previous research has demonstrated transduction of airway epithelial cells with AAV2 those studies have required either very high MOI's and/or prolonged incubation times. The present invention shows that human and murine airway epithelia can be more efficiently transduced by AAV5. Furthermore the data suggest a novel receptor present both in the apical and basolateral surface of airway epithelia.

EXAMPLE V

Preparation of Viral Vectors

AAV5 expressing nuclear targeted β-galactosidase driven off of a Rous sarcoma virus promoter was prepared. Virus was concentrated and suspended in 3% sucrose in phosphate buffered saline prior to in vivo use. AAV5 titres were approximately $1 \times 10^8$ infectious units/ml as assessed by β-galactosidase histochemistry of COS cells transfected with serial dilutions of the viruses. For most of the experiments, the neuronal tracer cholera toxin subunit b (CTb) was added to the viral suspension at a concentration of 1 μg/μl so that CTb immunoreactivity could be used to independently visualize cerebellar injection sites and distinguish transport and spread of virus outside of the injection site from transduction within the primary injection site itself. CTb is the nontoxic, nonbiologically active subunit of cholera toxin and is presumed to be inert in neuronal tracing experiments. Nonetheless, to insure that CTb had no effects on results AAV5, several animals were injected with virus alone (no CTb).

Cerebellar Injections and Preparation of Tissue

Young adult C57B16 mice weighing 20–25 g were anesthetized with ketamine/xylazine, a burr hole was drilled at the midline posterior occipital bone overlying the cerebellar anterior lobe and pressure injections totaling 2 μl were made into a single cerebellar lobule using a Hamilton syringe cemented with a glass micropipette tip. After survival periods, 7 weeks for AAV5, animals were reanesthetized and transcardially perfused with cold phosphate buffered saline followed by 4% paraformalehdye in 0.1 M phosphate buffer, pH 7.4. Cerebella, brainstems and thoracolumbar spinal cords were removed and postfixed in the 4% paraformaldehyde overnight at 4° C., cryoprotected for 1–3 days in 30% sucrose in phosphate buffered saline at 4° C. and then sectioned on a cryostat at 50 μm thickness (cerebellum/brainstem sagitally and spinal cord longitudinally).

Histochemistry and Immunofluorescence

Gene transfer was determined by processing every other section for β-galactosidase staining with 5-bromo4-chloro4-indolyl β-D-galactoside (X-Gal) according to Terashima 1997. Transport and spread of virus was then determined by comparing the X-gal processed sections to adjacent sections that had been processed for CTb immunohistochemistry according to Alisky and Tolbert (1994). Finally, neuronal versus glial gene transduction was determined by dual staining immunofluoresence for β-galactosidase and neuronal and glial markers on selected cerebellar sections. Glial fibrillary acid protein (GFAP) was used as the glial marker and calbindin was used as the neuronal marker; colocalization was then determined by confocal microscopy.

Injection Sites

As determined by CTb immunoreactivity, all injection sites were approximately the area of a single cerebellar lobule in the anterior lobe (lobules U, III, IV or V) encompassing most of the anteroposterior and mediolateral extent of the lobule within the vermis. In some cases, injections encompassed the dorsal half of one lobule and the ventral half of another lobule for a net injection of a single lobule. Injections filled the molecular layer, Purkinje cell layer, granule cell layer and white matter of the arbor vitae but did not extend to the deep cerebellar nucleic. Outside the injection site, the CTb retrogradely labeled precerebellar neurons in the cuneate, vestibular, olivary, reticular and spinal nuclei, thus mapping an extensive pool of neurons which could be potentially transfected via retrograde axonal transport of virus.

AA V5βgal Transduction

There were 12 mice in the AAV arm, seven with AAV5-CTb and five with AAV5 alone, all sacrificed at 7 weeks postinjection. Neuronal cell types could be unequivocally identified because of the unique morphology and position of different neuronal classes within the cerebellar cortex. Stellate neurons are always outermost in the molecular layer, basket cells are in the inner part of the molecular layer, Purkinje cells are always a monolayer and Golgi and granule neurons are exclusively in the granule cell layer. There was no difference between AAV5-CTb and AAV5 alone and tropism of the two vectors was similar. There was extensive AAV5-βgal gene transfer to Purkinje cells, stellate and basket cells and Golgi neurons but only minimal transduction of granule cell neurons (FIG. 21). By immunofluoresence, transduction was exclusively neuronal (FIGS. 22 and 23)

AAV5 showed little retrograde transport but much greater physical spread. The only retrograde transport was to deep cerebellar nuclei; the brainstem vestibular nuclei transduced by the FIV were not transduced by AAV5. However, AAV5-βgalactosidase expressing Purkinje cells could be seen in several lobules far beyond the single lobule injection sites, sometimes the entire anterior and posterior lobes. Moreover AAV5-βgal expressing cells could be seen in the overlying inferior colliculi in x of the animals, clearly diffusion rather than retrograde axonal transport as there are no axon projections from the inferior colliculus into the cerebellum.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

REFERENCES

1. Arella M., Garzon S., Bergeron J., and Tijssen P. *Handbook of Parvoviruses*. Vol. 1. ed. P. Tijssen. Boca Raton, Fla., CRC Press, 1990.
2. Bachmann P A, Hoggan M D, Kurstak E., Melnick J L, Pereira H G, Tattersail P., and Vago C. 1979. Interverology 11: 248–254.
3. Bantel-Schaal U. and Stohr M. 1992. J. Virol. 66: 773–779.
4. Chang L S, Shi Y., and Shenk T. 1989. J. Virol. 63: 3479–88.
5. Cbejanovsky N. and Carter B J 1989. Virology 173: 120–128.
6. Chejanovsky N. and Carter B J 1989. Virology 171: 239–247.
7. Chiorini J A, Wiener S M, Kotin R M, Owens R A, Kyostid S R M, and Safer B. 1994. J. Virol. 68: 7448–7457.
8. Chiorini J A, Weitzman M D, Owens R A, Urcelay E., Safer B., and Kotin R M 1994. J. Virol. 68: 797–804.
9. Chiorini J A, Wendtner C M, Urcelay E., Safer B., Hallek M., and Kotin R. M. 1995. Human Gene Therapy 6: 1531–1541.
10. Chiorini J A, Yang L., Safer B., and Kotin R M 1995. J. Virol. 69: 7334–7338.
11. Dixit M., Webb M S, Smart W C, and Ohi S. 1991. Gene 104: 253–7.
12. Fisher R E and Mayor H D 1991. J Theor Biol 149: 429–39.
13. Flotte T R, Afione S A, Conrad C., McGrath S A, Solow R., Oka H., Zeitlin P L, Guggino W B, and Carter B J 1993. Proc. Natl. Acad. Sci. 90: 10613–10617.
14. Flotte, T. R., S. A. Afione, R. Solow, M. L. Drumm, D. Markakis, W. B. Guggino, P. L. Zeitlin, and B. J. Carter. 1993. J Biol Chem 268: 3781–90.
15. Hermonat, P. L., M. A. Labow, R. Wright, K. I. Berns, and N. Muzyczka. 1984. J. Virol. 51: 329–339.
16. Hermonat, P. L. and N. Muzyczka. 1984. Proc Natl Acad Sci USA 81: 6466–70.
17. Hunter, L. A. and R. J. Samulski. 1992. J. Virol. 66: 317–24:
18. Ito, M. and H. D. Mayor. 1968. J. Immuno. 100: 61–68.
19. Janik, J. E., M. M. Huston, K. Cho, and J. A. Rose. 1989. Virology 168: 320–9.
20. Kaplitt, M. G., P. Leone, R. J. Samulski, X. Xiao, D. W. Pfaff, K. L. O'Malley, and J. M. During. 1994. Nature Genetics 8: 148–154.
21. Kotin, R. M., M. Siniscalco, R. J. Samulski, X. Zhu, L. Hunter, C. A. Laughlin, S. McLaughlin, N. Muzyczka, M. Rocchi, and K. I. Berns. 1990. Proc. Natl. Acad. Sci. (USA) 87: 2211–2215.
22. Laughlin, C. A., N. Jones, and B. J. Carter. 1982. J. Virol. 41: 868–76.
23. Laughlin, C. A., M. W. Myers, D. L. Risin, B. J. Carter. 1979. Virology 94: 162–74.
24. McCarty, D. M., J. Pereira, I. Zolotukhin, X. Zhou, J. H. Ryan, and N. Muzyczka. 1994. J. Virol. 68: 49884997.
25. Mendelson, E., J. P. Trempe, and B. J. Carter. 1986. J. Virol. 60: 823–832.
26. Mizukami, H., N. S. Young, and K. E. Brown. 1996. Virology 217:124–130.
27. Muster, C. J., Y. S. Lee, J. E. Newbold, and J. Leis. 1980. J. Virol. 35: 653–61.
28. Muzyczka, N. 1992. Curr Top Microbiol Immunol 158: 97–129.
29. Parks, W. P., J. L. Melnick, R. Roogey, and H. D. Mayor. 1967. J. Virol. 1: 171–180.
30. Podsakoff, G., K. K. Jr Wong, and S. Chatterjee. 1994. J. Virol. 68: 5656–5666.
31. Rose, J. A., M. D. Hoggan, F. Koczot, and A. J. Shatkin. 1968. J. Virol. 2: 999–1005.
32. Russell, D. W., A. D. Miller, and I. E. Alexander. 1994. Proc. Natl. Acad. Sci. USA 91: 8915–8919.
33. Ryan, J. H., S. Zolotukhin, and N. Muzyczka. 1996. J. Virol. 70: 1542–1553.
34. Samulski, R. J., K. I. Berns, M. Tan, and N. Muzyczka. 1982. Proc Natl Acad Sci USA 79: 2077–81.
35. Samulski, R. J., L. S. Chang, and T. Shenk. 1989. J. Virol. 63: 3822–8.
36. Sanes, J. R., J. L. R. Rubenstein, and J. F. Nicocas. 1986. *EMBO* 5: 3133–3142.
37. Senapathy, P., J. D. Tratschin, and B. J. Carter. 1984. J Mol Biol 179: 1–20.
38. Tratschin, J. D., I. L. Miller, and B. J. Carter. 1984. J. Virol. 51: 611–619.

39. Trempe, J. P. and B. J. Carter. 1988. J. Virol. 62: 68–74.
40. Trempe, J. P., E. Mendelson, and B. J. Carter. 1987. Virology 161: 18–28.
41. Walsh, C. E., J. M. Liu, X. Xiao, N. S. Young, A. W. Nienhuis, and R. J. Samulski. 1992. Proc Natl Acad Sci USA 89: 7257–61.
42. Winocour, E., M. F. Callaham, and E. Huberman. 1988. Virology 167: 393–9.
43. Jaksch, M., K. D. Gerbitz, and C. Kilger. 1995. Clin. Biochem. 28:503–509
44. Burcin, M. M., O'Malley, B. W. and S. Y. Tsai. 1998. Frontiers in Bioscience 3:1–7.
45. Chiorini J. A., Kim F., Yang L., Kotin R. M. 1999 J Virol 73(2):1309–1319.
46. Hehir K. M., Armentano D., Cardoza L. M., Choquette T. L., Berthelette P. B., White G. A., Couture L. A., Everton M. B., Keegan J., Martin J. M., Pratt D. A., Smith M. P., Smith A. E., Wadsworth S. C. 1996 J Virol 70(12):8459–8467.
47. Ghodsi A., Stein, C., Derksen T., Yang, G., Anderson R. D., Davidson B. L. 1998 Hum Gene Ther 9:2331–2340.
48. Davidson B L, Doran S E, Shewach D S, Latta J M, Hartman J W, Roessler B J. 1994 Exp Neurol 125:258–267.
49. McCown T J, Xiao X, Li J, Breese G R, Samulski R J. 1996 Brain Res 713:99–107.
50. Lo W D, Qu G, Sferra T J, Clark R, Chen R, Johnson P R. 1999 Hum Gene Ther 10:201–213.
51. Mandel R J, Rendahl K G, Spratt S K, Snyder R O, Cohen L K, Leff S E. 1998 J Neurosci 18(11):4271–4284.
52. Summerford C, Samulski R J. 1998 J Virol 72(2): 1438–1445.
53. Qing K, Mah C, Hansen J, Zhou S, Dwarki V, Srivastava A. 1999 Nat Med 5(1):71 –77.
54. Summerford C, Bartlett J S, Samulski R J. 1999 Nat Med 5(1):78–82.
55. Qiu J, Brown K E. 1999 Virology 264(2):436–440.
56. Bantel-Schaal U, Delius H, Schmidt R, zur Hausen H. 1999 J Virol 73(2):939–947.
57. Bartlett J S, Samulski R J, McCown T J. 1998 Hum Gene Ther 9(8): 1181–11186.
58. Hsueh Y-P, Yang F-C, Kharazia V, Naisbitt S, Cohen A R, Weinberg R J, Sheng M 1998 J Cell Biol 142(1): 139–151.
59. Hsueh Y-P, Sheng M. 1999 J Neurosci 19(17): 7415–7425.
60. Liang Y, Annan R S, Carr S A, Popp S, Mevissen M, Margolis R K, Margolis R U. 1999 J Biol Chem 274(25): 17885–17892.
61. Fan D-S, Ogawa M, Fujimoto K-I, Ikeguchi K, Ogasawara Y, Urabe M, Nishizawa M, Nakano I, Yoshida M, Nagatsu I, Ichinose H, Nagatsu T, Kurtzman G J, Ozawa K 1998 Hum Gene Ther 9:2527–2535.
62. Doll R F, Crandall J E, Dyer C A, Aucoin J M, Smith F I. 1996 Gene Ther 3:437–447.
63. Klein R L, Meyer E M, Peel A L, Zolotukhin S, Meyers C, Muzyczka N, King M A. 1998 Exp Neurol 150:183–194.
64. Bajocchi G, Feldman S H, Crystal R G, Mastrangeli A. 1993 Nat Genet 3:229–234.
65. Ghodsi A., Stein C., Derksen T., Martins I., Anderson R D, & Davidson B L 1999 Exp Neurol 160, 109–116.
66. Johansson C B, Momma S, Clarke D L, Risling M, Lendahl U, Frisen J 1999 Cell 96(1):25–34.
67. Rich D P, Couture L A, Cardoza L M, Guiggio L M, Armentano D., Espino P C, Hehir K., Welsh M J, Smith A E, and Gregory R J 1993 Hum.Gene Ther. 4:461476.
68. Kondo M., Finkbeiner W E, and Widdicombe J H. 1991. Am.J.Physiol. 261 :Li06-L117
69. Yamaya, M., Finkbeiner W E, Chun S Y, and Widdicombe J H 1992 Am.J.Physiol. 262:L713-L724
70. Zabner, J., Zeiber B G, Friedman E, and Welsh M J 1996 J.Virol. 70:6994–7003.
71. Walters, R W, Duan D., Engelhardt J F, and Welsh M J. 1999. J. Virol. (In Press)
72. Bergelson, J M, Cunningham J A, Drogueft G., Kurt-Jones E A, Krithivas A., Hong J S, Horwitz M S, Crowell R L, and Finberg R W 1997 Science 275:1320–1323.
73. Teramoto, S., Bartlett J S, McCarty DXX, Samulski R J, and Boucher R C 1998 J Virol 72:8904–8912.
74. Duan, D., Yue Y., Yan Z., McCray P B Jr, and Engelhardt J F. 1998 Hum Gene Ther 9:2761–2776.
75. Walters, R W, Grunst T., Bergelson J M, Finberg R W, Welsh M J, and Zabner J. 1999 J. Biol. Chem. 274:10219–10226.
76. Wang G., Davidson B L, Melchert P., Slepushkin V A, van Es H H, Bodner M., Jolly D J, and McCray P B Jr. 1998. Journal of Virology 72:9818–9826.
77. Halbert C L, Standaert T A, Aitken M L, Alexander I E, Russell D W, and Miller A D 1997. J.Virol. 71:5932–5941.
78. Fisher, K J, Jooss K., Alston J., Yang Y., Haecker S E, High K, Pathak R., Raper S E, and Wilson J M 1997 Nat Med 3:306–312.
79. Guy J., Qi X., Muzyczka N., and Hauswirth W W 1999 Arch Ophthalmol 117:929–937.
80. Snyder R O, Miao C H, Patijn G A, Spratt S K, Danos O., Nagy D., Gown A M, Winther B., Meuse L., Cohen L K, Thompson A R, and Kay M A 1997. Nat.Genet. 16:270–276.
81. Girod A., Ried M., Wobus C., Lahm H., Leike K, Kleinschmidt J., Deleage G., and Hallek M. 1999 Nat Med 5:1052–1056.
82. Bartlett J S, Kleinschmidt J., Boucher R C, and Samulski R J 1999 Nat Biotechnol 17:181–186.
83. Xiao W., Chirmule N., Berta S C, McCullough B., Gao G., and Wilson J M 1999 J Virol 73:3994–4003.
84. Rutledge E A, Halbert C L, and Russell D W 1998 J Virol 72:309–319.
85. Xie Q. and Chapman M S 1996 J Mol Biol 264:497–520.
86. Alisky J. M. and Tolbert D. M. 1994 Journal of Neuroscience Methods 52: 143–148.

What is claimed is:

1. A method of delivering a nucleic acid to an alveolar acid cell, in vitro, comprising administering to the alvcolar cell a AAV5 particle containing a vector comprising the nucleic acid inserted between a pair of AAV inverted terminal repeats, thereby delivering the nucleic acid to the cell.

2. A method of delivering a nucleic acid to an alvcolar cell in a subject comprising administering to the subject an AAV5 particle comprising the nucleic acid inserted between a pair of AAV inverted terminal repeats, wherein the AAV5 particle is delivered intranasally, thereby delivering the nucleic acid to an alvcolar cell in the subject.

3. A method of delivering a nucleic acid to an alvcolar cell in a subject comprising administering to the subject an AAV5 particle comprising the nucleic acid inserted between a pair of AAV inverted terminal repeats, wherein the AAV5 particle is delivered via aerosol, thereby delivering the nucleic acid to an alvcolar cell in the subject.

4. A method of delivering a nucleic acid to an alvcolar cell in a subject comprising administering to the subject an AAV5 particle comprising the nucleic acid inserted between a pair of AAV inverted terminal repeats, wherein the AAV5 particle is delivered via the airway, thereby delivering the nucleic acid to an alvcolar cell in the subject.

5. A method of delivering a nucleic acid to a cerebellar cell, in vitro, comprising administering to the cerebellar cell an AAV5 particle containing vector comprising the nucleic acid inserted between a pair of AAV inverted terminal repeats, wherein delivering the nucleic acid to the cell.

6. A method of delivering a nucleic acid to an cerebellar cell in a subject comprising administering to the subject an AAV5 particle comprising the nucleic acid inserted between a pair of AAV inverted terminal repeats, wherein the AAV5 particle is delivered directly to the brain of the subject, thereby delivering the nucleic acid to a cerebellar cell in the subject.

7. A method of delivering a nucleic acid to an ependymal cell, in vitro comprising administering to the ependymal cell an AAV5 particle comprising a vector comprising the nucleic acid inserted between a pair of AAV inverted terminal repeats, thereby delivering the nucleic acid to an ependymal cell.

8. A method of delivering a nucleic acid to an ependymal cell in a subject comprising administering to the subject an AAV5 particle comprising the nucleic acid inserted between a pair of AAV inverted terminal repeats, wherein the AAV5 particle is delivered directly to the brain of the subject, thereby delivering the nucleic acid to an ependymal cell in the subject.

9. The method of any of claims 1–2 and 3–8, wherein the AAV inverted terminal repeats are AAV5 terminal repeats.

* * * * *